United States Patent
Jacobson et al.

(10) Patent No.: US 10,207,240 B2
(45) Date of Patent: Feb. 19, 2019

(54) METHODS AND MICROFLUIDIC DEVICES FOR THE MANIPULATION OF DROPLETS IN HIGH FIDELITY POLYNUCLEOTIDE ASSEMBLY

(75) Inventors: Joseph Jacobson, Newton, MA (US); Larry Li-Yang Chu, Cambridge, MA (US); Senthil Ramu, Boston, MA (US)

(73) Assignee: Gen9, Inc., Cambridge, MA (US)

( * ) Notice: Subject to any disclaimer, the term of this patent is extended or adjusted under 35 U.S.C. 154(b) by 0 days.

(21) Appl. No.: 13/505,646

(22) PCT Filed: Nov. 3, 2010

(86) PCT No.: PCT/US2010/055298
§ 371 (c)(1),
(2), (4) Date: May 2, 2012

(87) PCT Pub. No.: WO2011/056872
PCT Pub. Date: May 12, 2011

(65) Prior Publication Data
US 2012/0220497 A1      Aug. 30, 2012

Related U.S. Application Data

(60) Provisional application No. 61/257,591, filed on Nov. 3, 2009, provisional application No. 61/264,641, filed on Nov. 25, 2009, provisional application No. 61/310,069, filed on Mar. 3, 2010.

(51) Int. Cl.
| | |
|---|---|
| C40B 60/14 | (2006.01) |
| C40B 60/00 | (2006.01) |
| C40B 40/06 | (2006.01) |
| B01J 19/00 | (2006.01) |
| B01L 3/00 | (2006.01) |
| B82Y 30/00 | (2011.01) |
| C12Q 1/68 | (2018.01) |
| B01L 3/02 | (2006.01) |
| B01L 7/00 | (2006.01) |

(52) U.S. Cl.
CPC ..... *B01J 19/0046* (2013.01); *B01L 3/502792* (2013.01); *B82Y 30/00* (2013.01); *B01J 2219/0065* (2013.01); *B01J 2219/00378* (2013.01); *B01J 2219/00495* (2013.01); *B01J 2219/00608* (2013.01); *B01J 2219/00621* (2013.01); *B01J 2219/00644* (2013.01); *B01J 2219/00653* (2013.01); *B01J 2219/00659* (2013.01); *B01J 2219/00675* (2013.01); *B01J 2219/00722* (2013.01); *B01L 3/0262* (2013.01); *B01L 3/0268* (2013.01); *B01L 3/5088* (2013.01); *B01L 7/52* (2013.01); *B01L 2300/10* (2013.01); *B01L 2300/1861* (2013.01); *B01L 2400/043* (2013.01); *B01L 2400/0427* (2013.01); *B01L 2400/0439* (2013.01); *B01L 2400/0454* (2013.01); *C12Q 2565/629* (2013.01)

(58) Field of Classification Search
CPC ......... C12P 19/34; C12N 15/10; C40B 50/14; C40B 40/06
USPC ................... 506/16, 30; 536/25.3
See application file for complete search history.

(56) References Cited

U.S. PATENT DOCUMENTS

| | | |
|---|---|---|
| 4,500,707 A | 2/1985 | Caruthers et al. |
| 4,683,195 A | 7/1987 | Mullis et al. |
| 4,683,202 A | 7/1987 | Mullis |
| 4,689,405 A | 8/1987 | Frank et al. |
| 4,725,677 A | 2/1988 | Koster et al. |
| 4,800,159 A | 1/1989 | Mullis et al. |
| 4,965,188 A | 10/1990 | Mullis et al. |

(Continued)

FOREIGN PATENT DOCUMENTS

| | | |
|---|---|---|
| EP | 0259160 A2 | 3/1988 |
| EP | 1015576 A1 | 7/2000 |

(Continued)

OTHER PUBLICATIONS

Qui et al., Product Application Focus, Mutation Detection Using Surveyor Nuclease, BioTechniquies, 2004, 36(4), 702-707.*

(Continued)

*Primary Examiner* — Amy M Bunker
(74) *Attorney, Agent, or Firm* — Choate, Hall & Stewart LLP; Brenda Herschbach Jarrell; Robert N. Sahr

(57) ABSTRACT

Methods and devices are provided for manipulating droplets on a support using surface tension properties, moving the droplets along a predetermined path and merging two droplets together enabling a number of chemical reactions. Disclosed are methods for controlling the droplets volumes. Disclosed are methods and devices for synthesizing at least one oligonucleotide having a predefined sequence. Disclosed are methods and devices for synthesizing and/or assembling at least one polynucleotide product having a predefined sequence from a plurality of different oligonucleotides having a predefined sequence. In exemplary embodiments, the methods involve synthesis and/or amplification of different oligonucleotides immobilized on a solid support, release of synthesized/amplified oligonucleotides in solution to form droplets, recognition and removal of error-containing oligonucleotides, moving or combining two droplets to allow hybridization and/or ligation between two different oligonucleotides, and further chain extension reaction following hybridization and/or ligation to hierarchically generate desired length of polynucleotide products.

12 Claims, 32 Drawing Sheets

(56) References Cited

U.S. PATENT DOCUMENTS

| | | |
|---|---|---|
| 4,999,294 A | 3/1991 | Looney et al. |
| 5,047,524 A | 9/1991 | Andrus et al. |
| 5,104,789 A | 4/1992 | Permar et al. |
| 5,104,792 A | 4/1992 | Silver et al. |
| 5,132,215 A | 7/1992 | Jayaraman et al. |
| 5,143,854 A | 9/1992 | Pirrung et al. |
| 5,288,514 A | 2/1994 | Ellman |
| 5,356,802 A | 10/1994 | Chandrasegaran |
| 5,384,261 A | 1/1995 | Winkler et al. |
| 5,405,783 A | 4/1995 | Pirrung et al. |
| 5,424,186 A | 6/1995 | Fodor et al. |
| 5,436,150 A | 7/1995 | Chandrasegaran |
| 5,436,327 A | 7/1995 | Southern et al. |
| 5,445,934 A | 8/1995 | Fodor et al. |
| 5,459,039 A | 10/1995 | Modrich et al. |
| 5,474,796 A | 12/1995 | Brennan |
| 5,498,531 A | 3/1996 | Jarrell |
| 5,508,169 A | 4/1996 | Deugau et al. |
| 5,510,270 A | 4/1996 | Fodor et al. |
| 5,512,463 A | 4/1996 | Stemmer |
| 5,514,789 A | 5/1996 | Kempe |
| 5,527,681 A | 6/1996 | Holmes |
| 5,541,061 A | 7/1996 | Fodor et al. |
| 5,605,793 A | 2/1997 | Stemmer |
| 5,624,711 A | 4/1997 | Sundberg et al. |
| 5,639,603 A | 6/1997 | Dower et al. |
| 5,641,658 A | 6/1997 | Adams et al. |
| 5,653,939 A | 8/1997 | Hollis et al. |
| 5,658,802 A | 8/1997 | Hayes et al. |
| 5,674,742 A | 10/1997 | Northrup et al. |
| 5,679,522 A | 10/1997 | Modrich et al. |
| 5,695,940 A | 12/1997 | Drmanac et al. |
| 5,700,637 A | 12/1997 | Southern |
| 5,700,642 A | 12/1997 | Monforte et al. |
| 5,702,894 A | 12/1997 | Modrich et al. |
| 5,738,829 A | 4/1998 | Kempe |
| 5,739,386 A | 4/1998 | Holmes |
| 5,750,335 A | 5/1998 | Gifford |
| 5,766,550 A | 6/1998 | Kaplan et al. |
| 5,770,358 A | 6/1998 | Dower et al. |
| 5,780,272 A | 7/1998 | Jarrell |
| 5,795,714 A | 8/1998 | Cantor et al. |
| 5,830,655 A | 11/1998 | Monforte et al. |
| 5,830,721 A | 11/1998 | Stemmer |
| 5,834,252 A | 11/1998 | Stemmer et al. |
| 5,858,754 A | 1/1999 | Modrich et al. |
| 5,861,482 A | 1/1999 | Modrich et al. |
| 5,871,902 A | 2/1999 | Weininger et al. |
| 5,877,280 A | 3/1999 | Wetmur |
| 5,916,794 A | 6/1999 | Chandrasegaran |
| 5,922,539 A | 7/1999 | Modrich et al. |
| 5,928,905 A | 7/1999 | Stemmer et al. |
| 5,929,208 A | 7/1999 | Heller et al. |
| 5,942,609 A | 8/1999 | Hunkapiller et al. |
| 5,953,469 A | 9/1999 | Zhou |
| 6,008,031 A | 12/1999 | Modrich et al. |
| 6,013,440 A | 1/2000 | Lipshutz et al. |
| 6,017,696 A | 1/2000 | Heller |
| 6,042,211 A | 3/2000 | Hudson et al. |
| 6,093,302 A | 7/2000 | Montgomery |
| 6,103,463 A | 8/2000 | Chetverin et al. |
| 6,136,568 A | 10/2000 | Hiatt et al. |
| 6,150,102 A | 11/2000 | Mills |
| 6,150,141 A | 11/2000 | Jarrell |
| 6,165,793 A | 12/2000 | Stemmer |
| 6,177,558 B1 | 1/2001 | Brennan et al. |
| 6,242,211 B1 | 6/2001 | Peterson et al. |
| 6,248,521 B1 | 6/2001 | Van Ness et al. |
| 6,261,797 B1 | 7/2001 | Sorge et al. |
| 6,271,957 B1 | 8/2001 | Quate et al. |
| 6,277,632 B1 | 8/2001 | Harney |
| 6,280,595 B1 | 8/2001 | Montgomery |
| 6,284,463 B1 | 9/2001 | Hasebe et al. |
| 6,287,825 B1 | 9/2001 | Weissman et al. |
| 6,287,861 B1 | 9/2001 | Stemmer et al. |
| 6,291,242 B1 | 9/2001 | Stemmer |
| 6,315,958 B1 | 11/2001 | Singh-Gasson et al. |
| 6,322,971 B1 | 11/2001 | Chetverin et al. |
| 6,333,153 B1 | 12/2001 | Fishel et al. |
| 6,346,399 B1 | 2/2002 | Weissman et al. |
| 6,358,712 B1 | 3/2002 | Jarrell et al. |
| 6,365,355 B1 | 4/2002 | McCutchen-Maloney |
| 6,372,434 B1 | 4/2002 | Weissman et al. |
| 6,372,484 B1 | 4/2002 | Ronchi et al. |
| 6,375,903 B1 | 4/2002 | Cerrina et al. |
| 6,406,847 B1 | 6/2002 | Cox et al. |
| 6,410,220 B1 | 6/2002 | Hodgson et al. |
| 6,416,164 B1 | 7/2002 | Stearns et al. |
| 6,426,184 B1 | 7/2002 | Gao et al. |
| 6,444,111 B1 | 9/2002 | Montgomery |
| 6,444,175 B1 | 9/2002 | Singh-Gasson et al. |
| 6,479,652 B1 | 11/2002 | Crameri |
| 6,480,324 B2 | 11/2002 | Quate et al. |
| 6,489,146 B2 | 12/2002 | Stemmer et al. |
| 6,495,318 B2 | 12/2002 | Harney |
| 6,506,603 B1 | 1/2003 | Stemmer |
| 6,511,849 B1 | 1/2003 | Wang |
| 6,514,704 B2 | 2/2003 | Bruce |
| 6,521,427 B1 | 2/2003 | Evans |
| 6,534,271 B2 | 3/2003 | Furste et al. |
| 6,537,776 B1 | 3/2003 | Short |
| 6,565,727 B1 | 5/2003 | Shenderov |
| 6,586,211 B1 | 7/2003 | Stahler |
| 6,596,239 B2 | 7/2003 | Williams et al. |
| 6,605,451 B1 | 8/2003 | Marmaro et al. |
| 6,610,499 B1 | 8/2003 | Fulwyler et al. |
| 6,613,581 B1 | 9/2003 | Wada et al. |
| 6,632,641 B1 | 10/2003 | Brennan et al. |
| 6,650,822 B1 | 11/2003 | Zhou |
| 6,658,802 B2 | 12/2003 | Lucas, Jr. et al. |
| 6,664,112 B2 | 12/2003 | Mulligan et al. |
| 6,664,388 B2 | 12/2003 | Nelson |
| 6,670,127 B2 | 12/2003 | Evans |
| 6,670,605 B1 | 12/2003 | Storm, Jr. et al. |
| 6,800,439 B1 | 10/2004 | McGall et al. |
| 6,802,593 B2 | 10/2004 | Ellson et al. |
| 6,824,866 B1 | 11/2004 | Glazer et al. |
| 6,830,890 B2 | 12/2004 | Lockhart et al. |
| 6,833,450 B1 | 12/2004 | McGall et al. |
| 6,846,655 B1 | 1/2005 | Wagner et al. |
| 6,897,025 B2 | 5/2005 | Cox et al. |
| 6,911,132 B2 | 6/2005 | Pamula et al. |
| 6,921,818 B2 | 7/2005 | Sproat |
| 6,932,097 B2 | 8/2005 | Ellson et al. |
| 6,969,587 B2 | 11/2005 | Taylor |
| 6,969,847 B2 | 11/2005 | Davis et al. |
| 7,090,333 B2 | 8/2006 | Mutz et al. |
| 7,129,091 B2 | 10/2006 | Ismagilov et al. |
| 7,133,782 B2 | 11/2006 | Odedra |
| 7,169,560 B2 | 1/2007 | Lapidus et al. |
| 7,179,423 B2 | 2/2007 | Bohm et al. |
| 7,183,406 B2 | 2/2007 | Belshaw |
| 7,262,031 B2 | 8/2007 | Lathrop |
| 7,273,730 B2 | 9/2007 | Du Breuil Lastrucci |
| 7,303,320 B1 | 12/2007 | Ashley |
| 7,303,872 B2 | 12/2007 | Sussman |
| 7,323,320 B2 | 1/2008 | Oleinikov |
| 7,399,590 B2 | 7/2008 | Piepenburg et al. |
| 7,432,055 B2 | 10/2008 | Pemov et al. |
| 7,498,176 B2 | 3/2009 | McCormick et al. |
| 7,514,210 B2 * | 4/2009 | Holliger ............... C12N 9/1252 435/194 |
| 7,563,600 B2 | 7/2009 | Oleinikov |
| 7,820,412 B2 | 10/2010 | Belshaw |
| 7,879,580 B2 | 2/2011 | Carr |
| 8,053,191 B2 | 11/2011 | Blake |
| 8,058,004 B2 | 11/2011 | Oleinikov |
| 8,173,368 B2 | 5/2012 | Staehler et al. |
| 8,716,467 B2 | 5/2014 | Jacobson |
| 8,808,986 B2 | 8/2014 | Jacobson et al. |
| 9,023,601 B2 | 5/2015 | Oleinikov |
| 9,051,666 B2 | 6/2015 | Oleinikov |
| 9,216,414 B2 | 12/2015 | Chu |
| 9,968,902 B2 | 5/2018 | Chu |

(56) References Cited

U.S. PATENT DOCUMENTS

| | | |
|---|---|---|
| 2001/0012537 A1 | 8/2001 | Anderson et al. |
| 2001/0031483 A1 | 10/2001 | Sorge et al. |
| 2001/0049125 A1 | 12/2001 | Stemmer et al. |
| 2002/0012616 A1 | 1/2002 | Zhou et al. |
| 2002/0037579 A1 | 3/2002 | Ellson et al. |
| 2002/0058275 A1 | 5/2002 | Fishel et al. |
| 2002/0058322 A1 | 5/2002 | Boone et al. |
| 2002/0081582 A1 | 6/2002 | Gao et al. |
| 2002/0119459 A1* | 8/2002 | Griffiths ............. C12N 15/1062 435/6.16 |
| 2002/0127552 A1 | 9/2002 | Church et al. |
| 2002/0132259 A1 | 9/2002 | Wagner et al. |
| 2002/0132308 A1 | 9/2002 | Liu et al. |
| 2002/0133359 A1 | 9/2002 | Brown |
| 2003/0017552 A1 | 1/2003 | Jarrell et al. |
| 2003/0044980 A1 | 3/2003 | Mancebo et al. |
| 2003/0047688 A1 | 3/2003 | Faris et al. |
| 2003/0050437 A1 | 3/2003 | Montgomery |
| 2003/0050438 A1 | 3/2003 | Montgomery |
| 2003/0054390 A1 | 3/2003 | Crameri et al. |
| 2003/0068633 A1 | 4/2003 | Belshaw et al. |
| 2003/0068643 A1 | 4/2003 | Brennan et al. |
| 2003/0082630 A1 | 5/2003 | Kolkman et al. |
| 2003/0087298 A1 | 5/2003 | Green et al. |
| 2003/0091476 A1 | 5/2003 | Zhou et al. |
| 2003/0099952 A1 | 5/2003 | Green et al. |
| 2003/0118485 A1 | 6/2003 | Singh-Gasson et al. |
| 2003/0118486 A1 | 6/2003 | Zhou et al. |
| 2003/0120035 A1 | 6/2003 | Gao et al. |
| 2003/0134807 A1 | 7/2003 | Hardin et al. |
| 2003/0143550 A1 | 7/2003 | Green et al. |
| 2003/0143724 A1 | 7/2003 | Cerrina et al. |
| 2003/0170616 A1 | 9/2003 | Wang et al. |
| 2003/0171325 A1 | 9/2003 | Gascoyne |
| 2003/0175907 A1 | 9/2003 | Frazer et al. |
| 2003/0186226 A1 | 10/2003 | Brennan |
| 2003/0198948 A1 | 10/2003 | Stahler et al. |
| 2003/0215837 A1 | 11/2003 | Frey |
| 2003/0215855 A1 | 11/2003 | Dubrow et al. |
| 2003/0215856 A1 | 11/2003 | Church et al. |
| 2004/0002103 A1 | 1/2004 | Short |
| 2004/0005673 A1 | 1/2004 | Jarrell et al. |
| 2004/0009479 A1 | 1/2004 | Wohlgemuth et al. |
| 2004/0009520 A1 | 1/2004 | Albert |
| 2004/0014083 A1 | 1/2004 | Yuan |
| 2004/0101444 A1 | 5/2004 | Sommers et al. |
| 2004/0101894 A1 | 5/2004 | Albert et al. |
| 2004/0101949 A1 | 5/2004 | Green et al. |
| 2004/0106728 A1 | 6/2004 | McGall et al. |
| 2004/0110211 A1 | 6/2004 | McCormick et al. |
| 2004/0110212 A1 | 6/2004 | McCormick et al. |
| 2004/0126757 A1 | 7/2004 | Cerrina |
| 2004/0132029 A1 | 7/2004 | Sussman et al. |
| 2004/0166567 A1 | 8/2004 | Santi et al. |
| 2004/0171047 A1 | 9/2004 | Dahl et al. |
| 2004/0185484 A1* | 9/2004 | Costa et al. ................. 435/6 |
| 2004/0241655 A1 | 12/2004 | Hwang et al. |
| 2004/0259146 A1 | 12/2004 | Friend et al. |
| 2005/0053997 A1 | 3/2005 | Evans |
| 2005/0069928 A1 | 3/2005 | Nelson et al. |
| 2005/0074898 A1 | 4/2005 | Datwani et al. |
| 2005/0079510 A1 | 4/2005 | Berka et al. |
| 2005/0106606 A1 | 5/2005 | Parker et al. |
| 2005/0118628 A1 | 6/2005 | Evans |
| 2005/0202429 A1 | 9/2005 | Trau et al. |
| 2005/0227235 A1 | 10/2005 | Carr et al. |
| 2005/0255477 A1 | 11/2005 | Carr et al. |
| 2006/0008833 A1 | 1/2006 | Jacobson |
| 2006/0040297 A1 | 2/2006 | Leamon et al. |
| 2006/0054503 A1 | 3/2006 | Pamula et al. |
| 2006/0127920 A1 | 6/2006 | Church et al. |
| 2006/0127926 A1 | 6/2006 | Belshaw et al. |
| 2006/0134638 A1 | 6/2006 | Mulligan et al. |
| 2006/0160138 A1 | 7/2006 | Church et al. |
| 2006/0194214 A1 | 8/2006 | Church et al. |
| 2007/0004041 A1 | 1/2007 | Church et al. |
| 2007/0052781 A1 | 3/2007 | Fraden et al. |
| 2007/0122817 A1 | 5/2007 | Church et al. |
| 2007/0231805 A1 | 10/2007 | Baynes |
| 2007/0269870 A1* | 11/2007 | Church et al. ................ 435/91.2 |
| 2007/0281309 A1 | 12/2007 | Kong |
| 2008/0009420 A1 | 1/2008 | Schroth et al. |
| 2008/0014589 A1 | 1/2008 | Link et al. |
| 2008/0085513 A1 | 4/2008 | Leproust et al. |
| 2008/0105829 A1 | 5/2008 | Faris et al. |
| 2008/0274513 A1 | 11/2008 | Shenderov et al. |
| 2008/0300842 A1 | 12/2008 | Govindarajan et al. |
| 2009/0016932 A1 | 1/2009 | Curcio et al. |
| 2009/0087840 A1 | 4/2009 | Baynes et al. |
| 2009/0137408 A1 | 5/2009 | Jacobson |
| 2009/0311713 A1 | 12/2009 | Pollack et al. |
| 2010/0015614 A1 | 1/2010 | Beer et al. |
| 2010/0015668 A1 | 1/2010 | Staehler et al. |
| 2010/0016178 A1 | 1/2010 | Sussman et al. |
| 2011/0008775 A1 | 1/2011 | Gao et al. |
| 2011/0117625 A1 | 5/2011 | Lippow et al. |
| 2011/0172127 A1* | 7/2011 | Jacobson ............... B01L 3/0268 506/26 |
| 2011/0217738 A1 | 9/2011 | Jacobson |
| 2012/0028843 A1 | 2/2012 | Ramu et al. |
| 2012/0220497 A1 | 8/2012 | Jacobson et al. |
| 2012/0270754 A1 | 10/2012 | Blake |
| 2012/0283110 A1 | 11/2012 | Shendure et al. |
| 2012/0283140 A1 | 11/2012 | Chu |
| 2012/0315670 A1 | 12/2012 | Jacobson et al. |
| 2012/0322681 A1 | 12/2012 | Kung et al. |
| 2013/0059296 A1 | 3/2013 | Jacobson et al. |
| 2013/0059761 A1 | 3/2013 | Jacobson |
| 2013/0244884 A1 | 9/2013 | Jacobson et al. |
| 2013/0252849 A1 | 9/2013 | Hudson et al. |
| 2013/0281308 A1 | 10/2013 | Kung et al. |
| 2013/0296192 A1 | 11/2013 | Jacobson et al. |
| 2013/0296194 A1 | 11/2013 | Jacobson et al. |
| 2013/0309725 A1 | 11/2013 | Jacobson et al. |
| 2014/0141982 A1 | 5/2014 | Jacobson et al. |
| 2014/0309119 A1 | 10/2014 | Jacobson et al. |
| 2015/0065393 A1 | 3/2015 | Jacobson |
| 2016/0144332 A1 | 5/2016 | Chu |

FOREIGN PATENT DOCUMENTS

| | | |
|---|---|---|
| EP | 1159285 A1 | 12/2001 |
| EP | 1180548 A2 | 2/2002 |
| EP | 1 205 548 | 5/2002 |
| EP | 1205548 A1 | 5/2002 |
| WO | WO 1990/00626 | 1/1990 |
| WO | WO-9000626 A1 | 1/1990 |
| WO | WO-9317126 A1 | 9/1993 |
| WO | WO1993/20092 | 10/1993 |
| WO | WO-9320092 A1 | 10/1993 |
| WO | WO-9418226 A1 | 8/1994 |
| WO | WO-9735957 A1 | 10/1997 |
| WO | WO-9805765 A1 | 2/1998 |
| WO | WO-9820020 A2 | 5/1998 |
| WO | WO-9838326 A1 | 9/1998 |
| WO | WO-9919341 A1 | 4/1999 |
| WO | WO-9925724 A2 | 5/1999 |
| WO | WO 1999/042813 | 8/1999 |
| WO | WO-9942813 A1 | 8/1999 |
| WO | WO-0029616 A1 | 5/2000 |
| WO | WO-0040715 A2 | 7/2000 |
| WO | WO-0046386 A2 | 8/2000 |
| WO | WO-0049142 A1 | 8/2000 |
| WO | WO 2001/88173 | 11/2001 |
| WO | WO-0188173 A2 | 11/2001 |
| WO | WO-0204597 A2 | 1/2002 |
| WO | WO 2002/024597 | 3/2002 |
| WO | WO-0224597 A2 | 3/2002 |
| WO | WO-02081490 A2 | 10/2002 |
| WO | WO-02095073 A1 | 11/2002 |
| WO | WO-02101004 A2 | 12/2002 |
| WO | WO-03010311 A2 | 2/2003 |
| WO | WO-03033718 A1 | 4/2003 |
| WO | WO 2003/040410 | 5/2003 |

(56) References Cited

FOREIGN PATENT DOCUMENTS

| | | |
|---|---|---|
| WO | WO-03040410 A1 | 5/2003 |
| WO | WO 2003/046223 | 6/2003 |
| WO | WO-03046223 A1 | 6/2003 |
| WO | WO-03054232 A2 | 7/2003 |
| WO | WO-03060084 A2 | 7/2003 |
| WO | WO 2003/064026 | 8/2003 |
| WO | WO 2003/064027 | 8/2003 |
| WO | WO 2003/064699 | 8/2003 |
| WO | WO 2003/065038 | 8/2003 |
| WO | WO 2003/066212 | 8/2003 |
| WO | WO-03064026 A1 | 8/2003 |
| WO | WO-03064027 A2 | 8/2003 |
| WO | WO-03064611 A2 | 8/2003 |
| WO | WO-03064699 A2 | 8/2003 |
| WO | WO-03065038 A2 | 8/2003 |
| WO | WO-03066212 A2 | 8/2003 |
| WO | WO 2003/100012 | 12/2003 |
| WO | WO-03100012 A2 | 12/2003 |
| WO | WO 2004/002627 | 1/2004 |
| WO | WO-2004002627 A2 | 1/2004 |
| WO | WO 2004/024886 | 3/2004 |
| WO | WO-2004024886 A2 | 3/2004 |
| WO | WO 2004/029586 | 4/2004 |
| WO | WO 2004/031351 | 4/2004 |
| WO | WO 2004/031399 | 4/2004 |
| WO | WO-2004029586 A1 | 4/2004 |
| WO | WO-2004031351 A2 | 4/2004 |
| WO | WO-2004031399 A2 | 4/2004 |
| WO | WO-2004034028 A2 | 4/2004 |
| WO | WO 2004/090170 | 10/2004 |
| WO | WO-2004090170 A1 | 10/2004 |
| WO | WO 2005/059096 | 6/2005 |
| WO | WO-2005059096 A2 | 6/2005 |
| WO | WO-2005071077 A1 | 8/2005 |
| WO | WO-2005089110 A2 | 9/2005 |
| WO | WO-2005107939 A1 | 11/2005 |
| WO | WO 2005/123956 | 12/2005 |
| WO | WO-2005123956 A2 | 12/2005 |
| WO | WO 2006/044956 | 4/2006 |
| WO | WO-2006044956 A1 | 4/2006 |
| WO | WO-2006049843 A1 | 5/2006 |
| WO | WO 2006/076679 | 7/2006 |
| WO | WO-2006076679 A1 | 7/2006 |
| WO | WO-2006127423 A2 | 11/2006 |
| WO | WO-2007008951 A1 | 1/2007 |
| WO | WO-2007009082 A1 | 1/2007 |
| WO | WO 2003/054232 | 7/2007 |
| WO | WO-2007075438 A2 | 7/2007 |
| WO | WO-2007087347 A2 | 8/2007 |
| WO | WO-2007113688 A2 | 10/2007 |
| WO | WO-2007117396 A1 | 10/2007 |
| WO | WO-2007120624 A2 | 10/2007 |
| WO | WO2007/136736 | 11/2007 |
| WO | WO-2007123742 A2 | 11/2007 |
| WO | WO-2007136736 A2 | 11/2007 |
| WO | WO-2007136833 A2 | 11/2007 |
| WO | WO-2007136834 A2 | 11/2007 |
| WO | WO-2007136835 A2 | 11/2007 |
| WO | WO-2007136840 A2 | 11/2007 |
| WO | WO 2008/024319 | 2/2008 |
| WO | WO-2008024319 A2 | 2/2008 |
| WO | WO-2008045380 A2 | 4/2008 |
| WO | WO-2008054543 A2 | 5/2008 |
| WO | WO-2008076368 A2 | 6/2008 |
| WO | WO 2008109176 A2 * | 9/2008 |
| WO | WO-2008130629 A2 | 10/2008 |
| WO | WO 2010/025310 | 3/2010 |
| WO | WO 2010025310 A2 * | 3/2010 |
| WO | WO 2011/066185 | 3/2011 |
| WO | WO 2011/056872 | 5/2011 |
| WO | WO 2011/066186 | 5/2011 |
| WO | WO-2011056872 A2 | 5/2011 |
| WO | WO-2011066185 A1 | 6/2011 |
| WO | WO-2011066186 A1 | 6/2011 |
| WO | WO-2011085075 A2 | 7/2011 |
| WO | WO-2012064975 A1 | 5/2012 |
| WO | WO-2012174337 A1 | 12/2012 |
| WO | WO-2013/032850 A2 | 3/2013 |
| WO | WO-2013163263 A2 | 10/2013 |
| WO | WO-2014004393 A1 | 1/2014 |
| WO | WO-2014/151696 A1 | 9/2014 |
| WO | WO-2014160004 A1 | 10/2014 |
| WO | WO-2014160059 A1 | 10/2014 |

OTHER PUBLICATIONS

Chemical Book, 612-25-9 (2-Nitrobenzyl Alcohol) Product Description, 2007, 1-2.*
LookChem, D-Biotin, 2008, 1-2.*
Sigma, Product Information, Dimethyl Sulfoxide, 2002, 1-2.*
Tufts School of Engineering, EN43ME Lecture Notes, Gourmet Engineering, 2010, 1-3.*
ScienceLab.com, Mineral Oil, Material Safety Data Sheet, 2005, 1-5.*
The Good Scents Company, Polyglycerol Polyricinoleate, 1980, 1-2.*
Fingas et al., Studies of Water-In-Oil Emulsions: Stability Studies, Proceedings of the Twenthieth Arctic Marine Oilspill Program Technical Seminar, 1997, 1-22.*
McClements, D., Critical Review of Techniques and Methodologies for Characterization of Emulsion Stability, Critical Reveiws in Food Science and Nutrition, 2007, 47(7), 611-649.*
Freitas et al., Microencapsulation by Solvent Extraction/Evaporation: Reviewing the State of the Art of Microsphere Preparation Process Technology, Journal of Controlled Release, 2005, 102, 313-332.*
Margulies et al., Genome Sequencing in Microfabricated High-Density Picolitre Reactors, Nature, 2005, 437, 376-380.*
Margulies et al., Supplemental Methods, Nature, 2005, 437, 1-34.*
Rodrigue et al., Whole Genome Amplification and De Novo Assembly of Single Bacterial Cells, PLoS One, 2009, 4(9), 1-10.*
Sadtler et al., Achieving Stable, Reverse Water-in-Fluorocarbon Emulsions, Angew. Chem. Int. Ed. Engl., 1996, 35(17), 1976-1978.*
Van Hassel et al., Advancement of Systems Designs and Key Engineering Technologies for Materials-Based Hydrogen Storage, FY 2014 Annual Progress Report, Doe Hydrogen and Fuel Cells Program, 2014, 36-42.*
Macierzanka et al., Phase Transitions and Microstructure of Emulsion Systems Prepared with Acylglycerols/Zinc Stearate Emulsifier, Langmuir, 2006, 22, 2487-2497. (Year: 2006).*
Adessi, C., et al. "Solid phase DNA amplification: characterization of primer attachment and amplification mechanisms," Nucleic Acids Research, 28(20):e87 (8 pages), (2000).
Ashkin, A., "Applications of laser radiation pressure" Science, 210(4474): 1081-1088, (Dec. 5, 1980).
Bar G., et al., "Dendrimer-modified silicon oxide surfaces as platforms for the deposition of gold and silver colloid monolayers: preparation method, characterization, and correlation between microstructure and optical properties," Langmuir, 12(5):1172-1179, (Mar. 6, 1996).
Beer, N., et al., "On-chip, real time single-copy polymerase chain reaction in picoliter droplets," Analytical Chemistry, 79(22):8471-8475, (Nov. 15, 2007).
Bennett, S., "Solexa Ltd.," Pharmacogenomics, 5(4):433-8, (Jun. 2004).
Berthier, E., et al. "Managing evaporation for more robust microscale assays. Part 1: Volume loss in high throughput assays Supplementary Information," Lab Chip, 8:852-859, (Feb. 29, 2008).
Bethell, D., et al. "From monolayers to nanostructured materials: an organic chemist's view of self-assembly," J. Electroanal. Chem., 409:137-143, (1996).
Binkowski, B., et al. "Correcting errors in synthetic DNA through consensus shuffling," Nucleic Acids Research, 33(6):1-8, (2005).
Biswas, I. and Hsieh, P., "Identification and characterization of a thermostable MutS homolog from Thermus aquaticus,." J. Biol. Chem, 271(9):5040-5048, (1996).

(56) References Cited

OTHER PUBLICATIONS

Blanchard, A., "Synthetic DNA Arrays," Genetic Engineering, 20:111-123, Plenum Press, (1998).
Boal, J., et al., "Cleavage of oligodeoxyribonucleotides from controlled-pore glass supports and their rapid deprotection by gaseous amines," NAR, 24(15):3115-3117, (1996).
Carr, P., et al., "Protein-mediated error correction for de novo DNA synthesis," Nucleic Acids Res., 32(20):e162 (9 pages), (2004).
Cho, S., et al. "Creating, transporting, cutting and merging liquid droplets by electrowetting-based actuation for digital microfluidic circuits," J. of Microelectromechanical Systems, 12(1):70-80, (Feb. 2003).
Cleary, M., et al. "Production of complex nucleic acid libraries using highly parallel in situ oligonucleotide synthesis," Nat Methods., 1(3):241-248, (Dec. 2004).
Colvin, V., et al. "Semiconductor nanocrystals covalently bound to metal surfaces with self-assembled monolayers," J. Am. Chem. Soc., 114(13):5221-5230, 1992.
Duggan, D., et al., "Expression profiling using cDNA microarrays," Nat. Genet., 21:10-14 (Jan. 1999).
Fair, R., "Digital microfluidics: is a true lab-on-a-chip possible?" Microfluid Nonofluid, 3:245-281, (2007).
Fidalgo, L., et al., "Surface induced droplet fusion in microfluidic devices," Lab on Chip, 7(8)984-986, (2007).
Fodor, S., et al. "Light-directed, spatially addressable parallel chemical synthesis," Science, 251(4995):767-773, (Feb. 15, 1991).
Golz, S. and Kemper, B., "Enzymatic mutation detection: enrichment of heteroduplexes from hybrid DNA mixtures by cleavage-deficient GST-tagged endonuclease VII," Nucleic Acids Res., 27(15):e7 (4 pages), (Aug. 1, 1999).
Grabar, K., et al., "Preparation and Characterization Monolayers," Anal. Chem., 67:735-743, (1995).
Greenberg, M., et al., "Cleavage of oligonucleotides from solid-phase support using o-nitrobenzyl photochemistry," J. of Org. Chem., 59(4):746-753, (Feb. 1994).
Griffith E. and Aklella, S., "Coordinating Multiple droplets in Planar Array Digital Microfluidics Systems," The International Journal of Robotics Research, 24(11):933-949, (Nov. 2005).
Gulati, S., et al., "Opportunities for microfluidic technologies in synthetic biology," J.R.Soc. Interface, 6: S493-S506, (2009).
Haeberle S. et al. "Microfluidic platforms for lab-on-chip applications," Lab on a Chip, 7(9):1094-1110, (2007).
Hardy, P., et al., "Reagents for the preparation of two oligonucleotides per synthesis (TOPS™)," Nucleic Acids Research, 22(15):2998-3004, (1994).
Holmes, C., et al., "Model studies for new o-nitrobenzyl photolabile linkers: substituent effects on the rates of photochemical cleavage," J. of Org. Chem., 62(8):2370-2380, (Apr. 18, 1997).
Hyman, E., "A new method of sequencing DNA," Analytical Biochemistry, 174(2):423-436, (Nov. 1, 1988).
Kahl, J., et al., "High-Yielding Method for On-Column Derivatization of Protected Oligodeoxy-nucleotides and Its Application to the Convergent Synthesis of 5',3'-Bis-conjugates," J. of Org. Chem., 63(15):4870-4871, (Jul. 8, 1998).
Kahl, J., and Greenberg, M., "Solution-Phase Bioconjugate Synthesis Using Protected Oligonucleotides Containing 3'-Alkyl Carboxylic Acids," J. of Org. Chem., 64(2):507-510, (1999).
Kelly, B., et al., "Miniaturizing chemistry and biology in microdroplets," Chem. Commun., 1773-1788, (2007).
Kong, D., et al., "Parallel gene synthesis in a microfluidic device," Nucleic Acids Research, 35(8):1-9, (2007).
Leamon, J., et al., "A massively parallel PicoTiterPlate™ based platform for discrete picoliter-scale polymerase chain reactions," Electrophoresis, 24(21):3769-3777, (Nov. 2003).
Liu, Y., et al., "DNA ligation of ultramicrovolume using EWOD microfluidic system with coplanar electrodes: DNA ligation of ultramicrovolume using a EWOD microfluidic system," J. of Micromechanics and Microengineering, 18(4):45017 (7 pages), (2008).

Margulies, M., et al., "Genome sequencing in microfabricated high-density picolitre reactors," Nature, 437(7057):376-380, (Sep. 15, 2005).
McGall, G., et al., "Light-directed synthesis of high-density oligonucleotide arrays using semiconductor photoresists," PNAS, 93(24):13555-13560, (Nov. 26, 1996).
Metzker, M., et al., "Termination of DNA synthesis by novel 3'-modifieddeoxyribonucleoside 5'-triphosphates," NAR, 22(20):4259-4267, (1994).
Mitra, R., et al., "Fluorescent in situ sequencing on polymerase colonies," Analytical Biochemistry, 320:55-65, (2003).
Oleykowski, C., et al., "Mutation detection using a novel plant endonuclease," Nucleic Acids Res., 26(20):4597-4602, (Oct. 15, 1998).
Pon., R., "Solid-phase supports for oligonucleotide synthesis," Methods Mol. Biol. 20:465-496, (1993).
Richmond, K., et al., "Amplification and assembly of chip-eluted DNA (AACED): a method for high-throughput gene synthesis," Nucleic Acids Res., 32(17):5011-5018, (2004).
Schaerli, Y., et al., "Continuous-Flow polymerase Chain reaction of single-copy DNA Micorfluidic Microdroplets," Anal. Chem., 81:302-306, (2009).
Seo, T., et al.,"Four-color DNA sequencing by synthesis on a chip using photocleavable fluorescent nucleotides," PNAS, 102(17):5926-5933, (Apr. 26, 2005).
Shabarova, Z., et al. "Chemical ligation of DNA: the first non-enzymatic assembly of a biologically active gene," Nucl. Acids Res., 19(15):4247-4251, (1991).
Shendure, J., et al., "Accurate Multiplex Polony Sequencing of an Evolved Bacterial Genome," Science, 309:1728-1732, (Sep. 9, 2005).
Stekel, D., "Microarrays: Making Them and Using Them in Microarray Bioinformatics," Cambridge University Press, (10 pages), 2003.
Teh, S-Y, et al., "Droplet microfluidics," Lab on Chip, 8(2), (2008).
Tian, J. et al., "Accurate multiplex gene synthesis from programmable DNA microchips," Nature, 432:1050-1054, (Dec. 2004).
Verma, S. and Eckstein, F., et al., "Modified oligonucleotides: Synthesis and Strategy for Users," Annu. Rev. Biochem., 67:99-134, (1998).
Xu, Y. and Kool, E., et al., "A Novel 5'-Iodonucleoside allows efficient nonenzymatic ligation of single-stranded and duplex DNAs," Tetrahedron Lett., 38(32): 5595-5598, (Aug. 11, 1997).
Xu, Y. and Kool, E., et al., "High sequence fidelity in a non-enzymatic DNA autoligation reaction," Nuc. Acids Res., 27(3): 875-881, (1999).
Xu, Y., et al., "Nonenzymatic autoligation in direct three-color detection of RNA and DNA point mutations," Nat. Biotech., 19:148-152, (Feb. 2001).
Zhang, C., et al., "PCR microfluidic devices for DNA amplification," Biotechnology Advances, 24(3):243-284, 2006.
Zhou X. et al. "Microfluidic PicoArray synthesis of oligodeoxynucleotides and simultaneous assembling of multiple DNA sequences" Nucleic Acids Research, 2004, vol. 32, No. 18, pp. 5409-5417.
Zielke, P. and Szymczyk, J., "Experimental investigation of the motion and deformation of droplets on surfaces with a linear wettability gradient," Eur. Phys. J. Special Topics, 166:155-158, (Jan. 2009).
International Search report for International Patent Application No. PCT/US2010/055298 dated Sep. 7, 2011.
Afshari et al. "Application of Complementary DNA Microarray Technology to Carcinogen Identification, Toxicology, and Drug Safety". Cancer Research, 59, 4759-4760, Oct. 1, 1999.
Akhundova A.A. et al. "RNA synthesis on immobilized DNA templates in vitro." Biochemistry—Moscow, 43(5):626-628 (1978).
Altschul, S. & Koon in, E. "Iterated profile searches with PSI-BLAST—a tool for discovery in protein databases," Trends Biochem. Sci., 23:444-447, (1998).
Altschul, S., et al. "Basic local alignment search tool," J Mol Biol., 215(3):403-10, (1990).

(56) References Cited

OTHER PUBLICATIONS

Andersen, J., et al. "New Unstable Variants of Green Fluorescent Protein for Studies of Transient Gene Expression in Bacteria," Applied and Environmental Microbiology, 64(6):2240-2246 (Jun. 1998).
Angell, et al., "Silicon Micromechanical Devices", Scientific American, 28:44-55 (1983).
Beier M. and Hohseil J.D. "Analysis of DNA-microarray produced by inverse in situ oligonucleotide synthesis." J. Biotechnology, 94:15-22 (2002).
Booth, P.M., et al. "Assembly and cloning of coding sequences for neurotrophic factors directly from genomic DNA using polymerase chain reaction and uracil DNA glycosylase," Gene 146:303-308 (1994).
Brown, Chappell "BioBricks to help reverse-engineer life," http://www.eetimes.com/General/displayPrintViewContent?contentItemId=4049-196, Jun. 11, 2004.
Caruthers et al., "CXV. Total synthesis of the structural gene for an alanine transfer RNA from yeast. Enzymic joining to form the total DNA duplex," J Mol Biol., 72(2):475-92, (Dec. 28, 1972).
Chalmers, F.P., et al. "Scaling Up the Ligase Chain Reaction-Based Approach to Gene Synthesis" BioTechniques 30:249-252 (2001).
Chan, L. et al. "Refactoring bacteriophage T7," Molecular Systems Biol., doi: 10.1038/msb4100025, (Published online Sep. 13, 2005).
Chang, C., et al. "Evolution of a cytokine using DNA family shuffling," Nature Biotechnology, 17: 793-797(1999).
Che, A. "BioBricks++: Simplifying Assembly of Standard DNA Components," [Online] XP002412778, URL:http://austinche.name/docs/bbpp.pdf (Jun. 9, 2004).
Chen, H.B., et al. "A new method for the synthesis of a structural gene," Nucleic Acids Research 18(4):871-878 (1990).
Cherepanov A "Joining of short DNA oligonucleotides with base pair mismatches by T4 DNA ligase" J Biochem. Jan. 2001;129(1):61-8.
Christians, F., et al. "Directed evolution of thymidine kinase for AZT phosphorylation using DNA family shuffling," Nature Biotechnology, 17:259-264(1999).
Coco, W., et al. "Growth Factor Engineering by Degenerate Homoduplex Gene Family Recombination," Nature Biotechnology, 20: 1246-1250, (Dec. 2002).
Crameri, A, et al. "DNA shuffling of a family of genes from diverse species accelerates directed evolution," Nature, 391:288-291(1998).
Crameri, A, et al. "Improved Green Fluorescent Protein by Molecular Evolution Using DNA Shuffling," Nature Biotechnology, vol. 14, Mar. 1996, pp. 315-319.
Crameri, A, et al. "Molecular evolution of an arsenate detoxification pathway by DNA shuffling," Nature Biotechnology, 15:436-438 (1997).
Cui T. et al. "Sepharose-supported DNA as template for RNA synthesis" J. Biotechnology, 66: 225-228 (1998).
Dafhnis-Calas, F., et al. "Iterative in vivo assembly of large and complex transgenes by combining the activities of DC31 integrase and Cre recombinase," Nucleic Acids Research, 33(22): 1-14 (2005).
Engler C. et al. "A one pot, one step, precision cloning method with high throughput capability" PLoS One, 3: e36471, 2008.
Engler C. et al. "Golden Gate Shuffling: a one-pot DNA shuffling method based on type IIS restriction enzymes" PLoS One, 4:e5553, 2009.
Evans, E. & Alani, E. "Roles for Mismatch Repair Factors in Regulating Genetic Recombination," Molecular & Cellular Biology, 20(21):7839-7844 (Nov. 2000).
Ferretti, L. et al. "Total synthesis of a gene for bovine rhodopsin," PNAS, 83:599-603 (Feb. 1986).
Ferrin, L.J., et al. "Sequence-specific ligation of DNA using RecA protein," Proc. Natl. Acad. Sci. USA, 95: 2152-2157 (1998).
Fisch, I. et al. "A Strategy of Exon Shuffling for Making Large Peptide Repertoires Displayed on Filamentous Bacteriophage," Proceedings of the National Academy of Sciences of USA, 93:7761-7766, (Jul. 1996).
Fleck, O. & Nielsen O. "DNA Repair," J. Cell Science, 117:515-517 (2004).
Gao, X. et al. "Thermodynamically balanced inside-out (TBIO) PCR-based gene synthesis: a novel method of primer design for high fidelity assembly of longer gene sequences," Nucleic Acids Research, 31(22):e143 (11 pages) (2003).
Gardner, T., et al. "Construction of a genetic toggle switch in *Escherichia coli*," Nature, 403:339-342 (Jan. 2000).
Gibbs, W. "Synthetic Life," Scientific American, [Online] URL: htto://www.sciam.com/orint version.cfm?articleID=0009FCA4, (Apr. 26, 2004).
Goler, J. "BioJADE: A Design and Simulation Tool for Synthetic Biological Systems," MIT Computer Science and Artificial Intelligence Laboratory, AI Technical Report, [Online] URL:http://dspace.mit.edu/bitstream/1721.1/30475/2/MIT-CSAIL-TR-2004-036.pdf, (May 2004).
Gu et al., "Single Molecule Sensing by Nanopores and Nanopore Devices", Analysts, vol. 135, No. 3, pp. 441-451, (published online Dec. 2009).
Guntas, G., et al. "A molecular switch created by in vitro recombination of nonhomologous genes," Chem. & Biol., 11: 1483-1487 (Nov. 2004).
Guntas, G., et al. "Directed Evolution of Protein Switches and Their Application to the Creation of Ligand-Binding Proteins," Proc. Natl. Acad. Sci. USA, 102(32):11224-11229 (Aug. 9, 2005).
Hacia J.G. "Resequencing and mutational analysis using oligonucleotide microarrays", Nature Genetics, 21(1 suppl):42-47, 1999.
Hacia J.G. et al. "Applications of DNA chips for genomic analysis". Mol Psychiatry. Nov. 1998;3(6):483-92.
Hecker, K. "Error Analysis of Chemically Synthesized Polynucleotides," BioTechniques, 24(2):256-260, (Feb. 1998).
Heeb, S., et al. "Small, Stable Shuttle Vectors Based on the Minimal pVS1 Replicon for Use in Gram-Negative Plant-Associated Bacteria," MPMI, 13(2):232-237 (2000).
International Preliminary Report on Patentability for International Patent Application PCT/US2010/057392 dated Jun. 7, 2012.
International Search Report for International Patent Application PCT/US2010/057392 dated Feb. 16, 2011.
International Search Report for International Patent Application PCT/US2011/020335 dated Jul. 19, 2011.
Jayaraman K. et al. "Polymerase chain reaction-mediated gene synthesis: synthesis of a gene coding for isozyme c of horseradish peroxidase." Proc Natl Acad Sci USA. May 15, 1991; 88(10): 4084-4088.
Johnston M. "Gene chips: Array of hope for understanding gene regulation". Current Biology, 8: (5) R171, 1998.
Jones, T., et al. "The Development of a Modified Human IFN-alpha2b Linked to the Fe Portion of Human IgG1 as a Novel Potential Therapeutic for the Treatment of Hepatitis C Virus Infection," Journal of Interferon & Cytokine Research, 24:560-572,(2004).
Kampke T. "Efficient primer design algorithms" Bioinformatics, 2001, vol. 17, No. 3, pp. 214-225.
Kim J.H. et al. "Solid-phase genetic engineering with DNA immobilized on a gold surface." J. Biotechnology, 96:213-22 (2002).
Kim, C., et al. "Biological lithography: Improvements in DNA synthesis methods," J. Vac. Sci. Technol. B 22(6):3163-3167 (2004).
Kim, Y., et al. "Insertion and Deletion Mutants of FokI Restriction Endonuclease," J. Biol. Chem., 269(50):31978-31982 (1994).
Kitamura, K., et al. "Construction of Block-Shuffled Libraries of DNA for Evolutionary Protein Engineering: Y-Ligation-Based Block Shuffling." Protein Engineering, 15(10): 843-853, (Oct. 2002).
Kleppe K., et al. "Studies of polynucleotides: repair replication of short synthetic DNA's as catalyzed by DNA polymerases," J. Mol. Biol. 56:341-361, (1971).
Kodumal et al., "Total synthesis of long DNA sequences: Synthesis of a contiguous 32-kb polyketide synthase gene cluster," PNAS, 101(44):15573-15578, (Nov. 2, 2004).--15578.
Kolisnychenko, V., et al. "Engineering a Reduced *Escherichia coli* Genome," Genome Research, 12:640-647, (2002).

(56) References Cited

OTHER PUBLICATIONS

Kotsopoulou, E., et al. "A Rev-Independent Human Immunodeficiency Virus Type 1 (HIV-1)-Based Vector That Exploits a Codon-Optimized HIV-1 gag-pol Gene," Journal of Virology, 74(10):4839-4852, (May 2000).
Kowalczykowski, S. "In vitro reconstitution of homologous recombination reactions," Experientia, 50:204-215, (1994).
Kowalczykowski, S. "Initiation of genetic recombination and recombination-dependent replication," TIBS, 25:156-165, (Apr. 2000).
Krieg A "Real-time detection of nucleotide incorporation during complementary DNA strand analysis" Chem. Bio. Chem. 4:589-592 (2003).
Kurian et al. "DNA chip technology". J Pathol.; 187(3):267-71, (Feb. 1999).
Lamers, M., et al. "ATP Increases the Affinity between MutS ATPase Domains," J. Biol. Chem., 279(42):43879-43885, (Oct. 15, 2004).
Lashkari et al. "An automated multiplex oligonucleotide synthesizer: Development of high throughput, low cost DNA synthesis". PNAS 92(17): 7912-7915, (1995).
Lebedenko E.N. et al. "Method of artificial DNA splicing by directed ligation" Nucleic Acids Research, 19: 6757-6761, 1991.
Lee, K., et al. "Genetic approaches to Studying Protein Synthesis: Effects of Mutations at .PSI.1516 and A535 in Escherichia coli 16S rRNA," J. Nutr., 131:2994S-3004S, (2001).
Lewis, J. & Hatfull, G. "Control of directionality in intergrase-mediated recombination: examination of recombination directionality factors (RDFs) including Xis and Cox proteins," Nucl. Acids Res., 29(11):2205-2216 (2001).
Li L et al. "Alteration of the cleavage distance of Fok I restriction endonuclease by insertion mutagenesis." Proc Natl Acad Sci USA. 90(7): 2764-2768 (Apr. 1993).
Li, C., and Evans, R. "Ligation independent cloning irrespective of restriction site compatibility," Nucl. Acids Res., 25(20):4165-4166 (1997).
Link, A., et al. "Methods for generating precise deletions and insertions in the genome of wild-type Escherichia coli: Application to open reading frame characterization," J. Bacteriol., 179(20):6228-6237, (Oct. 1997).
Liu G. et al. "DNA computing on surfaces." Nature, 403:175179 (2000).
Luo, P., et al. "Development of a Cytokine Analog with Enhanced Stability Using Computational Ultrahigh Throughput Screening," Protein Science, 11:1218-1226, (2002).
Lutz, S. & Benkovic, J. "Homology-Independent Protein Engineering," Current Opinion in Biotechnology, 11:319-324, (2000).
Mandecki W. "Oligonucleotide-directed double-strand break repair in plasmids of Escherichia coli: A method for site-specific mutagenesis." 1986, PNAS, 83:7177-7181.
Markham, N. R. & Zuker, M., "DINAMelt web server for nucleic acid melting prediction", Nucleic Acids Res., 33, W577-W581, (2005.).
Miick, S., et al. "Crossover isomer bias is the primary sequence-dependent property of immobilized Holliday junctions," Proc. Natl. Acad. Sci. USA, 94:9080-9084, (Aug. 1997).
Milton, R., et al. "Total Chemical Synthesis of a D-Enzyme: The Enantiomers of HIV-1 Protease Show Demonstration of Reciprocal Chiral Substrate Specificity," Science, 256:1445-1448, (Jun. 5, 1992).
Mir K. U. et al. "Sequencing by cyclic ligation and cleavage (CycLic) directly on a microarray captured template". Nucl. Acids Rse. vol. 37, No. 1 e5, 2008.
Modrich, P. "Strand-specific Mismatch Repair in Mammalian Cells," J. Biol. Chem., 272(40): 24727-24730, (Oct. 3, 1997).
Moore, G. & Maranas C. "Computational Challenges in Combinatorial Library Design for Protein Engineering," AIChE Journal, 50(2):262-272, (Feb. 2004).
Morton, Oliver "Life, Reinvented," Wired, http:www.wired.com/wired/archive!13.01/mit.sub.--pr.html (2005).

Nakamaye, K., et al. "Direct sequencing of polymerase chain reaction amplified DNA fragments through the incorporation of deoxynucleoside alpha-thiotriphosphates," Nucleic Acids Research, 16(21):9947-9959, (1988).
Ness, J., et al. "DNA shuffling of subgenomic sequences of subtilisin," Nature Biotechnology 17: 893-896 (1999).
Ness, J., et al. "Synthetic Shuffling Expands Functional Protein Diversity by Allowing Amino Acids to Recombine Independently" Nature Biotechnology, 20:1251-1255, (Dec. 2002).
Nilsson P. et al. "Real-Time monitoring of DNA manipulations using biosensor technology" Analytical Biochemistry, 1995, 224:400-408.
Noirot, P. & Kolodner, R. "DNA Strand Invasion Promoted by Escherichia coli RecT Protein," J. Biol. Chemn., 273(20):12274-12280, (May 15, 1998).
Novy, R., et al. "Ligation Independent Cloning: Efficient Directional Cloning of PCR Products," Novagen, Inc., InNovations, 5: 1-3, http://www.emdbiosciences.com/html/NVG/inNovations.html), (1966).
Panet A. and Khorana G.H. "Studies of polynucleotides: the linkage of deoxyribopolynucleotides templates to cellulose and its use in their replication." J. Biol. Chem. 249(16):5213-5221 (1974).
Parr, R. & Ball, J. "New donor vector for generation of histidine-tagged fusion proteins using the Gateway Cloning System," Plasmid, 49:179-183, (2003).
Peters, J. & Craig, N. "Tn7: Smarter Than We Thought," Nature, 2:806-814, (Nov. 2001).
Posfai, G., et al. "In vivo excision and amplification of large segments of the Escherichia coli genome," Nucl. Acids Res., 22(12):2392-2398, (1994).
Posfai, G., et al. "Markerless gene replacement in Escherichia coli stimulated by a double-strand break in the chromosome," Nucl. Acids Res., 27(22):4409-4415, (1999).
Regalado, A. "Next Dream for Venter: Create Entire Set of Genes From Scratch," Wall Street Journal, A1, (Jun. 29, 2005).
Rouwendal, G., et al. "Enhanced Expression in Tobacco of the Gene Encoding Green Fluorescent Protein by Modification of its Codon Usage," Plant Molecular Biology, 33:989-999, (1997).
Ryu, D.D.Y., et al. "Recent Progress in Biomolecular Engineering," Biotechnol. Prog. 16: 2-16 (2000).
Sa-Ardyen, P., et al. "The flexibility of DNA double crossover molecules," Biophys. J., 84:3829-3837, (Jun. 2003).
Saiki, R., et al. "Analysis of enzymatically amplified beta-globin and HLA-DQ alpha DNA with allele-specific oligonucleotide probes," Nature, 324(6093):163-166, (Nov. 13, 1986).
Sakabe, N., et al. "A Bioinformatics Analysis of Alternative Exon Usage in Human Genes Coding for Extracellular Matrix Proteins," Genetics and Molecular Research, 3(4):532-544, (2004).
Saks, M. "Making sense out of nonsense," PNAS, 98(5): 2125-2127, (Feb. 27, 2001).
Sato, T., et al. "Production of menaquinone (vitamin K2)-7 by Bacillus subtilis," J. of Bioscience and Engineering, 91(1):16-20, (2001).
Semizarov, D., et al. "Stereoisomers of Deoxynucleoside 5'-Triphosphates as Substrates for Template-dependent and -independent DNA Polymerases," J. Biol. Chem., 272(14) 9556-9560 (1997).
Sgaramella, V., et al. "Studies of polynucleotides, C.: A novel joining reaction catalyzed by T4-polynucleotide ligase", PNAS, 67(3): 1468-1475, (Nov. 1970).
Shao, Z., et al. "Random-Priming in Vitro Recombination: An Effective Tool for Directed Evolution," Nucleic Acids Research, 26(2):681-683, (1998).
Sieber, V., et al. "Libraries of Hybrid Proteins From Distantly Related Sequences," Nature Biotechnology, 19: 456-460, (May 2001).
Smith, H.O., et al. "Generating a synthetic genome by whole genome assembly:<DX174 bacteriophage from synthetic oligonucleotides," PNAS, 100(26):15440-15445 (2003).
Smith, J. & Modrich, P. "Mutation Detection with MutH, MutL, and MutS Mismatch Repair Proteins," Proc. Natl. Acad. Sci. USA, 93:4374-4379, (Apr. 1996).

(56) References Cited

OTHER PUBLICATIONS

Soderlind et al. "Domain libraries: Synthetic diversity for de novo design of antibody V-regions." Gene, 160 (1995) 269-272.
Stamm et al., "Sanchored PCR: PCR with CDNA Coupled to a solid phase," Nucleic Acids Research, 19(6):1350, (Mar. 25, 1991).
Stemmer et al. "Single-step assembly of a gene and entire plasmid from large numbers of oligodeoxyribonucleotides" Gene 164: 49 (1995).
Strizhov et al. "A synthetic cryiC gene, encoding a Bacillus Thuringiensis delta-endotoxin, confers Spodotera resistance in Alfafa and Tobacco" P.N.A.S., 1996, vol. 93, No. 26, pp. 15012-15017.
Tan, S., et al. "Zinc-finger protein-targeted gene regulation: Genomewide single-gene specificity," PNAS, 100(21):11997-12002, (Oct. 14, 2003).
Tang K. et al. "Chip-based genotyping by mass spectrometry." PNAS, 96:10016-10020 (1999).
Tsutakawa, S. & Morikawa, K. "The Structural Basis of Damaged DNA Recognition and Endonucleolytic Cleavage for Very Short Patch Repair Endonuclease," Nucleic Acids Research, 29(18):3775-3783, (2001).
von Neumann T. "The general and logical theory of automata," Pergamon Press, Taub A.H (Editor) vol. 5, 288-326 (1948).
Weiler and Hoheisel "Combining the Preparation of Oligonucleotide Arrays and Synthesis of High-Qualify Primers." Analytical Biochemistry, vol. 243, Issue 2, Dec. 15, 1996, pp. 218-227.
Wheeler DL "Database resources of the National Center for Biotechnology Information" Nucleic Acids Res. 29(1): 11-6 (Jan. 2001).
Whitesides G.M et al., "Soft Lithography in Biology and Biochemistry," Annual Review of Biomedical Engineering. 3:335-373 (2001).
Wiedmann, M., "Ligase chain reaction (LCR)—overview and applications", 3:S51-S64, http://genome.cshlp.org/content/3/4/S51.refs.html, Copyright 1994 by Cold Spring Harbor Laboratory.
Wilgenbus & Lichter "DNA chip technology ante portas" J. Mol. Med 1999, 77:761-768.
Written Opinion for International Patent Application No. PCT/US2010/057392 dated May 30, 2012.
Written Opinion for PCT/US2010/055298, 11 pages (dated Sep. 7, 2011).
Xia Y. and Whitesides G.M. "Soft lithography" Annual Review of Material Science. 28:153-184 (1998).
Xiong et al. "PCR based accurate synthesis of long DNA sequences" Nature protocols 1 (2): 791 (2006).
Xiong, A., et al. "A simple, rapid, high-fidelity and cost-effective PCR-based two-step DNA synthesis method for long gene sequences," Nucleic Acids Research, 32(12):e98 (10 pages), (2004).
Xuei et al. "Use of SAM(2)(R) biotin capture membrane in microarrayed compound screening (mu ARCS) format for nucleic acid polymerization assays" Journal of Biomolecular Screening 8:273-282 (2003).
Yolov et al. "RNA-synthesis by use of T7-RNA-Polymerase and immobilized DNA in a flowing-type reactor". Bioorganicheskaya Khimiya, 17:789-794 (1991) (English Abstract Only).
Zha, D., et al. "Assembly of Designed Oligonucleotides as an Efficient Method for Gene Recombination: A New Tool in Directed Evolution," ChemBioChem, 4: 34-39, (2003).
Zhao, H., et al. "Molecular Evolution by Staggered Extension Process (Step) In Vitro Recombination," Nature Biotechnology, 16:258-261, (Mar. 1998).

\* cited by examiner

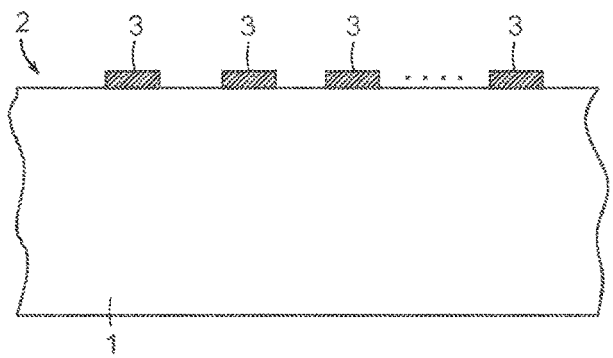
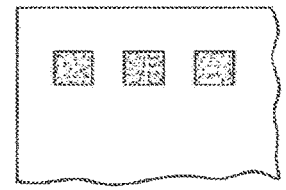
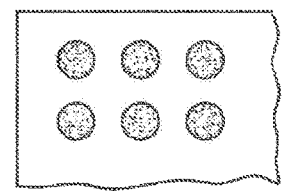
FIG. 1A
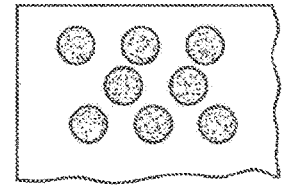
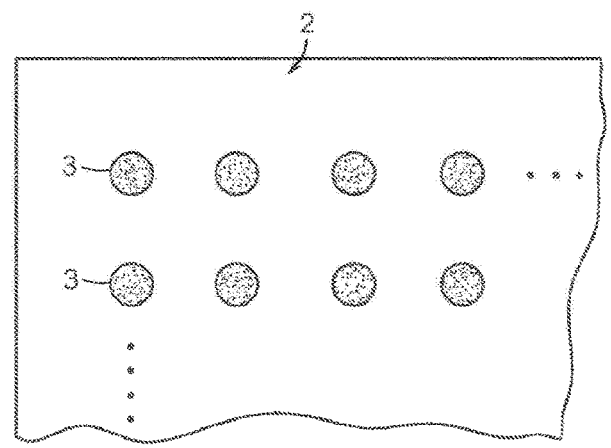
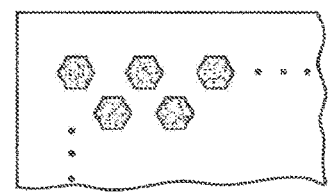
FIG. 1B
FIG. 1C

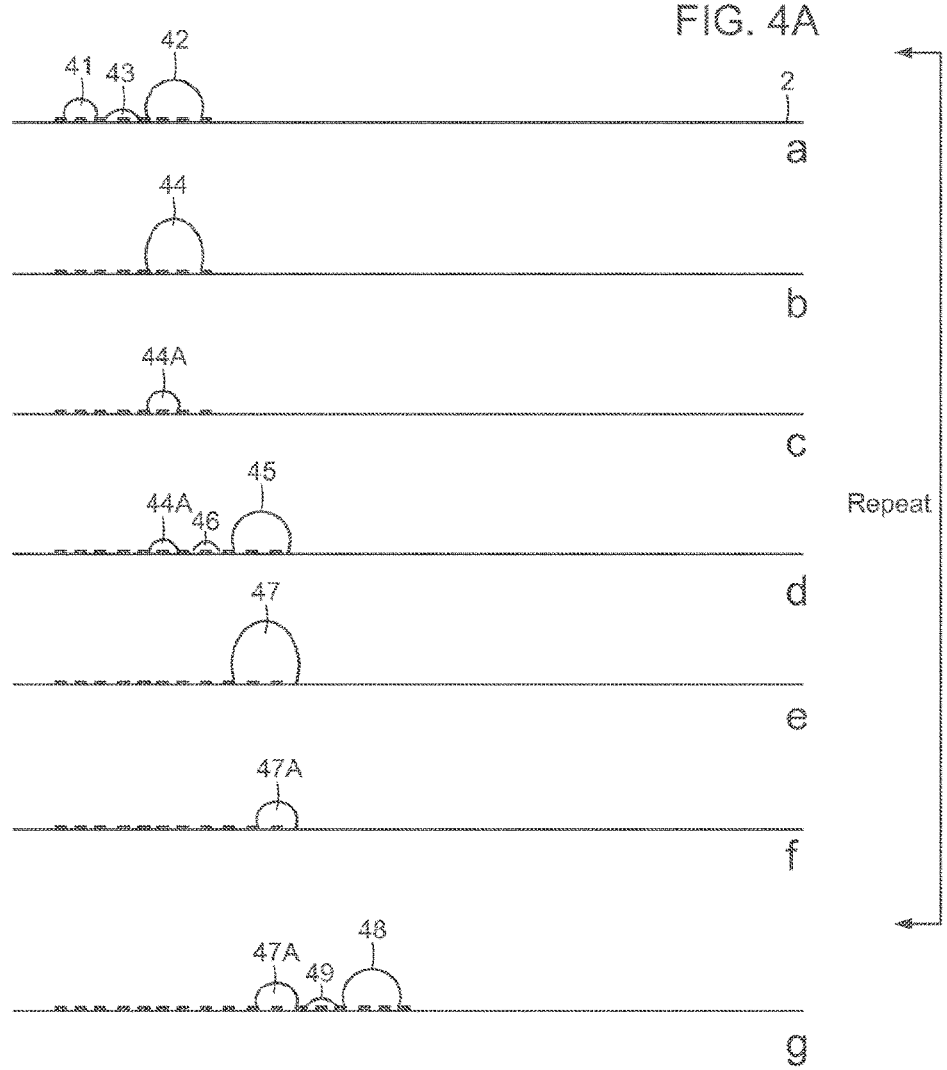

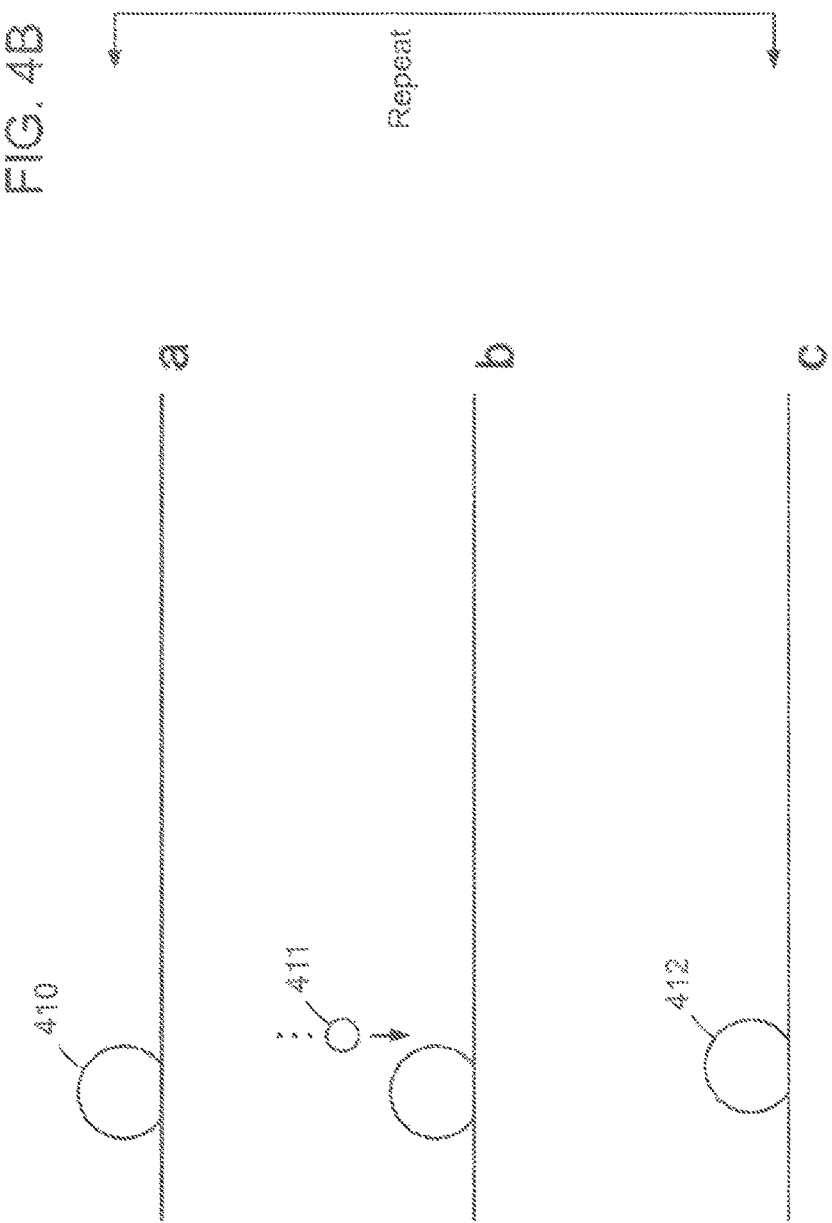

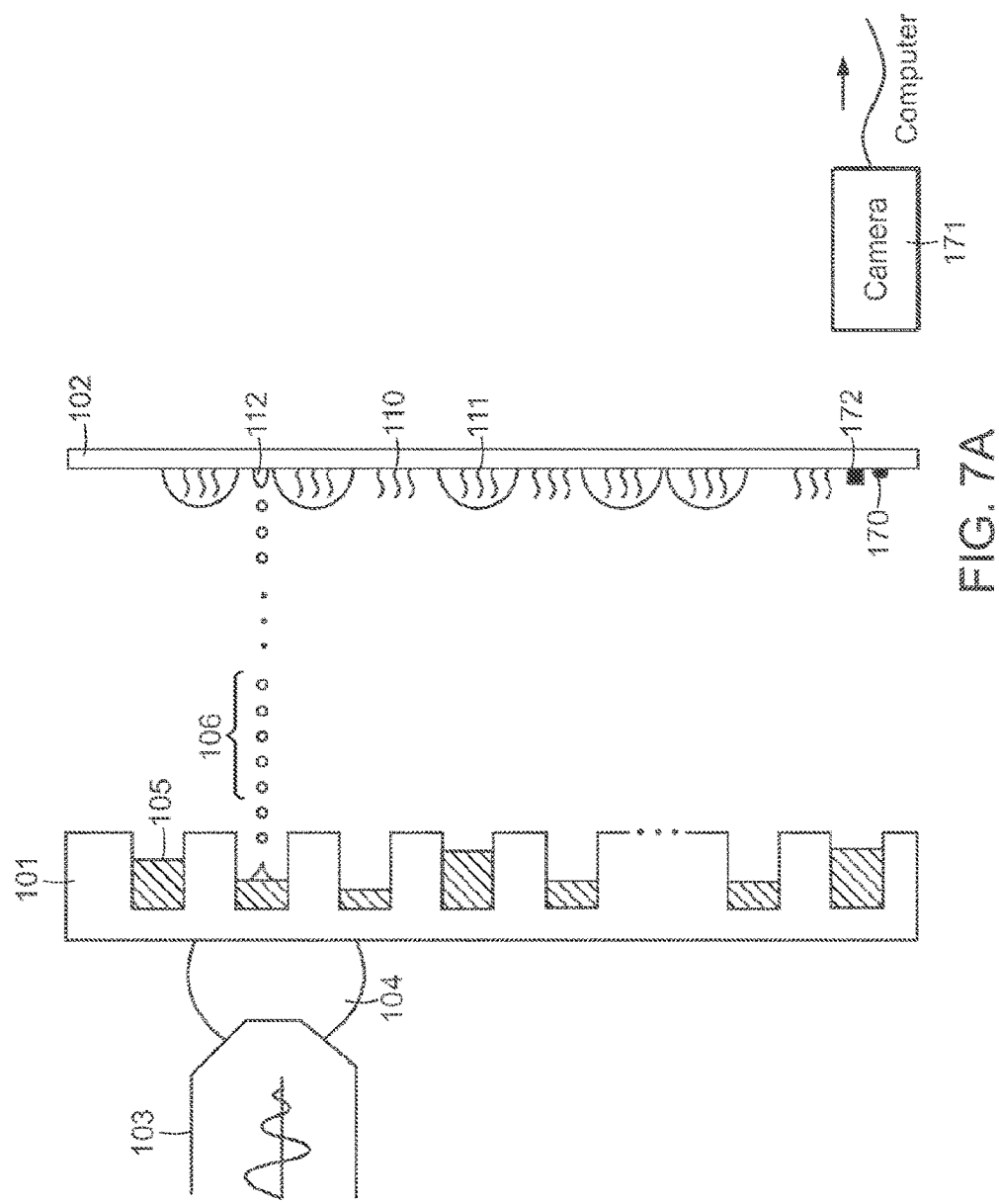

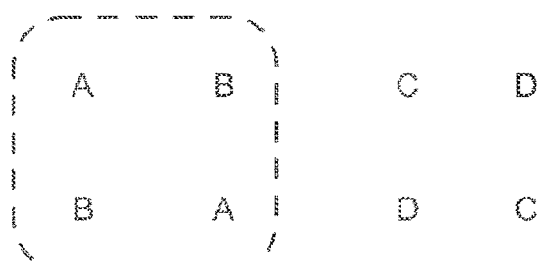
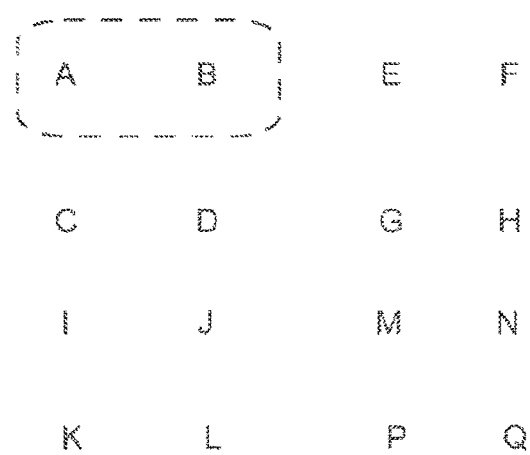
FIG. 11B

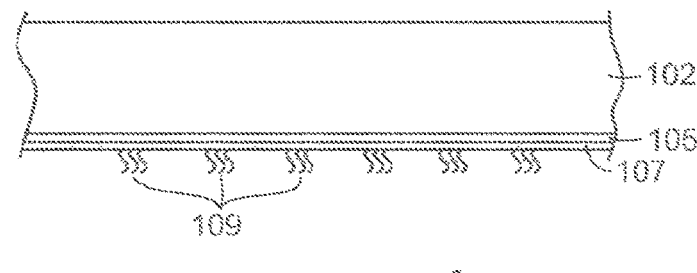
A
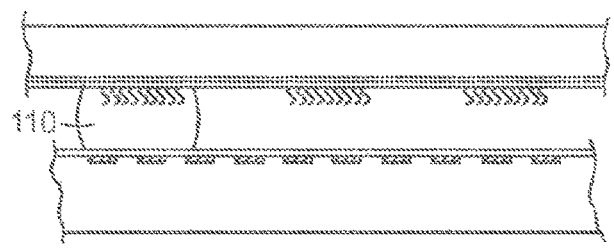
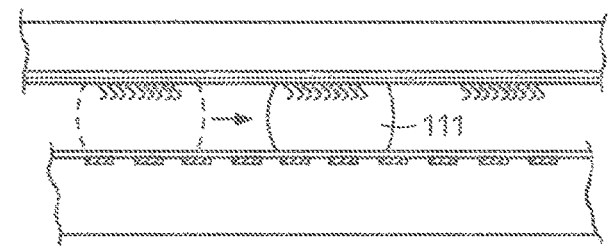
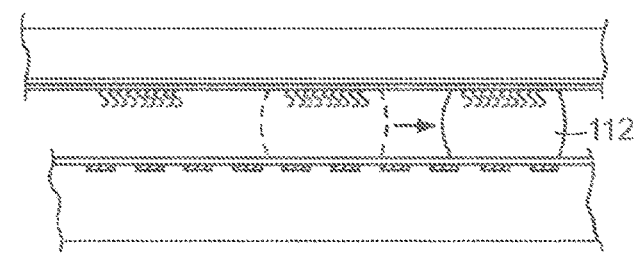
FIG. 17    B

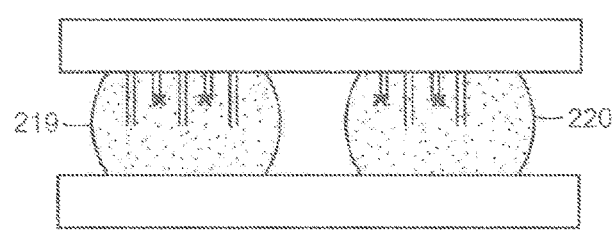
A
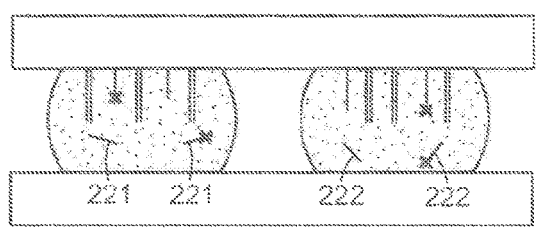
B
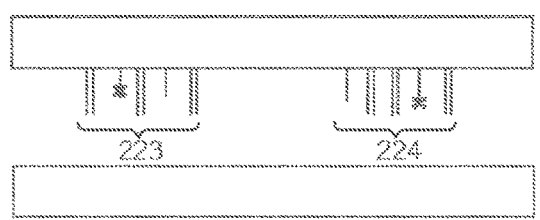
FIG. 20  C

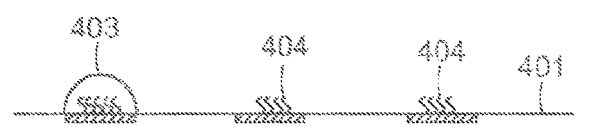
A
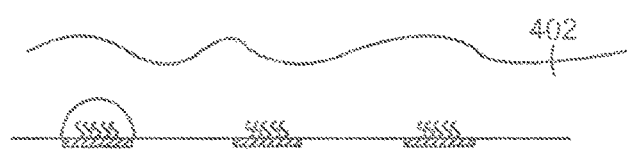
B
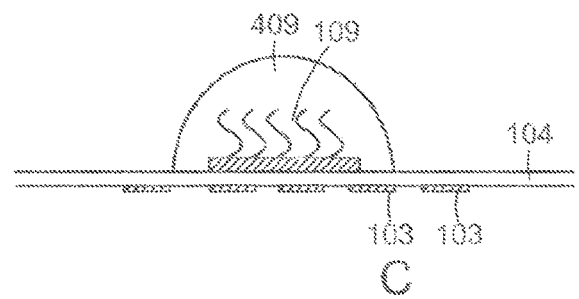
C
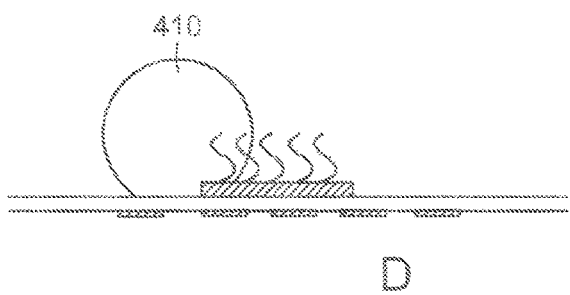
FIG. 22          D

METHODS AND MICROFLUIDIC DEVICES FOR THE MANIPULATION OF DROPLETS IN HIGH FIDELITY POLYNUCLEOTIDE ASSEMBLY

STATEMENT REGARDING FEDERALLY SPONSORED RESEARCH

This invention was made with the United States Government support under the cooperative agreement number 70NANB7H7034N awarded by the National Institute of Standards and Technology. The United States Government has certain rights in the invention.

RELATED APPLICATIONS

This application is a National Phase application of International Application No. PCT/US2010/055298 filed Nov. 3, 2010, which claims the benefit from U.S. provisional Ser. No. 61/257,591, filed Nov. 3, 2009, U.S. provisional application Ser. No. 61/264,641, filed Nov. 25, 2009, U.S. provisional application Ser. No. 61/310,069, filed Mar. 3, 2010, now expired, the contents of each of the foregoing applications are herein incorporated by reference in their entirety.

FIELD OF THE INVENTION

Methods and devices provided herein generally relate to droplet-based liquid manipulation on a substrate. In some embodiments, picoliter and sub-picoliter volume dispensing and droplet translocation technologies are applied to access and manipulate the oligonucleotides on a substrate. More particularly, methods and devices herein relate to the assembly of high fidelity nucleic acids having a predefined sequence and libraries of such predefined nucleic acids, the methods and devices using microvolume reactions, error filtration, hierarchical assembly, and/or sequence verification on a solid support.

BACKGROUND

Using the techniques of recombinant DNA chemistry, it is now common for DNA sequences to be replicated and amplified from nature and then disassembled into component parts. As component parts, the sequences are then recombined or reassembled into new DNA sequences. However, reliance on naturally available sequences significantly limits the possibilities that may be explored by researchers. While it is now possible for short DNA sequences to be directly synthesized from individual nucleosides, it has been generally impractical to directly construct large segments or assemblies of polynucleotides, i.e., polynucleotide sequences longer than about 400 base pairs. Furthermore, the error rate of chemically-synthesized oligonucleotides (deletions at a rate of 1 in 100 bases and mismatches and insertions at about 1 in 400 bases) exceeds the error rate obtainable through enzymatic means of replicating an existing nucleic acid (e.g., PCR). Therefore, there is an urgent need for new technology to produce high-fidelity polynucleotides.

Oligonucleotide synthesis can be performed through massively parallel custom syntheses on microchips (Zhou et al. (2004) Nucleic Acids Res. 32:5409; Fodor et al. (1991) Science 251:767). However, current microchips have very low surface areas and hence only small amounts of oligonucleotides can be produced. When released into solution, the oligonucleotides are present at picomolar or lower concentrations per sequence, concentrations that are insufficiently high to drive bimolecular priming reactions efficiently. Current methods for assembling small numbers of variant nucleic acids cannot be scaled up in a cost-effective manner to generate large numbers of specified variants. As such, a need remains for improved methods and devices for high-fidelity gene assembly and the like.

SUMMARY

Methods and devices provided herein generally relate to droplet-based liquid manipulation on a substrate. In some embodiments, picoliter and sub-picoliter volume dispensing and droplet surface tensions are used to access and manipulate the droplets on a substrate. It is an object of this invention to provide microfluidic devices for the manipulations of droplets. It is also an object of the invention to provide methods and devices for processing nucleic acids, (e.g. oligonucleotides) amplification reactions and assembly reactions.

Aspects of the invention relate to methods and devices for preparing oligonucleotides on a support. In some embodiments, a support comprising a plurality of surface-bound single stranded oligonucleotides which are contained within one or more droplets of a predefined volume of solution is provided. In some embodiments, a plurality of complementary oligonucleotides is generated within the droplet volume by exposing the plurality of surface-bound oligonucleotides to conditions suitable for a template-dependent synthesis and the volume of the one or more droplets of solution is adjusted or maintained. In some embodiments, the volume of the droplets of solution is maintained by maintaining the droplets under conditions that substantially limit water evaporation. For example, the plurality of surface-bound oligonucleotides may be coupled to the surface at a feature that is selectively coated with a coating material. The coating material may have water trapping properties and may be selected from the group of colloidal silica, peptide gel, agarose, solgel and polydimethylsiloxane, or any combination thereof. In another embodiment, water evaporation is limited by blocking the interface of the droplet with the atmosphere. For example, the droplets can be overlaid with a non-miscible liquid thereby preventing water evaporation of the solution. In some embodiments, the non-miscible liquid forms a lipid bilayer and the lipid bilayer is evaporated to form a thin film at the surface of the droplet. In some exemplary embodiments, the non-miscible liquid is a solvent or mineral oil. The non-miscible liquid may spotted onto the droplet, for example using an inkjet or mechanical device. In some embodiments, the volume of the droplet is maintained by adjusting the droplet volume by providing additional solution in response to evaporation. The water addition can be semi-continuous and can be added using an inkjet device. In some embodiments, water evaporation is limited by controlling the local humidity around the droplets. For example, the local humidity is increased by depositing satellite droplets in the vicinity of the droplets.

Aspects of the invention relate to methods and devices for monitoring a plurality of isolated reaction volumes on a support. In some embodiments, the method comprises providing a first support comprising a plurality isolated reaction volumes having a predefined surface-to-volume ratio; providing a second support comprising at least one monitoring isolated volume, wherein the monitoring volume has an identical surface-to-volume ratio to at least one of the reaction volume; and monitoring the volume of the at least one monitoring isolated volume, wherein the modification of the isolated monitoring volume is indicative of the modification of at least one isolated reaction volume. The first and second support can be the same or the isolated reaction volumes and isolated monitoring volumes are deposited on the same support. In preferred embodiments, the isolated volumes are droplets. In preferred embodiments, the isolated reaction volume comprises a solvent and wherein the monitoring volume comprises the same solvent. The reaction volume can comprise oligonucleotides. Modification of volume, such as increase of volume or decrease of volume is monitored. The reaction volumes and the isolated monitoring volumes are subjected to preselected conditions such as temperature, pressure, and gas mixture environment. The surfaces of the isolated reaction volumes and the isolated monitoring volumes are in contact with the preselected gas mixture, for example a gas mixture having predefined molar ratio of solvent vapor and carrier gas. In some embodiments, the conditions are modified to induce isolated volume growth. Yet in other embodiments, the conditions are modified to induce isolated volume evaporation. In some embodiments, the monitoring isolated volumes are placed on a mirror surface and the volume of the at least one monitoring isolated volume is monitored using an optical system. In an exemplary embodiment, the volume of the at least one monitoring isolated volume is monitored by measuring the intensity of an optical beam reflected on the second support. In some embodiments, the volume changes of the isolated reaction volumes is measured by providing a second support, such as a mirror and measuring the condensation on the second support using an optical system. In preferred embodiments, the condensation is measured by measuring the intensity of an optical beam reflected on the mirror.

In some embodiments, the surface bound oligonucleotides comprise a primer binding site and the solution comprises a polymerase, at least one primer and dNTPs wherein the primer is complementary to the primer binding site. The primer may be a unique primer, a universal primer, a pair of primers, a pair of unique primers, or a pair of universal primers. Oligonucleotides may be amplified by subjecting the plurality of surface-bound oligonucleotides to thermocycling thereby promoting primer extension.

In some embodiments, methods and devices for moving a droplet on a substrate are provided. In some embodiments, the substrate may be partitioned with a plurality of surface modifiers. The substrate may be partitioned according to a pattern such as an alternative pattern. The plurality of modifiers may comprise a plurality of first modifiers and plurality of second modifiers. In some embodiments, the plurality of first modifiers has a contact angle smaller than the plurality of second modifiers. In some embodiments, each of the plurality of first modifiers is associated with a different contact angle and the plurality of first modifiers is arranged in a series of decreasing or increasing contact angles. The plurality of modifiers can then form a hydrophilic gradient. In some embodiments, the first modifier is contacted with a droplet, and the droplet is moved on a substrate along a path towards the first modifiers having smaller contact angles. In an exemplary embodiment, the first modifier is contacted using an inkjet device. Therefore, the droplet may be moved along a hydrophilic gradient. In some embodiments, the first and second modifiers' contact angles differ by more than 30°. In some embodiments, the first modifiers comprise a plurality of oligonucleotides. In some embodiments, the second modifier correspond to the unmodified substrate surface. In another embodiment, the second modifier comprises a different surface modifier than the first modifier. In some embodiments, the first modifier is surrounded by second modifiers. In some embodiment, the droplet moves along a pre-determined path comprising a pattern of modifiers. In preferred embodiments, the path is a hydrophilic gradient and the droplet move according to surface-tension properties. Droplets may be moved along a one or a two dimensional path.

Aspects of the invention relate to methods and devices for moving and merging droplets on substrate surface comprising a plurality of features. In some embodiments, a first feature is contacted with a first droplet, and a second feature is contacted with a second droplet. The first and second features may be adjacent to each others. In preferred embodiment, the second droplet volume is greater than the first droplet volume. The first of the second droplet is then contacted with a third droplet volume allowing the merging of the droplets into a fourth droplet. In some embodiments, the volume of the first droplet is therefore moved from the first feature to the second feature on the substrate. Volume of the resultant droplet may be reduced to the original volume of the first droplet and steps may be repeated. Using the process of adjusting volumes and using surface tension properties, droplets can be moved along a predetermined path.

Other aspects of the invention relate to methods and devices for conducting sub-microvolume specified reactions within a droplet. In some embodiments, a substrate is provided comprising a plurality of surface-bound single-stranded oligonucleotides at discrete features. In other embodiments, only a selected set of oligonucleotides suitable for hydration are hydrated while the remainder of the support remains dry. In one embodiment, each oligonucleotide has a predefined sequence different from the predefined sequence of the oligonucleotide bound to a different feature. In some embodiments, a set of predefined features may be selectively hydrated, thereby providing hydrated oligonucleotides. In another embodiment, the hydrated oligonucleotides are exposed to further processing within a droplet volume. In some embodiments, the oligonucleotides are subjected to amplification. As each feature can selectively be hydrated, amplification will take place only at specific features comprising a droplet. In some embodiments, the droplet acts as a virtual reaction chamber. In some embodiments, the features can be hydrated with a solution promoting primer extension onto at least one feature creating at least one first stage droplet. For example, the solution may comprise a polymerase, at least one primer and dNTPs wherein the primer is complementary to a primer binding site. The primer may be a unique primer, a universal primer, a pair of primers, a pair of unique primers, or a pair of universal primers. Oligonucleotides may be amplified by subjecting at least one feature to thermocycling thereby promoting primer extension. In some other embodiments, the entire surface is subjected to thermocycling. In subsequent steps, the surface is heated to a denaturing temperature thereby providing a plurality of single-stranded complementary oligonucleotides within the first stage droplet. In other embodiments, the water evaporation or volume of the droplets is controlled. For example, the discrete features may be selectively coated with a coating material which may have water-trapping properties. In some embodiments, the coating material may be colloidal silica, peptide gel, agarose, solgel, polydimethylsiloxane, or any combination thereof. In another embodiment, water evaporation is limited by blocking the interface of the droplet with the atmosphere. For example, the droplets can be overlaid with a non-miscible liquid thereby preventing water evaporation of the solution. In some embodiments, the non-miscible liquid forms a lipid bilayer and the lipid bilayer is evaporated to form a thin film at the surface of the droplet. In some exemplary embodiments, the non-miscible liquid is a solvent or mineral oil. The non-miscible liquid may spotted onto the droplet, for example using an inkjet or mechanical device. In some embodiments, the volume of the droplet is maintained by addition of solution to the droplet. The water addition can be semi-continuous and can be added using an inkjet device. In some embodiments, water evaporation is limited by controlling the local humidity around the droplets. For example, the local humidity is increased by depositing satellite droplets in the vicinity of the droplets.

Aspects of the invention also relate to methods and devices for removing error-containing oligonucleotides from a plurality of amplified oligonucleotides. In some embodiments, the method comprises the steps of hydrating at least one first feature of the solid support following the amplification step forming a droplet comprising oligonucleotides duplexes; heating the solid support to a first melting temperature under stringent melt conditions, thereby denaturing duplexes comprising error-containing oligonucleotides and releasing error-containing oligonucleotides; removing the error-containing oligonucleotides from the solid support; optionally repeating previous steps on at least one second different feature and at least one different melting temperature; denaturing error-free duplexes; and releasing error-free oligonucleotides in solution. Stringent melt conditions can be determined by a real-time melt curve. In some embodiments, the support is dried prior to first and subsequent hydrating step. In some embodiments, a subset of discrete features is selectively heated. For example, one or more discrete features are selectively heated using a digital mirror device.

Other aspects of the invention relate to methods and devices for assembling at least one polynucleotide having a predefined sequence on a support. In one embodiment, a support is provided that comprises at least one feature having a plurality of surface-bound single-stranded oligonucleotides that are in a dry form and suitable for hydration. Each plurality of oligonucleotides is bound to a discrete feature of the support, and the predefined sequence of each plurality of oligonucleotides attached to the feature is different from the predefined sequence of the plurality of oligonucleotides attached to a different feature. At least one feature is hydrated thereby providing hydrated oligonucleotides within a droplet. In some embodiments, at least one plurality of oligonucleotides is synthesized in a chain extension reaction on a first feature of the support by template-dependent synthesis. The products of chain extension are subjected to at least one round of denaturation and annealing. The support is then heated to a first melting temperature under stringent melt conditions thereby denaturing duplexes comprising error-containing oligonucleotides and releasing error-containing oligonucleotides in solution. Error-containing oligonucleotides are removed from the support. The steps can be repeated on at least one other feature and at least one different melting temperature. Error-free duplexes are denatured and error-free oligonucleotides are released in solution within a first stage droplet. A first droplet comprising a first plurality of substantially error-free oligonucleotides can then be combined to a second droplet comprising a second plurality of substantially error-free oligonucleotides, wherein a terminal region of the second plurality of oligonucleotides comprise complementary sequences with a terminal region of the first set of plurality of oligonucleotides. The first and second plurality of oligonucleotides can then be contacted under conditions that allow one or more of annealing, chain extension, and denaturing. In some embodiments, the first and second droplets are combined by merging the droplets into a second stage droplet. First and/or second droplets can be moved from a first feature to a second feature of the support. In some embodiments, the surface is coated with a low melting-point substance for storage, for example wax, for storage. In some embodiments, the reactions are initiated by heating the surface above the low-melting point. Yet in other embodiments, the reactions are initiated by hydrating the discrete features.

Aspect of the invention relate to methods and devices of preparing a plurality of oligonucleotides using two supports. In some embodiments, a first support comprising a plurality of discrete features is provided and a second support is provided, the second support comprising an array of electrodes. The first and second support may be the same. Each feature comprising a plurality of surface-bound single-stranded oligonucleotides having a predefined sequence. In some embodiments, a droplet is dispensed at a first selected feature and at least one plurality of oligonucleotides is synthesized in a chain extension reaction on the first feature of the support by template-dependent synthesis. The products of chain extension are then subjected to at least on round of denaturation and annealing to for duplex oligonucleotides and the duplexes are exposed to conditions promoting error reduction. Error reduction may be an error filtration process, an error correction process or an error neutralization process. In some embodiments, the error reduction utilizes a mismatch endonuclease such as a CEL1 or a Surveyor™ endonuclease to cleave heteroduplexes. In some embodiments, the droplet is moved to the selected feature by activating and deactivating a selected set of electrodes. In some embodiments, the two supports are arranged together relative to each other by a distance sufficient to define a space in some embodiments, the error containing duplexes are exposed with a mismatch endonuclease under conditions that permit cleavage of oligonucleotide duplexes having at least one mismatch and the cleaved duplexes are removed. In some embodiments, the method further comprises denaturing surface-bound cleaved duplexes, removing single stranded cleaved oligonucleotides, denaturing surface-bound substantially error free oligonucleotide duplexes and releasing a first plurality of substantially error-free complementary oligonucleotides in first droplet volume. In some embodiments, a second plurality of substantially error-free oligonucleotides is released in second droplet volume. The first and second droplet may be moved towards a third feature to form a merged droplet by activating and deactivating a set of electrodes, thereby mixing the first and second droplets composition together. In some embodiments, the method further combines a first droplet comprising a first plurality of substantially error-free oligonucleotides to a second droplet comprising a second plurality of substantially error-free oligonucleotides, wherein a terminal region of the second plurality of oligonucleotides comprises complementary sequences with a terminal region of the first set of plurality of oligonucleotides. The first and second plurality of oligonucleotides are then contacted under conditions that allow one or more of annealing, chain extension and denaturing reaction. In some embodiments, one or more discrete features are selectively heated, for example, using a digital mirror device.

In other embodiments, a plurality of oligonucleotides having a predefined sequence are synthesized on a support. First, a plurality of surface-bound single-stranded oligonucleotides having a predefined sequence are provided wherein the plurality of oligonucleotides are suitable for hydration and wherein each plurality of oligonucleotides is bound to a discrete feature of the support, wherein the predefined sequence of each plurality of oligonucleotides attached to the feature is different from the predefined sequence of the plurality of oligonucleotides attached to a different feature. One feature is selectively inactivated by overlaying the selected feature with an immiscible solution and at least one second feature is selectively hydrated thereby providing hydrated oligonucleotides. At least one plurality of oligonucleotides is then synthesized in a chain extension reaction on a second feature of the support by template-dependent synthesis. The oligonucleotide duplexes are subjected to error-reduction and substantially error-free complementary oligonucleotides are released in a droplet volume. In some embodiments, an inactivated first feature is activated by removing the immiscible solution such as oil. In some embodiments, the method further comprises selectively hydrating the first feature thereby providing hydrated oligonucleotides, synthesizing a plurality of oligonucleotides in a chain extension reaction on a first feature of the support by template-dependent synthesis, subjecting oligonucleotide duplexes to error-reduction, and releasing substantially error-free complementary oligonucleotides in a droplet volume. In some embodiments, the droplets may be moved by electrowetting.

In some embodiments, the plurality of single-stranded oligonucleotides are synthesized at each feature using high-voltage complementary semiconductor device. In other embodiments, the plurality of single-stranded oligonucleotides are synthesized at each feature using emulsion droplets.

Aspects of the invention relates to methods and devices for the synthesis of at least one oligonucleotide of a predefined sequence onto a discrete feature of the support. In some embodiments, a first support comprising a plurality of discrete features and a second support comprising a high density array of electrodes are provided. Droplets are provided on selected features, the droplets comprising a reagent for performing a step of oligonucleotide synthesis. Preferably, the droplets are moved using high voltage electronics to a second selected feature for performing a step of the oligonucleotide synthesis, thereby producing the oligonucleotide of interest. In other embodiments, a support is provided, the support comprising a plurality of discrete features. Emulsion droplets are provided onto selected features, the droplet comprising a reagent for performing a step of oligonucleotide synthesis. Droplets containing different reagents for performing a step of oligonucleotide synthesis can be merged to perform and synthesize the oligonucleotide of interest. The reagents may be selected from the group consisting of a coupling reagent, T coupling reagent, C coupling reagent, G coupling reagent, U coupling reagent, deblocking reagent, oxidation reagent, capping reagent. In some embodiments, each droplet comprises a reagent for the oligonucleotide synthesis, each reagent being encapsulated into an aqueous droplet within an immiscible compound such as oil and surfactant.

BRIEF DESCRIPTION OF THE DRAWINGS

FIG. 1A illustrates an embodiment of the device comprising a substrate (1) with a surface (2), the surface being partitioned with modifiers (3) or (3) and (4).

FIG. 1B illustrates an embodiment of the device comprising partitioning of surface (2) with modifiers (3).

FIG. 1C illustrates an embodiment of the device comprising possible patterning configurations.

FIG. 2B illustrates a non-limiting example of possible footprint (24A; 24B, 24C) of the merged droplet (24).

FIG. 4A illustrates a non-limiting embodiment of the merging of a smaller droplet 41 with a larger droplet 42, using a merger droplet 43, into a merged droplet 44A and the repeated steps to allow the move of the droplet to a selected location of the substrate.

FIG. 4B illustrates a non limiting embodiment of droplet displacement.

FIG. 7A illustrates an embodiment of the device comprising a source well plate (101), containing the reagents for reactions, a solid support (102), with solid-surface attached or supported molecules, a transducer (103), a coupling fluid (104), reagents (105) inside a well, solid attached or surface supported molecules (110), surface droplets (111) formed by the dispensed droplets (106), a "merge" droplet (112) dispensed between two surface droplets (111), a surface droplet (170) dispensed for the purpose of alignment of the droplet to the solid attached molecules (111), an electronics camera (171) and used to provide physical registration (positioning) and a surface mark (172) fixed on the solid support (102).

FIG. 11B illustrates a non-limiting example of an assembly strategy.

FIG. 17 illustrates a non limiting embodiment of the electrowetting device with a bottom side electrode.

FIG. 20 illustrates a non limiting embodiment of selective error-removal of error-containing oligonucleotides.

FIG. 22 illustrates an exemplary method using an immiscible fluid system in polynucleotide assembly.

DETAILED DESCRIPTION OF THE INVENTION

Figure 2A:
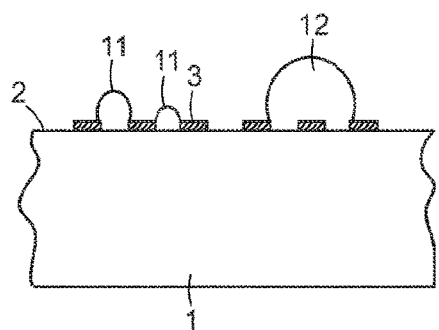
FIG. 2A illustrates a non-limiting example of droplet footprint on a substrate (1) comprising a surface (2) and modifiers (3), the contact angle of the droplet being smaller on (2) than on (3).

Provided herein are microfluidic devices for the manipulation of droplets on a substrate. Methods and devices for synthesizing or amplifying oligonucleotides as well for preparing or assembling long polynucleotides having a predefined sequence are provided herein. Aspects of the technology provided herein are useful for increasing the accuracy, yield, throughput, and/or cost efficiency of nucleic acid synthesis and assembly reactions. As used herein the terms "nucleic acid", "polynucleotide", "oligonucleotide" are used interchangeably and refer to naturally-occurring or synthetic polymeric forms of nucleotides. The oligonucleotides and nucleic acid molecules of the present invention may be formed from naturally occurring nucleotides, for example forming deoxyribonucleic acid (DNA) or ribonucleic acid (RNA) molecules. Alternatively, the naturally occurring oligonucleotides may include structural modifications to alter their properties, such as in peptide nucleic acids (PNA) or in locked nucleic acids (LNA). The solid phase synthesis of oligonucleotides and nucleic acid molecules with naturally occurring or artificial bases is well known in the art. The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases. As used herein, the term monomer refers to a member of a set of small molecules which are and can be joined together to form an oligomer, a polymer or a compound composed of two or more members. The particular ordering of monomers within a polymer is referred to herein as the "sequence" of the polymer. The set of monomers includes but is not limited to, for example, the set of common L-amino acids, the set of D-amino acids, the set of synthetic and/or natural amino acids, the set of nucleotides and the set of pentoses and hexoses. Aspects of the invention described herein primarily with regard to the preparation of oligonucleotides, but could readily be applied in the preparation of other polymers such as peptides or polypeptides, polysaccharides, phospholipids, heteropolymers, polyesters, polycarbonates, polyureas, polyamides, polyethyleneimines, polyarylene sulfides, polysiloxanes, polyimides, polyacetates, or any other polymers.

As used herein, the term "predefined sequence" means that the sequence of the polymer is known and chosen before synthesis or assembly of the polymer. In particular, aspects of the invention is described herein primarily with regard to the preparation of nucleic acids molecules, the sequence of the oligonucleotides or polynucleotides being known and chosen before the synthesis or assembly of the nucleic acid molecules. In some embodiments of the technology provided herein, immobilized oligonucleotides or polynucleotides are used as a source of material. In various embodiments, the methods described herein use oligonucleotides, their sequence being determined based on the sequence of the final polynucleotides constructs to be synthesized. In one embodiment, "oligonucleotides" are short nucleic acid molecules. For example, oligonucleotides may be from 10 to about 300 nucleotides, from 20 to about 400 nucleotides, from 30 to about 500 nucleotides, from 40 to about 600 nucleotides, or more than about 600 nucleotides long. However, shorter or longer oligonucleotides may be used. Oligonucleotides may be designed to have different length. In some embodiments, the sequence of the polynucleotide construct may be divided up into a plurality of shorter sequences that can be synthesized in parallel and assembled into a single or a plurality of desired polynucleotide constructs using the methods described herein.

In some embodiments, the assembly procedure may include several parallel and/or sequential reaction steps in which a plurality of different nucleic acids or oligonucleotides are synthesized or immobilized, amplified, and are combined in order to be assembled (e.g., by extension or ligation as described herein) to generate a longer nucleic acid product to be used for further assembly, cloning, or other applications (see U.S. provisional application 61/235, 677 and PCT application PCT/US09/55267 which are incorporate herein by reference in their entirety). Amplification and assembly strategies provided herein can be used to generate very large libraries representative of many different nucleic acid sequences of interest.

In some embodiments, methods of assembling libraries containing nucleic acids having predetermined sequence variations are provided herein. Assembly strategies provided herein can be used to generate very large libraries representative of many different nucleic acid sequences of interest. In some embodiments, libraries of nucleic acid are libraries of sequence variants. Sequence variants may be variants of a single naturally-occurring protein encoding sequence. However, in some embodiments, sequence variants may be variants of a plurality of different protein-encoding sequences.

Accordingly, one aspect of the technology provided herein relates to the design of assembly strategies for preparing precise high-density nucleic acid libraries. Another aspect of the technology provided herein relates to assembling precise high-density nucleic acid libraries. Aspects of the technology provided herein also provide precise high-density nucleic acid libraries. A high-density nucleic acid library may include more that 100 different sequence variants (e.g., about 102 to 103; about 103 to 104; about 104 to 105; about 105 to 106; about 106 to 107; about 107 to 108; about 108 to 109; about 109 to 1010; about 1010 to 1011; about 1011 to 1012; about 1012 to 1013; about 1013 to 1014; about 1014 to 1015 or more different sequences) wherein a high percentage of the different sequences are specified sequences as opposed to random sequences (e.g., more than about 50%, more than about 60%, more than about 70%, more than about 75%, more than about 80%, more than about 85%, more than about 90%, more than about 91%, more than about 92%, more than about 93%, more than about 94%, more than about 95%, more than about 96%, more than about 97%, more than about 98%, more than about 99%, or more of the sequences are predetermined sequences of interest).

Some embodiments of the devices and methods provided herein use oligonucleotides that are immobilized on a support or substrate. As used herein the term "support" and "substrate" are used interchangeably and refers to a porous or non-porous solvent insoluble material on which polymers such as nucleic acids are synthesized or immobilized. As used herein "porous" means that the material contains pores having substantially uniform diameters (for example in the nm range). Porous materials include paper, synthetic filters and the like. In such porous materials, the reaction may take place within the pores. The support can have any one of a number of shapes, such as pin, strip, plate, disk, rod, bends, cylindrical structure, particle, including bead, nanoparticle and the like. The support can have variable widths. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like etc.; either used by themselves or in conjunction with other materials. In some embodiments, oligonucleotides are synthesized on an array format.

For example, single-stranded oligonucleotides are synthesized in situ on a common support wherein each oligonucleotide is synthesized on a separate or discrete feature (or spot) on the substrate. In preferred embodiments, single stranded oligonucleotides are bound to the surface of the support or feature. As used herein the term "array" refers to an arrangement of discrete features for storing, routing, amplifying and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule of the array is localized to a known and defined location on the support. The sequence of each oligonucleotide can be determined from its position on the support. Moreover, addressable supports or arrays enable the direct control of individual isolated volumes such as droplets. The size of the defined feature can be chosen to allow formation of a microvolume droplet on the feature, each droplet being kept separate from each other. As described herein, features are typically, but need not be, separated by interfeature spaces to ensure that droplets between two adjacent features do not merge. Interfeatures will typically not carry any oligonucleotide on their surface and will correspond to inert space. In some embodiments, features and interfeatures may differ in their hydrophilicity or hydrophobicity properties. In some embodiments, features and interfeatures may comprise a modifier as described herein.

Arrays may be constructed, custom ordered or purchased from a commercial vendor (e.g., Agilent, Affymetrix, Nimblegen). Oligonucleotides are attached, spotted, immobilized, surface-bound, supported or synthesized on the discrete features of the surface or array Oligonucleotides may be covalently attached to the surface or deposited on the surface. Various methods of construction are well known in the art e.g. maskless array synthesizers, light directed methods utilizing masks, flow channel methods, spotting methods etc.

In some embodiments, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single-stranded DNA molecule of desired sequence.

Other methods for synthesizing construction and/or selection oligonucleotides include, for example, light-directed methods utilizing masks, flow channel methods, spotting methods, pin-based methods, and methods utilizing multiple supports.

Light directed methods utilizing masks (e.g., VLSIPS™ methods) for the synthesis of oligonucleotides is described, for example, in U.S. Pat. Nos. 5,143,854; 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be optionally used. Other applicable methods include mechanical techniques such as those described in U.S. Pat. No. 5,384,261.

Additional methods applicable to synthesis of construction and/or selection oligonucleotides on a single support are described, for example, in U.S. Pat. No. 5,384,261. For example, reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites. Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region.

Pin-based methods for synthesis of oligonucleotides on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-wells microtiter dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In another embodiment, a plurality of oligonucleotides may be synthesized on multiple supports. One example is a bead based synthesis method which is described, for example, in U.S. Pat. Nos. 5,770,358; 5,639,603; and 5,541,061. For the synthesis of molecules such as oligonucleotides on beads, a large plurality of beads is suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

In yet another embodiment, a plurality of oligonucleotides may be attached or synthesized on nanoparticles. Nanoparticles includes but are not limited to metal (e.g., gold, silver, copper and platinum), semiconductor (e.g., CdSe, CdS, and CdS coated with ZnS) and magnetic (e.g., ferromagnetite) colloidal materials. Methods to attach oligonucleotides to the nanoparticles are known in the art. In another embodiment, nanoparticles are attached to the substrate. Nanoparticles with or without immobilized oligonucleotides can be attached to substrates as described in, e.g., Grabar et al., Analyt. Chem., 67, 73-743 (1995); Bethell et al., J. Electroanal. Chem., 409, 137 (1996); Bar et al., Langmuir, 12, 1172 (1996); Colvin et al., J. Am. Chem. Soc., 114, 5221 (1992). Naked nanoparticles may be first attached to the substrate and oligonucleotides can be attached to the immobilized nanoparticles.

Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Publication Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; the disclosures of which are incorporated herein by reference in their entirety for all purposes. In some embodiments, pre-synthesized oligonucleotides are attached to a support or are synthesized using a spotting methodology wherein monomers solutions are deposited dropwise by a dispenser that moves from region to region (e.g. ink jet). In some embodiments, oligonucleotides are spotted on a support using, for example, a mechanical wave actuated dispenser.

The manipulation of fluids to form fluid streams of desired configuration, such as discontinuous fluid streams, particles, dispersions, etc., for purposes of fluid delivery, product manufacture, analysis, and the like, is a relatively well-studied art. See for example, WO/2004/002627 which is incorporated herein in its entirety. In some aspects of the invention, microfluidic devices are used to form and manipulate droplets in a co-planar fashion to allow oligonucleotide synthesis. For example, oligonucleotides may be synthesized using a phosphoramidite method. The phosphoramidite method, employing nucleotides modified with various protecting groups, is one of the most commonly used methods for the de novo synthesis of oligonucleotides. Detailed procedures for the phosphoramidite and hydrogen phosphonate methods of oligonucleotide synthesis are described in the following references that are incorporated by reference: U.S. Pat. Nos. 4,500,707; 4,725,677; and 5,047,524. See also for example, methods outlined in Oligonucleotide and Analogs: A practical approach, F. Eckstein, Ed. IRL Press Oxford University and Oligonucleotide synthesis: A practical approach, Gait, Ed. IRL Oxford Press. Synthesis can be performed either through the coupling of the 5' position of the first monomer to the 3' position of the second monomer (3'-5' synthesis) or vive versa (5'-3' synthesis). Briefly, synthesis of oligonucleotides requires the specific formation of a 3'-5' or 5'3' phosphodiester linkage. In order to form these specific linkages, the nucleophilic centers not involved in the linkage must be chemically protected through the use of protecting group. By "protecting group" as used herein is meant a species which prevents a segment of a molecule (e.g. nucleotide) from undergoing a specific chemical reaction, but which is removable from the molecule following completion of that reaction. For example, the 5' hydroxyl group may be protected by dimethoxitrityl (DMT). During the deblocking reaction, the DMT is removed with an acid, such as thrichloroacetic acid (TeA) or dichloroacetic acid, resulting in a free hydroxyl group. After washing, a phosphoramidite nucleotide is activated by tetrazole, ethylthiotetrazole, dicyanoimidazole, or benzimidazolium triflate, for example, which remove the iPr2N group on the phosphate group. The deprotected 5' hydroxyl of the first base reacts with the phosphate of the second base and a 5'-3' linkage is formed (coupling step). Unbound bases are washed out and 5' hydroxyl group that did not react during the coupling reaction are blocked by adding a capping group, which permanently binds to the free 5' hydroxyl groups to prevent any further chemical transformation of that group (capping step). The oxidation step may be performed before or after the capping step. During oxidation, the phosphite linkage is stabilized to form a much more stable phosphate linkage. The deblocking/coupling/capping/oxidation cycle may be repeated the requisite number of time to achieve the desired length polynucleotide. In some embodiments, coupling can be synchronized on the array or solid support.

In some embodiments, the oligonucleotides synthesis is synthesized using a device that generates emulsion droplets comprising aqueous droplets within immiscible oil. The droplets may comprise an aqueous phase, an immiscible oil phase, and a surfactant and/or other stabilizing molecules to maintain the integrity of the droplet. In some embodiment, mechanical energy is applied, allowing dispersion of a compound into an oil phase to form droplets, each of which contains a single sort of compound. Preferably, the compound is a nucleotide monomer (i.e. A, T or U, G C). The compounds can be deposited into the oil phase in the form of droplets generated using inkjet printing technology or piezoelectric drop-on-demand (DOD) inkjet printing technology. Each droplet may comprise a different nucleotide monomer (i.e. A, T or U, G C) in the same aqueous solution. In preferred embodiments, the droplets are uniform in size and contain one nucleotide at a fixed concentration. The droplets range in size from 0.5 microns to 500 micron in diameter, which correspond to a volume of about 1 picoliter to about 1 nanoliter. Yet in other embodiments, the droplet may comprise a 2-mer, a 3-mer, a 4-mer, a 6-mer or a 7-mer oligonucleotide. In some embodiments, the droplets are deposited onto a substrate such as a microsubstrate, a microarray or a microchip. The terms microsubstrate, microarray and microchip are used interchangeably herein. The droplets may be deposited using a microfluidic nozzle. In some embodiments, the substrate may be subjected to wash, deblocking solution, coupling, capping and oxidation reactions to elongate the oligonucleotide.

In some embodiments, the droplets carrying the nucleotides can be moved using electrowetting technologies. Electrowetting involves modifying the surface tension of liquids on a solid surface using a voltage. Application of an electric field (e.g. alternating or direct), the contact angle between the fluid and surfaces can be modified. For example, by applying a voltage, the wetting properties of a hydrophobic surface can become increasingly hydrophilic and therefore wettable. Electrowetting principle is based on manipulating droplets on a surface comprising an array of electrodes and using voltage to change the interfacial tension. In some embodiments, the array of electrode is not in direct contact with the fluid. In some embodiments, the array of electrode is configured such as the support has a hydrophilic side and a hydrophobic side. The droplets subjected to the voltage will move towards the hydrophilic side. In some embodiments, the array or pattern of electrodes is a high density pattern. One should appreciate that to be used in conjunction with the phosphoramidite chemistry, the array of electrodes should be able to move droplets volumes ranging from 1 pL (and less) to 10 pL. Accordingly, aspects of the invention relate to high voltage complementary semi-conductor microfluidic controller. In some embodiments, the high voltage complementary semi-conductor device (HV-CMOS) has an integrated circuit with high density electrode pattern and high voltage electronics. In some embodiments, the voltage applied is between 15V and 30V.

Methods and devices provided herein involve amplification and/or small assembly reaction volumes such as microvolumes, nanovolumes, picovolumes or sub-picovolumes. Accordingly, aspects of the invention relate to methods and devices for amplification and/or assembly of polynucleotide sequences in small volume droplets on separate and addressable features of a support. For example, a plurality of oligonucleotides complementary to surface-bound single stranded oligonucleotides is synthesized in a predefined reaction microvolume of solution by template-dependant synthesis. In some embodiments, predefined reaction microvolumes of between about 0.5 pL and about 100 nL may be used. However, smaller or larger volumes may be used. In some embodiments, a mechanical wave actuated dispenser may be used for transferring volumes of less than 100 nL, less than 10 nL, less than 5 nL, less than 100 pL, less than 10 pL, or about 0.5 pL or less. In some embodiments, the mechanical wave actuated dispenser can be a piezoelectric inkjet device or an acoustic liquid handler. In a preferred embodiment, a piezoelectric inkjet device is used and can deliver picoliter solutions in a very precise manner on a support.

Aspects of the invention relate to the manipulation of sub-microvolumes on a substrate and to the control of the movement of micro-volumes on a substrate. It is a well-known phenomenon that the surfaces of most normally solid substrates, when contacted with a solution, have a characteristic degree of non-wettability. That is, aqueous solutions do not spread on the solid surface but contract to form droplets. Accordingly, preferable supports have surface properties, primarily surface tension and wettability properties that allow droplet formation when small volumes are dispensed onto the addressable feature. In some embodiments, the microvolume is bounded completely or almost completely by the free surface forming a droplet or microdrop. One skilled in the art will understand that the shape of the droplet will be governed and maintained by the contact angle of the liquid/solid interaction, surface tension of the liquid as well as by surface energy. Adhesive forces between a liquid and solid will cause a liquid drop to spread across the surface whereas cohesive forces within the liquid will cause the drop to ball up and avoid contact with the surface. For liquid, the surface energy density is identical to the surface tension. Surface tension is that property of matter, due to molecular forces, which exists in the surface film of all liquids and tends to bring the contained volume into a form having the least possible superficial area. In some embodiments, the support's surface is partitioned into discrete regions where the surface contact angles of at least a plurality of the discrete region differ for the fluid of interest. As used herein the term "contact angle" refers to a quantitative measure of the wetting of a solid by a liquid. A contact angle is defined as the angle formed by a liquid at the three phase boundary where vapor (gas, e.g., atmosphere), liquid and solid intersect. For example, in the case of a micro-volume droplet dispensed on a horizontal flat surface, the shape of the micro-volume droplet will be determined by the Young equilibrium equation:

$$0 = \gamma_{SV} - \gamma_{SL} - \gamma \cos \theta_C$$

wherein $\gamma_{SV}$ is the solid-vapor interfacial energy; $\gamma_{SL}$ is the solid-liquid interfacial energy and $\gamma$ is the liquid-vapor energy (i.e. surface tension) and $\theta_C$ is the equilibrium contact angle.

It will be understood that for contact angle values $\theta C$ less than 90°, the liquid will spread onto the solid surface. For example, very hydrophilic surfaces have a contact angle of 0° to about 30°. In the case of aqueous solutions and highly hydrophilic support, the contact angle $\theta C$ will be close to 0°, and the aqueous solution or droplet will completely spread out on the solid surface (i.e., complete wetting of the surface). On the contrary, for contact angle values $\theta C$ equal to or greater than 90°, the liquid will rest on the surface and form a droplet on the solid surface. The shape of the droplet is determined by the value of the contact angle. In the case of aqueous solutions and highly hydrophobic surfaces, liquid will bead up. In some embodiments, the support is chosen to have a surface energy and surface contact angle that does not allow the droplets to spread beyond the perimeter of the feature. Furthermore, on an ideal surface each droplet will return to its original shape if it is disturbed, for example after addition of a miscible or non-miscible solution. In some embodiments, the surface is partitioned into regions where the surface contact angles of the regions differ for the liquid of interest. In some embodiments, theses regions correspond to the discrete features of the substrate. In a preferred embodiment, the surface is partitioned into regions by modifiers. Modifiers may be added to specific locations of the substrate's surface. In some cases, the surface will be partitioned into regions comprising modifiers and unmodified surface areas. In some embodiments, the non-modifier regions correspond to the unmodified substrate. Yet, in other embodiments, the non-modifiers regions correspond to a surface of any arbitrary modification or any modifier that is different than the modifier a region that corresponds to a feature of a support. In some embodiments, the modifiers are oligomers. For example, the modifiers correspond to nucleic acids and are modifying a set of discrete features of the substrate. As shown in FIG. 1A-C, the surface comprises a pattern of modifiers and non-modifier regions having different surface contact angles. Exemplary patterning (or partitioning) of the surface is shown in FIG. 1A-C. Modifiers can have circular, square, trapezoid, or any geometrical shape or any combination thereof. In some embodiments, modifiers are arranged in a grid-like pattern or in any other different configurations. Pattern examples are shown in FIG. 1C. However, the pattern needs not to be restricted to any design. For example, the modifiers may be arranged in a randomly formed pattern. Patterning may be formed by any process known in the art. For example, arranged patterning or random patterning may be formed by processes such as block co-polymer surface self assembly. In other embodiments, the substrate surface is partitioned into regions by at least two different modifiers regions as discussed herein. In some embodiments, the surface contact angle of the modifiers ($\theta M$) is different than the surface contact angle of the non-modifier region ($\theta NM$). For example, the surface contact angle of the modifiers may be greater than the surface contact angle of the surface or the non-modifier regions ($\theta M > \theta NM$). Alternatively, the surface contact angle of the non-modifier regions is greater than the surface contact angle of the modifiers ($\theta M < \theta NM$). In the context of aqueous solutions, the modifiers surfaces may be more hydrophilic than the surface of the non-modifiers regions (i.e. surface contact angle of the modifiers is smaller than the surface contact angle of the surface or non-modifier regions). Alternatively, the modifiers surfaces may be more hydrophobic than the surface of the non-modifiers surface regions (i.e., surface contact angle of the modifiers is smaller than the surface contact angle of the surface or non-modifier regions). In an exemplary embodiment, modifiers are oligonucleotides and the surface of the modifier regions is more hydrophilic than the surface of the non-modifier regions. In other embodiments, the totality or a substantial part of the support or surface is covered with at least two different modifiers, such as for example a first and a second modifier (for example, modifiers (3) and (4) as shown in FIG. 1A-ii). The at least two different modifiers may be patterned as described above. For example, the first and second modifiers can cover the surface in an alternative pattern as shown in FIG. 1A-C. One should appreciate that the support surface may be covered with a plurality of modifiers that are disposed on the surface to form a hydrophilic gradient. In some embodiments, each modifier has a different contact angle than the adjacent modifier. In some embodiments, the surface is partitioned with a plurality of different modifiers, the plurality of first modifiers being more hydrophilic than the at least one second modifier, and the plurality of first modifiers having each a slightly different contact angle than the next first modifier. For example, the contact angle of each of the plurality of first modifier may differ by at least about 1°, 2°, 3°, 4°, 5°, 6°, 7°, 8°, 9°, 10°, 11°, 12°, 13°, 14°, 15°, 16°, 17°, 18°, 19°, 20°, 25°, 30° or more from that of the next first modifier. The plurality of first modifiers therefore forms a hydrophilic gradient and a predetermined path along which a droplet can be moved by surface-tension manipulation.

Figure 2B:
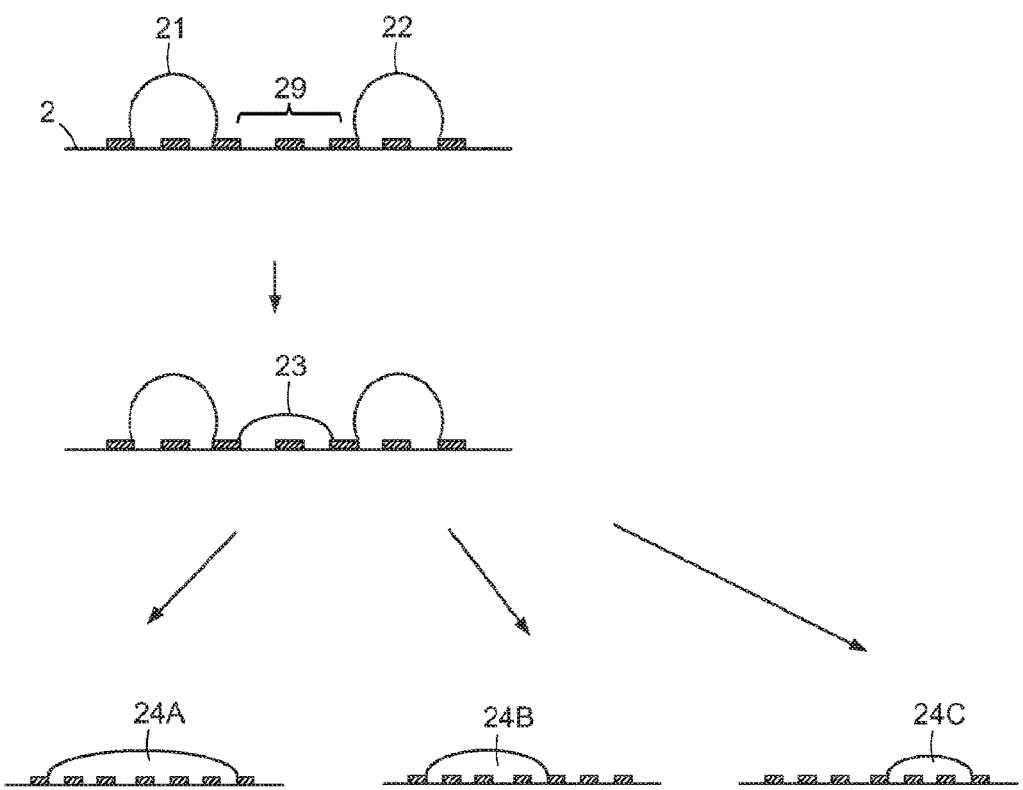
FIG. 2B illustrates a non-limiting example of the merging of two droplets (21 and 22) separated by a distance (29) using a merger droplet (23).

According to some aspects of the invention, the difference in surface contact angles between two different modifiers or a modifier and the non-modifier surface creates a virtual "wall". As used herein the term smaller contact angle (SCA) refers to the surface or modifier having smaller contact angle and the term higher contact angle (HCA) refers to the surface or modifier having higher contact angle. In the context of aqueous solutions, SCA are more hydrophilic than HCA. In some embodiments, HCA values are at least 20°, at least 30°, at least 35° higher than SCA. Accordingly, liquid volumes can be formed and isolated on surfaces comprising regions of SCA and regions of HCA. For example, if the surface contact angle of the modifier is greater than the non-modifier surface contact angle, liquid volumes will form a droplet between two modifiers regions (see FIG. 2A). One would appreciate that depending on liquid volume deposited onto the surface and the difference of contact values between modifiers, the droplet can occupy a single region of small contact angle (as shown by droplet 11 in FIG. 2) or multiple regions (as shown by droplet 12 in FIG. 2A). For example, the liquid volume may occupy 1, 2, 3, 4, 5, 6, 7, 8, 9, 10, or more SCA regions. Accordingly, the liquid can occupy a footprint corresponding to one or more SCA. The footprint may then encompass one or more HCA. In some embodiments, to ensure that two droplets or small isolated volumes will not merge, liquid volumes are placed sufficiently apart from each others. For example, the spacing between two isolated volumes may comprise at least one, at least two, at least three, at least four, at least five, at least six, at least seven, at least eight, at least nine, at least ten HCA regions or modifiers regions. Placing the liquid volumes sufficiently apart also allows for keeping liquid volumes isolated during fluctuation of temperature such as during thermocycling. Because surface tension usually decreases with the increase of temperature, droplets may spread or move on the surface when the temperature of the support or of the liquid volume is raised. It will be appreciate that if the liquid volumes are kept sufficiently apart, liquid volumes will remain isolated and will not merge with adjacent liquid volumes during fluctuation of the temperature.

In one aspect of the invention, methods and devices are provided for processing independently one or more plurality of oligonucleotides in a temperature dependent manner at addressable features in isolated liquid volumes. In some embodiments, the method is conducted in a manner to provide a set of predefined single-stranded oligonucleotide sequences or complementary oligonucleotide sequences for further specified reactions or processing. One should appreciate that each features being independently addressable, each reaction can be processed independently within a predefined isolated liquid volume or droplet on a discrete feature (e.g. virtual chamber). In some embodiments, the arrays are stored dry for subsequent reactions. In a preferred embodiment, support immobilized oligonucleotides can be hydrated independently with an aqueous solution. Aqueous solution includes, but is not limited to, water, buffer, primers, master mix, release chemicals, enzymes, or any combination thereof. Aqueous solution can be spotted or jetted onto specific surface location(s) corresponding to the discrete feature(s). Subsequently, miscible as well as non-miscible solution or aqueous gel can be deposited in the same fashion. Alternatively, a mechanical wave actuated dispenser can be used for transferring small volumes of fluids (e.g., picoliter or sub-picoliter). A mechanical wave actuated dispenser can be a piezoelectric inkjet device or an acoustic liquid handler. A piezoelectric inkjet device can eject fluids by actuating a piezoelectric actuation mechanism, which forces fluid droplets to be ejected. Piezoelectrics in general have good operating bandwidth and can generate large forces in a compact size. Some of the commercially available piezoelectric inkjet microarraying instruments include those from Perkin Elmer (Wellesley, Mass.), GeSim (Germany) and MicroFab (Plano, Tex.). Typical piezoelectric dispensers can create droplets in the picoliter range and with coefficient of variations of 3-7% Inkjetting technologies and devices for ejecting a plurality of fluid droplets toward discrete features on a substrate surface for deposition thereon have been described in a number of patents such as U.S. Pat. Nos. 6,511,849; 6,514,704; 6,042, 211; 5,658,802, the disclosure of each of which is incorporated herein by reference.

In one embodiment, the fluid or solution deposition is performed using an acoustic liquid handler or ejector. Acoustic devices are non-contact dispensing devices able to dispense small volume of fluid (e.g. picoliter to microliter), see for example Echo 550 from Labcyte (CA), HTS-01 from EDC Biosystems. Acoustic technologies and devices for acoustically ejecting a plurality of fluid droplets toward discrete sites on a substrate surface for deposition thereon have been described in a number of patents such as U.S. Pat. Nos. 6,416,164; 6,596,239; 6,802,593; 6,932,097; 7,090,333 and US Patent Application 2002-0037579, the disclosure of each of which is incorporated herein by reference. The acoustic device includes an acoustic radiation generator or transducer that may be used to eject fluid droplets from a reservoir (e.g. microplate wells) through a coupling medium. The pressure of the focused acoustic waves at the fluid surface creates an upwelling, thereby causing the liquid to urge upwards so as to eject a droplet, for example from a well of a source plate, to a receiving plate positioned above the fluid reservoir. The volume of the droplet ejected can be determined by selecting the appropriate sound wave frequency.

Figure 7B:
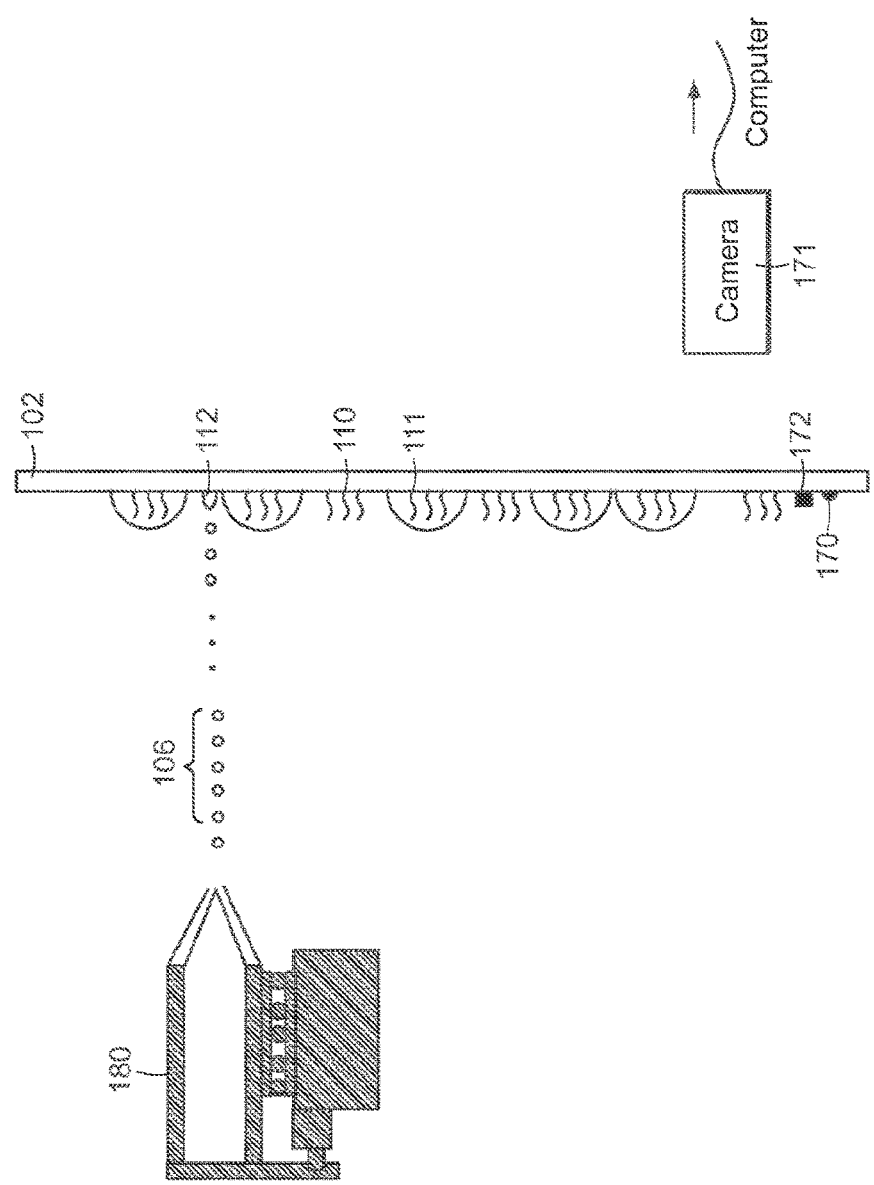
FIG. 7B illustrates an embodiment using an inkjet device for droplet dispensing. The head assembly (180) includes multiple jetting modules (181), with each module containing at least one reservoir (183) having at least one inlet (184). Each jetting module can have one or more than one nozzle (182), which can be arranged in a 1D or 2D array to form a nozzle pattern. The nozzles can have well defined dimensions to allow droplets (106) to form under the influence of a mechanical wave generated by a transducer (185).

In some embodiments, the source plate comprising water, buffer, primers, master mix, release chemicals, enzymes, or any combination thereof and the destination plates comprising the oligonucleotides or polynucleotides are matched up to allow proper delivery or spotting of the reagent to the proper site. The mechanical wave actuated dispenser may be coupled with a microscope and/or a camera to provide positional selection of deposited spots. A camera may be placed on both sides of the destination plate or substrate. A camera may be used to register to the positioning on the array especially if the DNA is coupled with a fluorescent label. As shown in FIG. 7A and described below components of the device include: 101: Source well plate; containing the reagents for reactions, this element can travel in at least 2 degree-of-freedom (>2DOF); 102: Solid support, with solid attached molecules, this element can travel in at least 2 degree-of-freedom (>2DOF); 103: Transducer, to create a mechanical wave which causes droplets to form and travel, this element can travel in at least 2 degree-of-freedom (>2DOF); 104: Coupling fluid, to allow the mechanical wave to couple to the well plate (101); 105: Reagents inside a well on the source well plate (101); 171: Camera (such as an electronic camera) used to provide physical registration (positioning) and 172: Surface mark fixed on the solid support (102) to provide a reference position on the solid support. FIG. 7B shows another example where an inkjet device 180 (e.g., piezoelectric) can be used to dispense droplets.

As illustrated in FIGS. 7A and 7B, a mechanical wave actuated dispenser (103, FIG. 7A, 180, FIG. 7) can be used to create traveling droplets (106) from a reagent source (101). The created traveling droplets (106) can be deposited onto a receiving surface, in this case a solid support (102). The position of the deposited droplets (111) on the solid support (102) can be controlled by the relative position of 101 and 102. Furthermore, there can be an existing pattern of molecules (110) on the solid support (102). The traveling droplets (106) can be aligned to the existing pattern on the surface. One should appreciate that the alignment and the dispensing are crucial steps in some embodiments. Multiple reagents can be dispensed to the sites on the surface in a sequential process. The solid support (102) is also known as the destination surface. This surface may have molecules that are previously deposited on the surface. These molecules can represent a complex pattern on the surface of (102). These molecules may be covalently bonded, hydrogen bonded, or not bonded (just deposited in solution or dry form) to the surface of (102). In a preferred embodiment, the droplets (106) created by the mechanical wave actuated dispenser (103, 180) are aimed and deposited at desired positions on the surface of 102. Adjacent surface droplets (111) can be combined by the creation of "merger" droplets (112) by positioning the merger droplets (112) in between or around the surface droplets (111). In this embodiment, the alignment of the droplets (106) to the solid support (102) and the molecules attached to the solid support (110) is crucial. A system can be devised to align the droplet to the patterns (molecules) on 102 by using a variety of sensing methods. In some embodiments, the position of the dispensed droplet in relation to the existing pattern on 102 is known or determinable by the user. The detection method and devices can be based on acoustics, electrical conductive, electric capacitive, or optical sensors.

In FIG. 7A, the alignment is illustrated using an optical setup. A set of test droplets (170) can be dispensed to several locations on the solid support (102) dispensed for the purpose of alignment of the droplet to the solid attached molecules (111). The relative position between the test droplets (170) and fixed registration marks (172: a surface mark fixed on the solid support (102) to provide a reference position on the solid support) on the surface of 102 can provide information on the alignment between the source plate (101) and the destination surface (102). A computer system can be used to calculate a set of correction (offset) parameters, which will be used to correct the alignment by adjusting the positioning motors controlling the position of 101, 102, and 103.

One should appreciate that when manipulating small liquid volumes such as picoliters and nanoliters, the smaller the droplet, the faster it will evaporate. Therefore, aspects of the invention relate to methods and devices to limit, retard or prevent water evaporation. In some embodiments, the discrete features or a subset of discrete features can be coated with a substance capable of trapping or capturing water. In other embodiments, the water-trapping material can be spin-coated onto the support. Different materials or substances can be used to trap water at specific locations. For example, the water trapping substance may be an aqueous matrix, a gel, a colloid or any suitable polymer. In some embodiments, the material is chosen to have a melting point that allows the material to remain solid or semi-solid (e.g. gel) at the reaction temperatures such as denaturing temperatures or thermocycling temperatures. Water trapping materials include but are not limited to colloidal silica, peptide gel, agarose, solgel and polydimethylsiloxane. In an exemplary embodiment, Snowtex® colloidal silica (Nissan Chemical) may be used. Snowtex colloidal silica is composed of mono-dispersed, negatively charged, amorphous silica particles in water. Snowtex colloidal silica can be applied as dry gel or as an hydrated gel onto the surface. In a preferred embodiment, the water trapping substance is spotted at discrete features comprising surface-bound oligonucleotides. Alternatively, oligonucleotides can be synthesized on the particles or nanoparticles (e.g. colloidal particles, Snowtex colloidal silica) and the particles or nanoparticles can be dispensed to the discrete features of the surface. In some embodiments, the water trapping substance is spotted on the discrete features of the support using a mechanical device, an inkjet device or an acoustic liquid handler.

One should appreciate, that evaporation can also be limited by forming a physical barrier between the surface of the droplet and the atmosphere. For example, a non-miscible solution can be overlaid to protect the droplet from evaporation. In some embodiments, a small volume of the non-miscible solution is dispensed directly and selectively at discrete location of the substrate such as features comprising a droplet. In some other embodiments, the non-miscible solution is dispensed onto a subset of features comprising a droplet. In other embodiments, the non-miscible solution is applied uniformly over the surface of the array forming a non-miscible bilayer in which the droplets are trapped. The non-miscible bilayer can then be evaporated to form a thin film over the surface or over a substantial part of the surface of the droplet. The non-miscible solution includes, but is not limited to, mineral oil, vegetable oil, silicone oil, paraffin oil, natural or synthetic wax, organic solvent that is immiscible in water or any combination thereof. One skilled in the art will appreciate that depending on the composition of the oils, some oils may partially or totally solidify at or below room temperature. In some embodiments, the non-miscible solution may be a natural or synthetic wax such as paraffin hydrocarbon. Paraffin is an alkane hydrocarbon with the general formula $CnH2n+2$. Depending on the length of the molecule, paraffin may appear as a gas, a liquid or a solid at room temperature. Paraffin wax refers to the solids with $20 \leq n \leq 40$ and has a typical melting point between about 47° C. to 64° C. Accordingly, in some embodiments, the support may be stored capped with a wax. Prior to use, heat may be applied to the support to allow the wax to turn into a liquid wax phase coating the support.

In some aspects of the invention, in subsequent steps, a solvent or an aqueous solution may be added to the droplet having a non-miscible solution at its surface. Aqueous solution may be added, for example, to initiate a reaction, to adjust a volume, to adjust a pH, to increase or decrease a solute concentration, etc. . . . One would appreciate that the aqueous solution can penetrate the non-miscible layer using different mechanisms. For example, if using an inkjet head device, the aqueous solution is ejected and the physical momentum of the ejected droplet will enable the aqueous solution to cross the non-miscible layer. Other mechanisms may employ additional forces, such as for example magnetic and/or electrostatic forces and/or optical forces. The optical and magnetic forces can be created simultaneously or independently of one another. Furthermore, the mechanism can utilize coupled magneto-optical tweezers. In some embodiments, the aqueous solution to be dispensed contains magnetic nanoparticles and a magnetic force can be used to help penetration of the non-miscible layer. Alternatively, the aqueous solution carries an electrostatic charge and an external applied electric field can be used to achieve penetration of the non-miscible layer.

Yet, in another aspect of the invention, the size of the droplet is continuously or frequently monitored. One should appreciate that the size of the droplet is determined by the volume and by the surface tension of the solution. Accordingly, loss of volume can be detected by a decrease of the droplet footprint or radius of the droplet footprint. For example, using an optical monitoring system, through a microscope lens and camera system, the size or footprint of the droplet can be determined and the volume of the droplet can be calculated. In some embodiments, the volume of the droplet or the radius of the droplet is monitored every second or every millisecond. One would appreciate that the magnitude of the evaporation rate of the solvent (e.g. water) from the droplet of interest depends in part on the temperature and thus increases with increasing temperatures. For example, during amplification by thermocycling or during denaturation of the double-stranded complexes, increase of temperature will result in the rapid evaporation of the droplet. Therefore, the volume of the droplet can be monitored more frequently and the droplet volume can be adjusted by re-hydration more frequently. In the event of volume fluctuation such as loss of volume, sub-pico to nano volumes of solvent (e.g. water) can be dispensed onto the droplet or to the discrete feature comprising the droplet. Solvent or water volumes of about 0.5 pL, of about 1 pL, of about 10 pL, of about 100 pL, of about 1 nL, of about 10 nL, of about 100 nL can be dispensed this way. Solvent or water volumes may be delivered by any conventional delivery means as long that the volumes are controlled and accurate. In a preferred embodiment, water is dispensed using an inkjet device. For example, a typical inkjet printer is capable of producing droplets volumes ranging from about 1.5 pL to about 10 pL, while other commercial ultrasonic dispensing techniques can produce droplets volumes of about 0.6 pL. In some embodiments, water is added in a rapid series of droplets. In some embodiments, water is dispensed when registering a loss of volume of more than 10%, of more than 25%, of more than 35%, of more than 50%.

In another embodiment, the evaporation rate can be limited by adding a compound having a high boiling point component to the droplet(s) of interest, provided that the presence of the compound does not inhibit the enzymatic reactions performed on the substrate. The boiling point of a liquid is the temperature at which the liquid and vapor phases are in equilibrium with each other at a specified pressure. When heat is applied to a solution, the temperature of the solution rises until the vapor pressure of the liquid equals the pressure of the surrounding gases. At this point, vaporization or evaporation occurs at the surface of the solution. By adding a high boiling point liquid to the droplet of interest, evaporation of the water content of a droplet may be substantially reduced (see U.S. Pat. No. 6,177,558). In some embodiment, the high boiling point solution is a solvent. In some embodiments, the high boiling point liquid has a boiling point of at least 100° C., at least 150° C., at least 200° C. In some embodiments, glycerol is added to the solution, increasing the boiling point. Accordingly, the solution containing the high boiling point liquid will evaporate at a much slower rate at room temperature or at reaction conditions such as thermocycling, extension, ligation and denaturation.

In other embodiments, evaporation rate is limited by raising the vapor rate or humidity surrounding the droplet. This can be performed, for example, by placing "sacrificial" droplets around or in close proximity to the droplet of interest (e.g. around or in close proximity of a droplet comprising the oligonucleotides) (see for example, Berthier E. et al., Lab Chip, 2008, 8(6):852-859).

Figure 23:
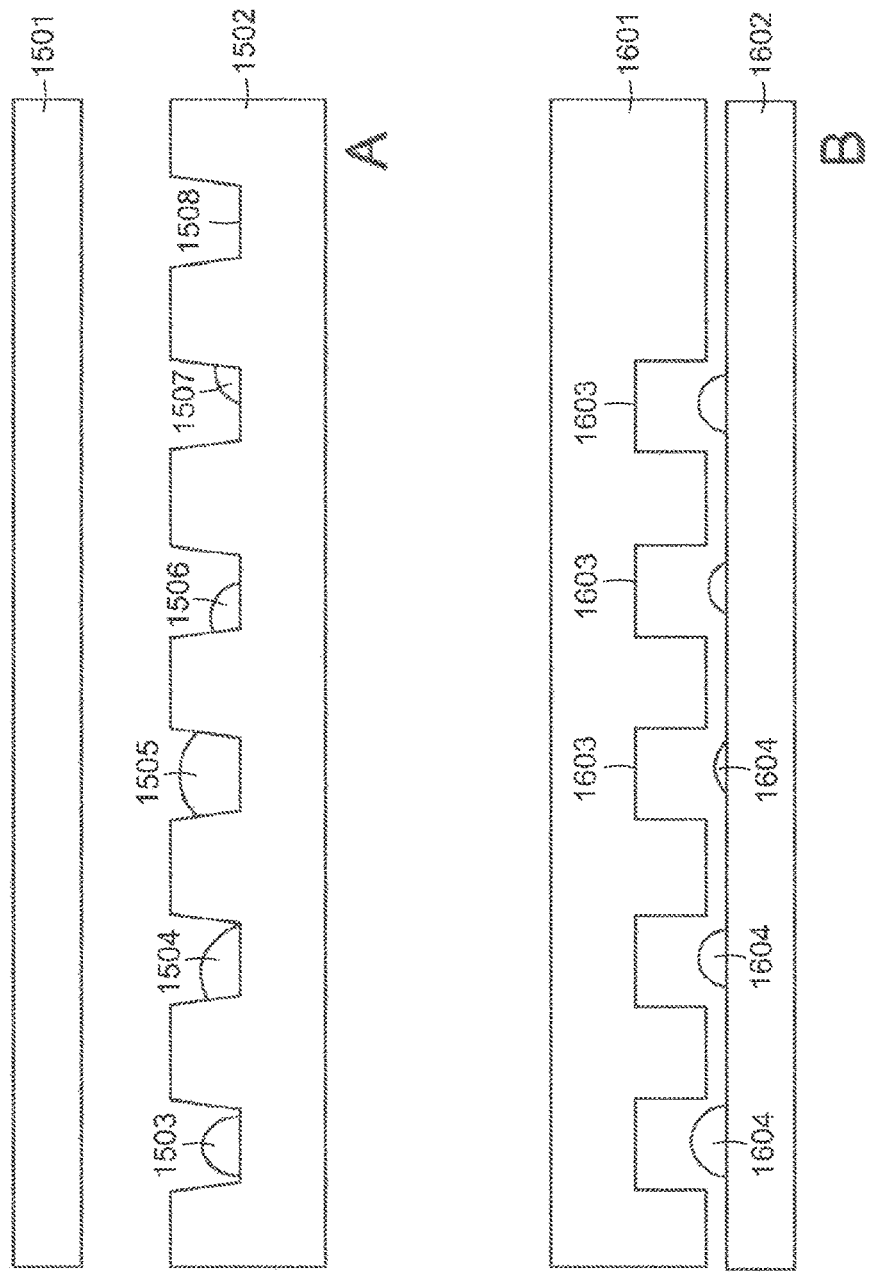
FIG. 23 illustrate non-limiting embodiments of a microvolume sealed plate device to control humidity.

Some aspects of the invention relate to devices to control the humidity and/or the evaporation rate. In some embodiments, the surface or solid support is enclosed in a closed container to limit the evaporation. FIG. 23A and FIG. 23B illustrate non-limiting embodiments of a microvolume sealed plates. Referring to FIG. 23A, a substrate or support (1502) is provided, the substrate having defined features (1508) such that volumes of reactions (1503, 1504, 1505, 1506, 1507) can be deposited in such features via, for example, an inkjet and inkjet-like liquid dispensing technology. A lid (1501) is used to seal such reaction volumes by either applied pressure or using a lid (1501) with a pressure-sensitive adhesive on the contacting side to the substrate (1502). In some embodiments, the density of these features can be at least 10 features per $cm^2$, at least 100 features per $cm^2$, at least 1,000 features per $cm^2$, at least 10,000 features per $cm^2$, at least 100,000 features per $cm^2$, at least 1,000,000 features per $cm^2$. The features (1508) can have diameter (width and length) dimensions from less than about 1 cm, less than about 1 mm, less than about 1 μm. The depth of the features can have dimensions from less than about 1 cm, less than about 1 mm, less than about 1 μm. The width, length, and depths of the features can differ from feature to feature. The features geometry can be complex, including lines, spirals, bends (at all possible angles from 0.01 degrees to 179.99 degrees) or any combination of such complex geometries.

In another embodiment, the substrate is flat (1602) with reaction volumes (e.g. droplets 1604) set up on a surface of the substrate. The lid (1601) is designed to have features that form containers or vessels for reaction volumes (1604). The reaction volumes (1604) can be created on the substrate (1602) using inkjet and inkjet-like liquid manipulation technologies. The lid (1601) can be sealed against the substrate (1602) by either applied pressure or using a lid (1601) or substrate (1602) with a pressure-sensitive adhesive on the contacting side to the substrate (1602).

Figure 24:
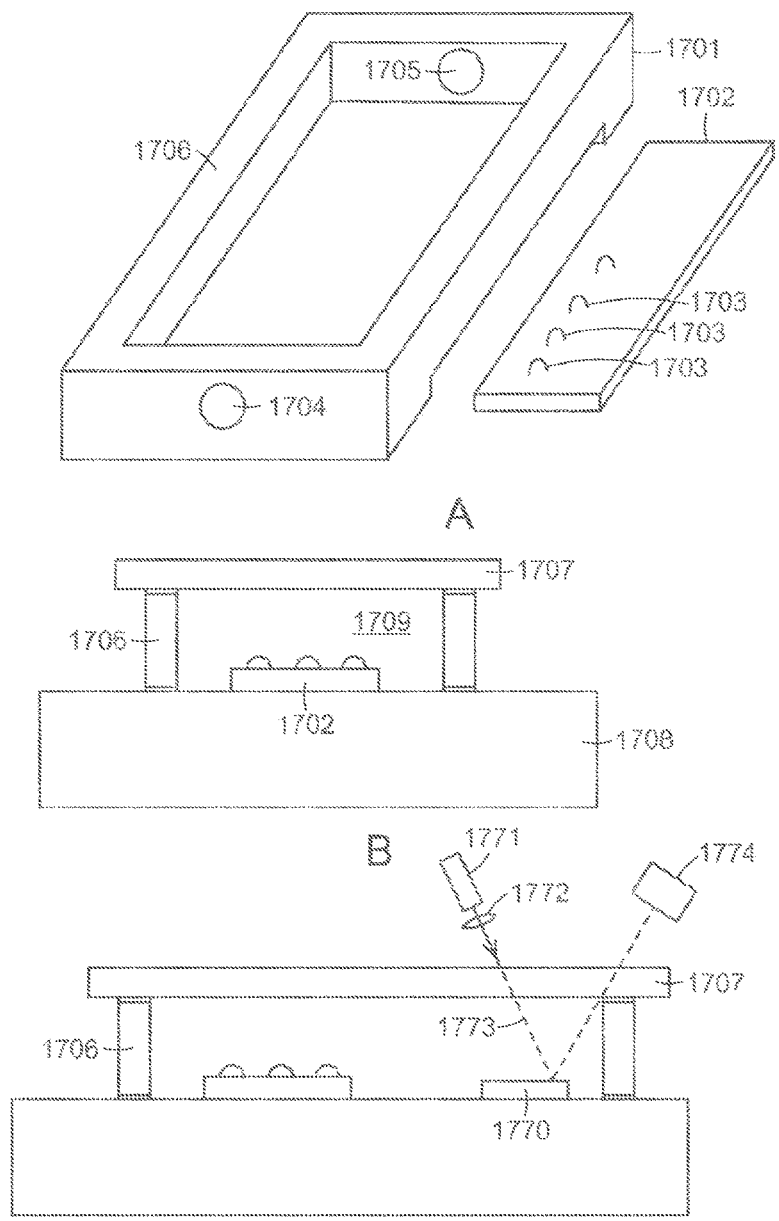
FIG. 24 illustrate non-limiting embodiments of a feedback controlled humidity chamber.

Aspects of the invention relate to feedback controlled humidity devices, systems and methods. In some embodiments, the device comprise a confinement chamber structure. Referring to FIG. 24A, a volume (1709) of a mixture of different gases, such oxygen, nitrogen, argon, helium, water vapor, solvent vapor, and any other desirable gases, can be maintained inside a confinement chamber structure (1701) consisting of walls (1706). In some embodiments, openings (1705) on the wall (1706) allow introduction and removal of different components of the gases to achieve the desired composition of the gas mixture in the volume (1709). Additional openings (1704) can be used to serve as measurement or sampling ports to examine the condition or composition of the gas in the volume. A substrate (1702) carrying small reaction volumes (e.g. droplets 1703) deposited by, for example, an inkjet or inkjet-like liquid dispensing technology can be placed inside the chamber's volume (1709).

The chamber's volume can be further confined by a lid (1707). In some embodiments, the lid is temperature controlled. The lid can be made of a material that is optically transparent, such as glass. The heating of the lid can be accomplished via an electrically conductive layer of Indium in Oxide (ITO), and heated via Ohmic heating. Other heating or cooling methods are also possible, for example, via forced fluid flow. The chamber's volume can be further confined by a bottom (1708). In some embodiment, the bottom is temperature controlled. In some embodiments, the volume (1709) is modulated to contain an environment that has the exact molar ratio of different gas mixtures. In a preferred embodiment, the molar ratio of water vapor and carrier gas (air, helium, argon, nitrogen, or any other desirable gas, including solvent vapors) can be controlled, together with the temperature of the volume (1709), to allow an equilibrium between water or solvent evaporation and condensation on the surface of the substrate (1702). This equilibrium allows the reaction volumes (1703) on the substrate (1702) to be maintained at the desirable steady volume over an appropriate period of time. The appropriate period of time can be in the range of seconds, minutes, hours or days. One skilled in the art would appreciate that the droplets volumes can be maintained, decreased or increased by controlling evaporation and/or condensation. For example evaporation of the reaction volumes (1703) on the substrate is induced to, for example, achieve and/or control sample concentration and/or decrease the reaction volumes. Yet in other embodiments, condensation of the reaction volumes (1703) on the substrate is induced to, for example, achieve and/or control sample dilution and/or increase reaction volumes. One would appreciate that it is important to control condensation when increasing reaction volumes. In some embodiments, condensation can be controlled by periodic humidity compensation. For example, by increasing the temperature on the substrate and/or lowering the humidity in the chamber, evaporation can be induced over a short period of time (in the range of ms, s or min). The evaporation of small satellite droplets (e.g. off target droplets) will take place before evaporation of larger droplets (e.g. reaction volumes). Since the evaporation rate (by volume) is proportional to droplets' surface areas, and smaller droplets having higher surface-to-volume ratio evaporate first. In other embodiments, condensation may be controlled by controlling substrate's surface properties such as hydrophilicity/hydrophobicity. One skilled in the art will appreciate that condensation or droplet growth is characterized by nucleation of the droplet at nucleation sites. The rate of nucleation is a function of the surface tension and the wetting angle. Accordingly, surfaces promoting nucleation have a wetting-contact angles greater than zero. In some embodiments, condensation can be controlled by designing off-target areas on the surface (such as interfeatures) having surface properties impairing nucleation. For example, the substrate's surface can be treated so that off target areas are more hydrophobic than areas where droplet growth is desired. In other embodiments, the off-target areas surfaces are designed to be smooth so that no nucleation is reduced.

In some aspects of the invention, the reaction volumes are controlled via a feedback control. In some embodiments, one or more monitoring isolated volumes (e.g. monitoring droplets) are used to monitor a plurality of isolated reaction volumes (e.g. droplets comprising predefined oligonucleotide sequences) on a support. In some embodiments, a first support is provided which comprises a plurality of reaction droplets and a second support is provided comprising at least one monitoring droplet. Preferably, the at least one monitoring droplet has an identical surface-to-volume ratio than at least one of the reaction droplet of interest and an identical solvent composition. Accordingly, modification of the reaction volume of the monitoring droplet is indicative of the modification of volume of the at least one droplet of interest. In some embodiments, the reaction droplets and monitoring droplets are placed on the same support.

Figure 25:
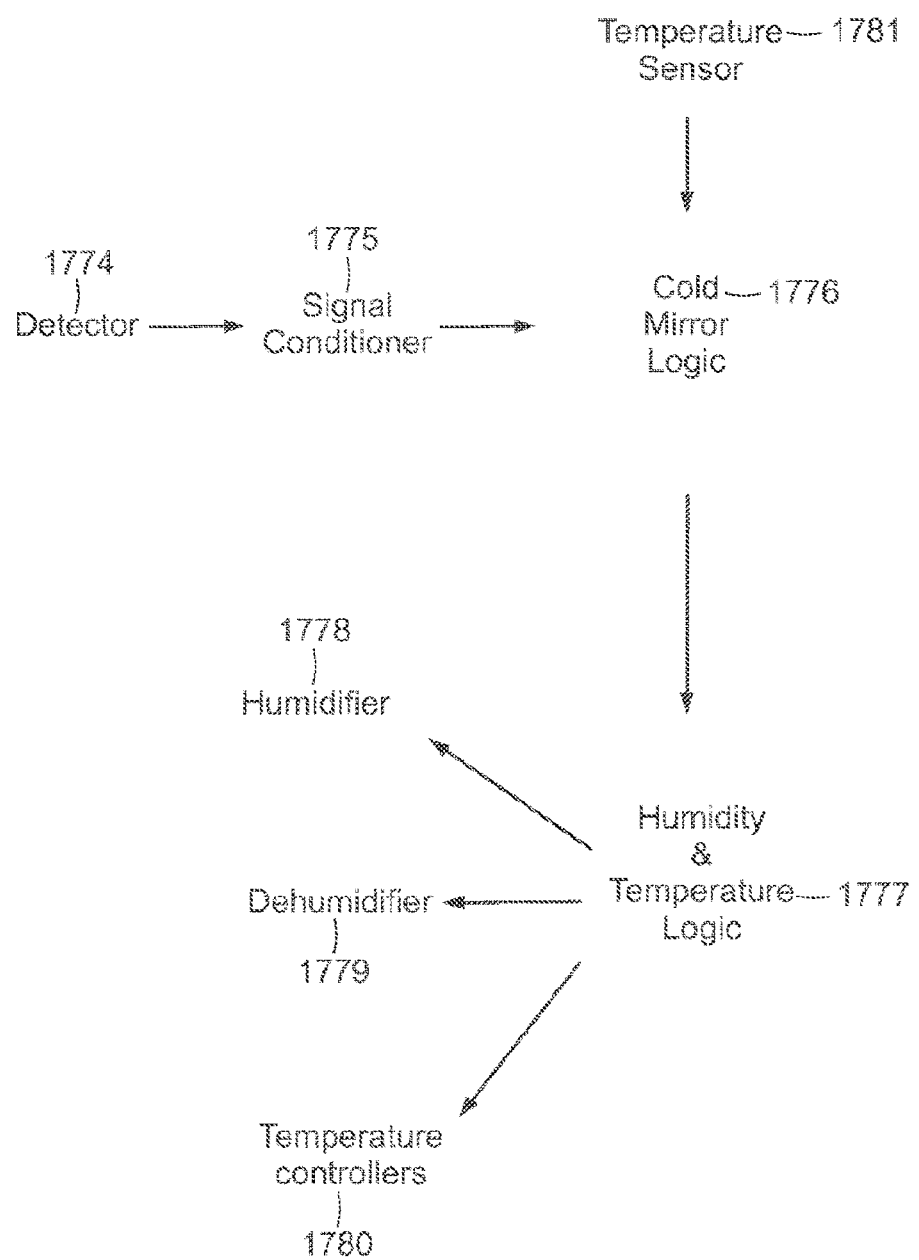
FIG. 25 illustrates a non-limiting embodiment of a control loop humidity system.

In some embodiments, the molar ratio of the mixture of gases is measured using a cold mirror setup. As illustrated in FIG. 24C, an optically reflective surface (1770) can be placed on the bottom surface (1708), next to the substrate (1702). The mirror can be of a similar material and similar thickness to the substrate (1702) to best mimic the thermal behavior of the substrate. The reflective surface on the mirror (1770) can be on the top surface or on the bottom surface. In some embodiments, the mirror (1770) is placed on the same substrate (1702) as the reaction volumes. In some embodiments areas on the substrate can be made to act as mirrors to provide multiple measurement locations on the substrate (1702). An optical assembly, consisting of a source (1771), optical train (1772), and a detector (1774) can be placed outside of the chamber's volume (1709). In some embodiments, measure of the fogging or condensation of water fine water droplets onto a mirror is used to measure the condensation or the evaporation rate. Condensation condition on the mirror (1770) can be detected by measuring the intensity of the optical beam (1773) reflected off the surface. The beam (1773) can be modulated in time and wavelength, via the modulation of the source (1771) to achieve higher signal to noise ratios. In preferred embodiments, the system comprises a control loop. In an exemplary embodiment, and as depicted in FIG. 25, the control loop consists of a detector (1774) which feeds measured optical intensities to a signal conditioning circuit (1775). The output of the signal conditioning circuit (1775) is used by the cold mirror logic (1776) to determine the condensation state on the mirror, and calculate molar ratio of the mix of gases in the volume (1709) using other inputs such as temperature, pressure etc. The system comprises a temperature sensor (1781), pressure sensor (not shown), and/or any other suitable sensors. The humidity and temperature logic (1777) determines the actuation of humidifier (1778), dehumidifier (1779), and/or temperature controllers (1780) to effectuate the desirable conditions determined by the cold mirror logic (1776).

In some embodiments, the reaction volumes (1703) contain the necessary reagents to allow enzyme mediated biochemical reactions to take place between the molecular population inside the reaction volume (e.g. droplet) and the molecular population present on the wetted surface in contact with the reaction volume. One would appreciate that the reaction volume can be used to carry out a variety of reactions including, but no limited to, amplification, hybridization, extension, ligation, sequencing, in-vitro transcription, in-vitro translation, or any other reaction of interest. The molecular population may contain nucleic acids, DNA, RNA, oligonucleotides, proteins, dNTPs, salts, buffer components, detergents, and/or any other appropriate component. The reaction volume may comprises an enzyme, such as a polymerase, a ligase, a CEL1-like endonuclease, a nuclease, mixtures of such enzymes, and/or any other appropriate enzymes. In some embodiments, the products of the enzyme mediated biochemical reaction can include contain nucleic acids, DNA, RNA, oligonucleotides, proteins, labeled nucleic acids, amplified nucleic acid (e.g. clonal amplification of a selected population of nucleic acid), assembled nucleic acids etc.

In some aspects of the invention, the reagents in the reaction volumes promote oligonucleotide or polynucleotide assembly. In some embodiments, the reaction volumes may contain two or more populations of single-stranded oligonucleotides having predefined sequences in solution. The populations of oligonucleotides can hybridize to a single-stranded oligonucleotide attached to the wetted surface thereby forming double-stranded hybrids or duplexes attached to the surface. In some embodiments, the double-stranded hybrids contain breaks and gaps in the phosphodiester backbone, formed at the junctions of different oligonucleotide populations. In some embodiments, a polymerase and dNTPs and other necessary components are added to fill the gaps in the backbone. In other embodiments, a ligase and other necessary components are added to mend breaks in the backbone.

In other embodiments, the reaction volumes may contain two or more populations of oligonucleotides in solution, each population of oligonucleotide having predefined sequence. In some embodiments, the each population of oligonucleotide has a sequence complementary to an another population of oligonucleotides. In this manner, the populations of oligonucleotides can hybridize to form double stranded hybrids or duplexes in solution. The hybrids may contain breaks and gaps in the phosphodiester backbone, formed at the junctions of different oligonucleotide populations. In some embodiments, a polymerase and dNTPs and other necessary components are added to fill the gaps in the backbone. In other embodiments, a ligase and other necessary components are added to mend breaks in the backbone.

Aspects of the invention provide methods for the amplification of one or more single-stranded oligonucleotide on the support. Oligonucleotides may be amplified before or after being detached from the support and/or eluted in a droplet. Preferably, the oligonucleotides are amplified on the solid support. One skilled in the art will appreciate that oligonucleotides that are synthesized on solid support will comprise a phosphorylated 3' end or an additional 3'-terminal nucleoside (e.g. T). The 3'-phosphorylated oligonucleotides are not suitable for polynucleotide assembly as the oligonucleotides cannot be extended by polymerase. In preferred aspects of the invention, the oligonucleotides are first amplified and the amplified products are assembled into a polynucleotide. Accordingly, aspect of the invention provides methods wherein a set or subset of oligonucleotides, that are attached to at a set of subset of features of the support, are amplified by locally delivering sub-microvolumes at addressable discrete features. The term "amplification" means that the number of copies of a nucleic acid fragment is increased. As noted above, the oligonucleotides may be first synthesized onto discrete features of the surface, may be deposited on the substrate or may be deposited on the substrate attached to nanoparticles. In a preferred embodiment, the oligonucleotides are covalently attached to the surface or to nanoparticles deposited on the surface. In an exemplary embodiment, locations or features comprising the oligonucleotides to be amplified are first selected. In a preferred embodiment, the selected features are in close proximity to each others on the support. Aqueous solution is then deposited on the selected feature thereby forming a droplet comprising hydrated oligonucleotides. One would appreciate that each droplet is separated from the other by surface tension. In some embodiments, the solution can be water, buffer or a solution promoting enzymatic reactions. In an exemplary embodiment, the solution includes, but is not limited to, a solution promoting primer extension. For example, the solution may be composed of oligonucleotides primer(s), nucleotides (dNTPs), buffer, polymerase and cofactors. In other embodiments, the solution is an alkaline denaturing solution. Yet, in other embodiments, the solution may comprise oligonucleotides such as complementary oligonucleotides.

In some embodiments, oligonucleotides or polynucleotides are amplified within the droplet by solid phase PCR thereby eluting the amplified sequences into the droplet. In other embodiments, oligonucleotides or polynucleotides are first detached form the solid support and then amplified. For example, covalently-attached oligonucleotides are translated into surface supported DNA molecules through a process of gaseous cleavage using amine gas. Oligonucleotides can be cleaved with ammonia, or other amines, in the gas phase whereby the reagent gas comes into contact with the oligonucleotide while attached to, or in proximity to, the solid support (see Boal et al., Nucl. Acids Res, 1996, 24(15): 3115-7), U.S. Pat. Nos. 5,514,789; 5,738,829 and 6,664, 388). In this process, the covalent bond attaching the oligonucleotides to the solid support is cleaved by exposing the solid support to the amine gas under elevated pressure and/or temperature. In some embodiments, this process may be used to "thin" the density of oligonucleotides at specific features.

One skilled in the art will appreciate that releasing oligonucleotides from the solid support can be achieved by a number of different techniques which will depend on the technique used to attach or synthesize the oligonucleotides on the solid support. Preferably, the oligonucleotides are attached or synthesized via a linker molecule and subsequently detached and released. In some embodiments, a plurality of oligonucleotides may be attached or synthesized to the support, cleaved at a cleavable linker site and released in solution. For example, U.S. Pat. No. 7,563,600 discloses a cleavable linker having a succinate moiety bound to a nucleotide moiety such that the cleavage produces a 3'-hydroxy-nucleotide. The succinate moiety is bound to solid support through an ester linkage by reacting the succinate moieties with the hydroxyl on the solid support. US patent application discloses sulfonyl cleavable linkers comprising a linker hydroxyl moiety and a base-labile cleaving moiety. A phosphorous-oxygen bond is formed between phosphorous of the sulfonyl amidite moieties and oxygen of the hydroxyl groups at known location of the support. In some embodiments, the oligonucleotides are attached or synthesized using a photo-labile linker (see for example Tosquellas et al., Nucl. Acids Res., 1998, Vol. 26, pp 2069-2074). In some instances, the photolabile linker can be rendered labile by activation under an appropriate chemical treatment. For example, U.S. Pat. No. 7,183,406 discloses a safety-catch linker which is stable under the oligonucleotide synthesis conditions and that is photolabile after treatment with trifluoroacetic acid. Oligonucleotides linked with a photo-labile linker can then be released by photolysis. Using photolabile linkers, it is therefore possible to selectively release in solution (e.g. in a droplet) specific oligonucleotides at predetermined features. The oligonucleotides released in solution may then be brought into contact for further processing (hybridization, extension, assembly, etc. . . . ) by merging droplets of moving the oligonucleotides from one feature to a next feature on a solid support.

One skilled in the art will appreciate that DNA microarrays can have very high density of oligonucleotides on the surface (approximately 108 molecules per feature), which can generate steric hindrance to polymerases needed for PCR. Theoretically, the oligonucleotides are generally spaced apart by about 2 nm to about 6 nm. For polymerases, a typical 6-subunit enzyme can have a diameter of about 12 nm. Therefore the support may need to be custom treated to address the surface density issue such that the spacing of surface-attached oligonucleotides can accommodate the physical dimension of the enzyme. For example, a subset of the oligonucleotides can be chemically or enzymatically cleaved, or physically removed from the microarray. Other methods can also be used to modify the oligonucleotides such that when primers are applied and annealed to the oligonucleotides, at least some 3' hydroxyl groups of the primers (start of DNA synthesis) are accessible by polymerase. The number of accessible 3' hydroxyl groups per spot can be stochastic or fixed. For example, the primers, once annealed, can be treated to remove some active 3' hydroxyl groups, leaving a stochastic number of 3' hydroxyl groups that can be subject to chain extension reactions. In another example, a large linker molecule (e.g., a concatamer) can be used such that one and only one start of synthesis is available per spot, or in a subset of the oligonucleotides per spot.

Figure 8:
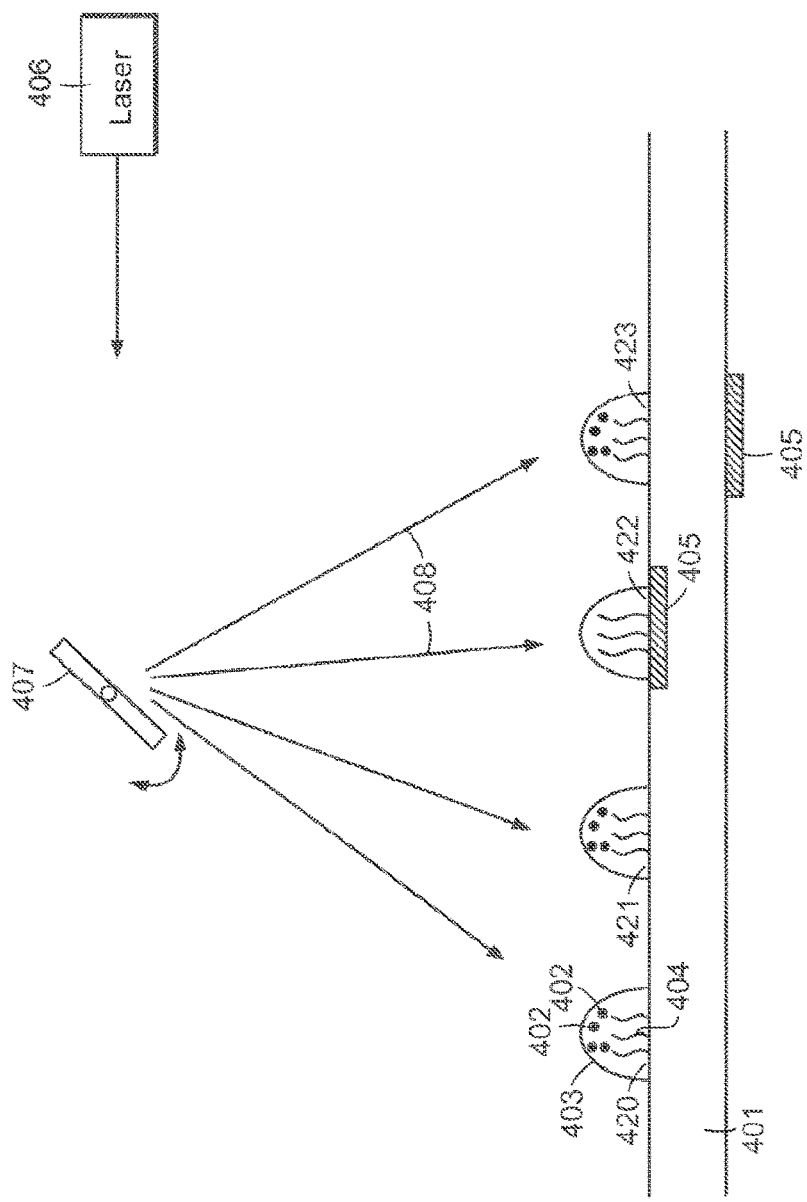
FIG. 8 illustrates an embodiment of thermal control device and procedure comprising solid support substrate (401) comprising immobilized molecules (404); an optical absorbent material (402) in the surface droplet (403), the surface droplet comprising molecules (409) in solution, an optical absorbent material (405) on the surface of 401, an optical energy source (406), a scanning setup (407), energy beams (408) and a plurality of reaction sites (420, 421, 422, 423).

According to some aspects of the invention, hydrated oligonucleotides can be amplified within the droplet, the droplet acting as a virtual reaction chamber. In some embodiments, the entire support or array containing the discrete features is subjected to amplification. In other embodiments, one or more discrete features are subjected to amplification. Amplification of selected independent features (being separated from each others) can be performed by locally heating at least one discrete feature. Discrete features may be locally heated by any means known in the art. For example, the discrete features may be locally heated using a laser source of energy that can be controlled in a precise x-y dimension thereby individually modulating the temperature of a droplet. In another example, the combination of a broader beam laser with a mask can be used to irradiate specific features. In some embodiments, methods to control temperature on the support so that enzymatic reactions can take place on a support (PCR, ligation or any other temperature sensitive reaction) are provided. In some embodiments, a scanning laser is used to control the thermocycling on distinct features on the solid support. The wavelength used can be chosen from wide spectrum (100 nm to 100,000 nm, i.e. from ultraviolet to infrared). In some embodiments, the feature on which the droplet is spotted comprises an optical absorber or indicator. In some other embodiments, optical absorbent material can be added on the surface of the droplet. In some embodiments, the solid support is cooled by circulation of air or fluid. The energy to be deposited can be calculated based on the absorbance behavior. In some embodiments, the temperature of the droplet can be modeled using thermodynamics. The temperature can be measured by an LCD like material or any other in-situ technology. In some embodiments, the solid support is cooled by circulation of air or fluid. For example, the whole support can be heated and cooled down to allow enzymatic reactions to take place. One method to control the temperature of the surface droplets is by using a scanning optical energy deposition setup as shown in FIG. 8. An energy source (406) can be directed by a scanning setup 407 to deposit energy at various locations on the surface of the solid support 401 comprising attached or supported molecules (404). Optical absorbent material (402, 405) can be added on the surface of the solid support or on the surface of droplet. Optical energy source, such as a high intensity lamp, laser, or other electromagnetic energy source (including microwave) can be used. The temperature of the different reaction sites (420, 421, 422, 423, . . . ) can be controlled independently by controlling the energy deposited at each of the features.

For example, a Digital Micromirror Device (DMD) can be used for temperature control. DMD is an optical semiconductor. See, for example, U.S. Pat. No. 7,498,176. In some embodiments, a DMD can be used to precisely heat selected features or droplets on the solid support. The DMD can be a chip having on its surface several hundred thousand microscopic mirrors arranged in a rectangular array which correspond to the features or droplets to be heated. The mirrors can be individually rotated (e.g., ±10-12°), to an on or off state. In the on state, light from a light source (e.g., a bulb) is reflected onto the solid support to heat the selected spots or droplets. In the off state, the light is directed elsewhere (e.g., onto a heatsink). In one example, the DMD can consist of a 1024×768 array of 16 μm wide micromirrors. These mirrors can be individually addressable and can be used to create any given pattern or arrangement in heating different features on the solid support. The features can also be heated to different temperatures, e.g., by providing different wavelengths for individual spots, and/or controlling time of irradiation.

Figure 9:
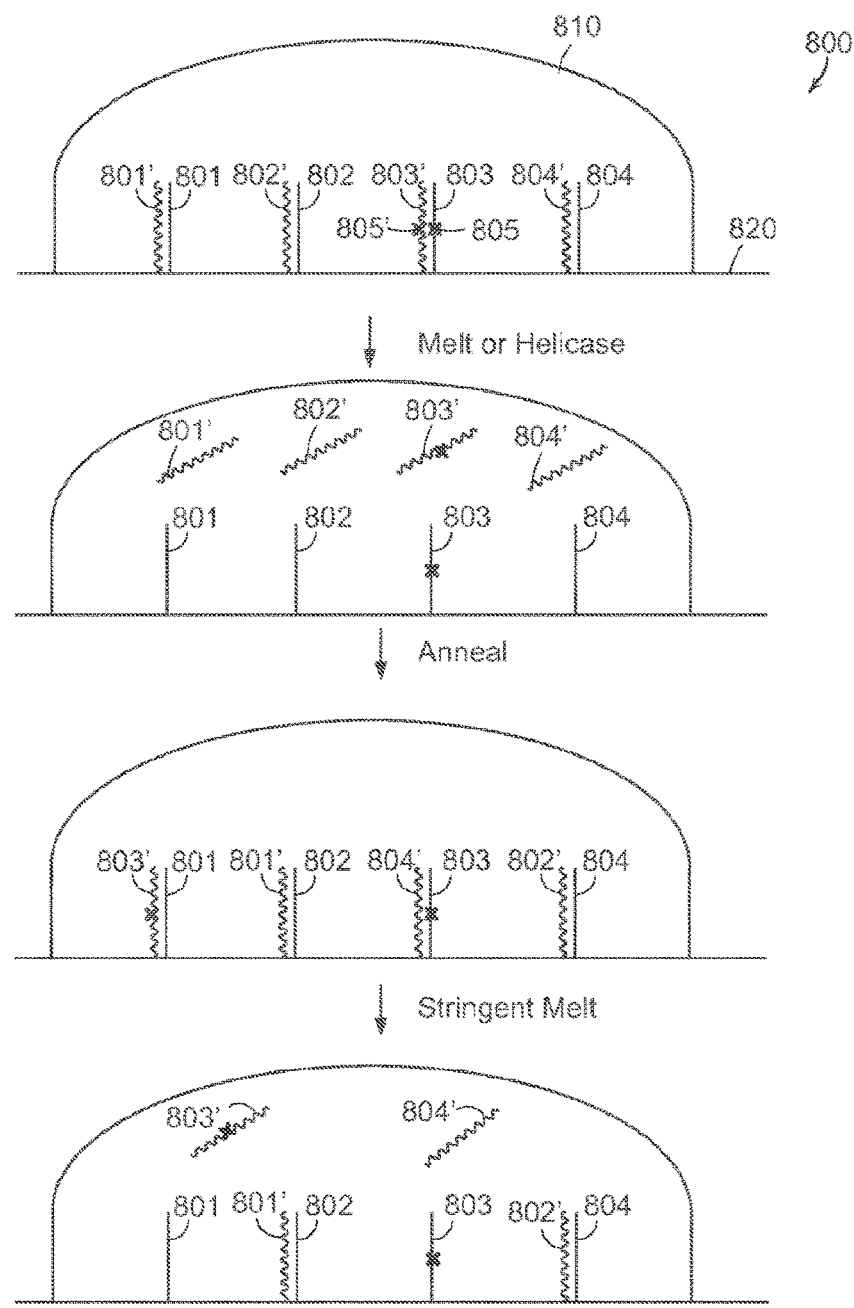
FIG. 9 illustrates an exemplary method of error filtration.

One would appreciate that amplification occurs only on features comprising hydrated template oligonucleotides (i.e. local amplification at features comprising a droplet volume). Different set of features may be amplified in a parallel or sequential fashion with parallel or sequential rounds of hydrating (i.e. dispensing a droplet volume on a specific feature), amplifying oligonucleotides and drying the set of features. In some embodiments, the support is dried by evaporating liquid in a vacuum while heating. Thus, after each round of amplification, the support will comprise a set of droplets containing oligonucleotides duplexes. The complementary oligonucleotides can be released in solution within the droplet and be collected. Alternatively, complementary oligonucleotides may be dried onto the discrete features for storage or further processing. Yet, complementary oligonucleotides can be subjected to further reactions such as error filtration and/or assembly. In some embodiments, a different set or subset of features can then be hydrated and a different set or subset of template oligonucleotides can be amplified as described herein. For example, a droplet 810, as illustrated in FIG. 9, can be dispensed (e.g., inkjetted) on a support 800. The droplet 810 can contain various reagents such as enzymes, buffers, dNTPs, primers, etc. The droplet 810 covers a discrete feature 820 (a feature corresponding to a predefined sequence) on the support 800. For purpose of illustration only, four oligonucleotides, 801, 802, 803, 804 are shown, while many more oligonucleotides having the same sequence are also present on feature 820 but not shown. PCR can be carried out to synthesize oligonucleotides 801', 802', 803', 804' complementary to template oligonucleotides 801, 802, 803, 804 that are attached to feature 820. In the case of the enzymatic amplification, the solution includes but is not limited to primers, nucleotides, buffers, cofactors, and enzyme. For example, an amplification reaction includes DNA polymerase, nucleotides (e.g. dATP, dCTP, dTTP, dGTP), primers and buffer.

In some embodiments, a selected set of features may be protected from hydration by using an immiscible fluid system. An immiscible fluid system, such as oil and aqueous reagents, can be used to achieve passivation of sites on which reactions take place. As shown in FIG. 22, a droplet of oil (or a short chain hydrocarbon) can first be deposited on a site (403) where reaction is undesirable. After the oil deposition, subsequent fluid processing steps will affect only the unprotected sites or features (404), but not the protected sites or features (403) since the fluid (402), cannot reach the surface of the protected site (403). This concept can be further extended to allow controlled exposure or protection at the oil covered spots (403). By using electrowetting concepts, the shape of an oil droplet can be modulated by the appropriate application of electric field. The surface droplet shape can be modulated from its normal state (409) to its actuated state (410) by electrowetting or optoelectrowetting. The effect of such control allows the exposure of a portion or the totality of the feature (109) depending on the applied field.

In some embodiments, the oligonucleotides may comprise universal (common to all oligonucleotides), semi-universal (common to at least of portion of the oligonucleotides) or individual or unique primer (specific to each oligonucleotide) binding sites on either the 5' end or the 3' end or both. As used herein, the term "universal" primer or primer binding site means that a sequence used to amplify the oligonucleotide is common to all oligonucleotides such that all such oligonucleotides can be amplified using a single set of universal primers. In other circumstances, an oligonucleotide contains a unique primer binding site. As used herein, the term "unique primer binding site" refers to a set of primer recognition sequences that selectively amplifies a subset of oligonucleotides. In yet other circumstances, an oligonucleotide contains both universal and unique amplification sequences, which can optionally be used sequentially.

In some embodiments, primers/primer binding site may be designed to be temporary. For example, temporary primers may be removed by chemical, light based or enzymatic cleavage. For example, primers/primer binding sites may be designed to include a restriction endonuclease cleavage site. In an exemplary embodiment, a primer/primer binding site contains a binding and/or cleavage site for a type IIs restriction endonuclease. In such case, amplification sequences may be designed so that once a desired set of oligonucleotides is amplified to a sufficient amount, it can then be cleaved by the use of an appropriate type IIs restriction enzyme that recognizes an internal type IIs restriction enzyme sequence of the oligonucleotide. In some embodiments, after amplification, the pool of nucleic acids may be contacted with one or more endonucleases to produce double-stranded breaks thereby removing the primers/primer binding sites. In certain embodiments, the forward and reverse primers may be removed by the same or different restriction endonucleases. Any type of restriction endonuclease may be used to remove the primers/primer binding sites from nucleic acid sequences. A wide variety of restriction endonucleases having specific binding and/or cleavage sites are commercially available, for example, from New England Biolabs (Beverly, Mass.). In various embodiments, restriction endonucleases that produce 3' overhangs, 5' overhangs or blunt ends may be used. When using a restriction endonuclease that produces an overhang, an exonuclease (e.g., RecJf, Exonuclease I, Exonuclease T, S1 nuclease, P1 nuclease, mung bean nuclease, T4 DNA polymerase, CEL I nuclease, etc.) may be used to produce blunt ends. Alternatively, the sticky ends formed by the specific restriction endonuclease may be used to facilitate assembly of subassemblies in a desired arrangement. In an exemplary embodiment, a primer/primer binding site that contains a binding and/or cleavage site for a type IIs restriction endonuclease may be used to remove the temporary primer. The term "type-IIs restriction endonuclease" refers to a restriction endonuclease having a non-palindromic recognition sequence and a cleavage site that occurs outside of the recognition site (e.g., from 0 to about 20 nucleotides distal to the recognition site). Type IIs restriction endonucleases may create a nick in a double-stranded nucleic acid molecule or may create a double-stranded break that produces either blunt or sticky ends (e.g., either 5' or 3' overhangs). Examples of Type IIs endonucleases include, for example, enzymes that produce a 3' overhang, such as, for example, Bsr I, Bsm I, BstF5 I, BsrD I, Bts I, Mnl I, BciV I, Hph I, Mbo II, Eci I, Acu I, Bpm I, Mme I, BsaX I, Bcg I, Bae I, Bfi I, TspDT I, TspGW I, Taq II, Eco57 I, Eco57M I, Gsu I, Ppi I, and Psr I; enzymes that produce a 5' overhang such as, for example, BsmA I, Ple I, Fau I, Sap I, BspM I, SfaN I, Hga I, Bvb I, Fok I, BceA I, BsmF I, Ksp632 I, Eco31 I, Esp3 I, Aar I; and enzymes that produce a blunt end, such as, for example, Mly I and Btr I. Type-IIs endonucleases are commercially available and are well known in the art (New England Biolabs, Beverly, Mass.).

After amplification, the polymerase may be deactivated to prevent interference with the subsequent steps. A heating step (e.g. high temperature) can denature and deactivate most enzymes which are not thermally stable. Enzymes may be deactivated in presence (e.g. within the droplet) or in the absence of liquid (e.g. dry array). Heat deactivation on a dry support has the advantage to deactivate the enzymes without any detrimental effect on the oligonucleotides. In some embodiments, a non-thermal stable version of the thermally stable PCR DNA Polymerase may be used, although the enzyme is less optimized for error rate and speed. Alternatively, Epoxy dATP can be use to inactivate the enzyme.

In some embodiments, discrete features may contain oligonucleotides that are substantially complementary (e.g. 50%, 60%, 70%, 80%, 90%, 95%, 98%, 99% or 100%). With reference to FIG. 9, template oligonucleotides 801, 802, 803, 804 can have inherent errors as they are generally chemically synthesized (e.g., deletions at a rate of 1 in 100 bases and mismatches and insertions at about 1 in 400 bases). Assuming an average error rate of 1 in 300 bases and an average template oligonucleotide size of 70 bases, every 1 in 4 template oligonucleotides will contain an error compared to a reference sequence (e.g., the wide-type sequence of a gene of interest). For example, referring to FIG. 9, template oligonucleotide 803 contains an error 805 which can be a mismatch, deletion, or insertion. During PCR synthesis, the error 805 is retained in the synthesized oligonucleotide 803' as error 805'. Additional errors (not shown) can be introduced during PCR. Methods for error correction are needed for high-fidelity gene synthesis/assembly.

In one embodiment, error-containing oligonucleotides are removed by a method illustrated in FIG. 9. PCR products comprising oligonucleotides duplexes (e.g. duplexes 801-801', 802-802', 803-803', 804-804') are denatured by melting the duplexes (e.g., at elevated temperature, using a helicase, etc.), forming free oligonucleotides 801', 802', 803', 804'. In some embodiments, using a helicase to melt duplexes can provide for isothermal denaturing without elevating the temperature. The term "duplex" refers to a nucleic acid molecule that is at least partially double-stranded. A "stable duplex" refers to a duplex that is relatively more likely to remain hybridized to a complementary sequence under a given set of hybridization conditions. In an exemplary embodiment, a stable duplex refers to a duplex that does not contain a basepair mismatch, insertion, or deletion. An "unstable duplex" refers to a duplex that is relatively less likely to remain hybridized to a complementary sequence under a given set of hybridization conditions such as stringent melt. In an exemplary embodiment, an unstable duplex refers to a duplex that contains at least one base-pair mismatch, insertion, or deletion.

Next, under annealing conditions (e.g., lower temperature), oligonucleotides 801', 802', 803', 804' will randomly anneal to template oligonucleotides 801, 802, 803, 804. By way of example, new duplexes 801-803', 802-801', 803-804' and 804-802' can be formed. 802-801' and 804-802' are error-free duplexes, or stable duplexes whereas 801-803' and 803-804' each contain a mismatch between the two complementary strands (unstable duplexes). All duplexes within a feature are then subject to a stringent melting step to denature 801-803' and 803-804', leaving 802-801' and 804-802' intact. Oligonucleotides 803' (containing error 805') and 804' can then be removed or washed away. Error-free oligonucleotides 801' and 802' can be melted and recovered in a droplet for subsequent amplification, ligation, and/or chain extension. These steps can be repeated multiple times to enrich for error-free oligonucleotides, as support 800 can be washed and reused at least several times. Repeating the steps of denaturing and annealing allows the error-containing oligonucleotides to partner with different complementary oligonucleotides within the droplet, producing different mismatch duplexes. These can also be detected and removed as above, allowing for further enrichment for the error-free duplexes. Multiple cycles of this process can in principle reduce errors to undetectable levels. Local removal of error-containing oligonucleotides can be repeated at different features in a sequential fashion by drying the support between each different stringent melt conditions.

The conditions for stringent melt (e.g., a precise melting temperature) can be determined by observing a real-time melt curve. In an exemplary melt curve analysis, PCR products are slowly heated in the presence of double-stranded DNA (dsDNA) specific fluorescent dyes (e.g., SYBR Green, LCGreen, SYTO9 or EvaGreen). With increasing temperature the dsDNA denatures (melts), releasing the fluorescent dye with a resultant decrease in the fluorescent signal. The temperature at which dsDNA melts is determined by factors such as nucleotide sequence, DNA length and GC/AT ratio. Typically, G-C base pairs in a duplex are estimated to contribute about 3° C. to the Tm, while A-T base pairs are estimated to contribute about 2° C., up to a theoretical maximum of about 80-100° C. However, more sophisticated models of Tm are available and may be in which G-C stacking interactions, solvent effects, the desired assay temperature and the like are taken into account. Melt curve analysis can detect a single base difference. Various methods for accurate temperature control at individual features can be used as disclosed above.

In some embodiments, the entire support or array containing the discrete features is heated to a denaturing temperature. Preferably, denaturation of double stranded nucleic acid is performed in solution (e.g. within the droplet). During the heat denaturation step, the temperature of the support is raised to a stringent melt temperature or to a denaturing temperature (95° C. to 100° C.). Elevating the temperature of the support to a denaturing or stringent melt temperature allows the homoduplexes to dissociate into single strands before complete evaporation of the droplet volume. Heating the substrate results in the denaturation and evaporation of the solution, resulting in dried single-stranded oligonucleotides onto the discrete features. At this point, the entire support may be cooled down to a predefined hybridization or annealing temperature. A set of selected features or the totality of the features may be re-hydrated by addition of the appropriate annealing buffer (at the appropriate annealing temperature) at the selected features or on the entire support. Single stranded oligonucleotides may then be resuspended and allowed to diffuse and to hybridize or anneal to form the double-stranded oligonucleotides (homoduplexes or heteroduplexes).

Figure 10:
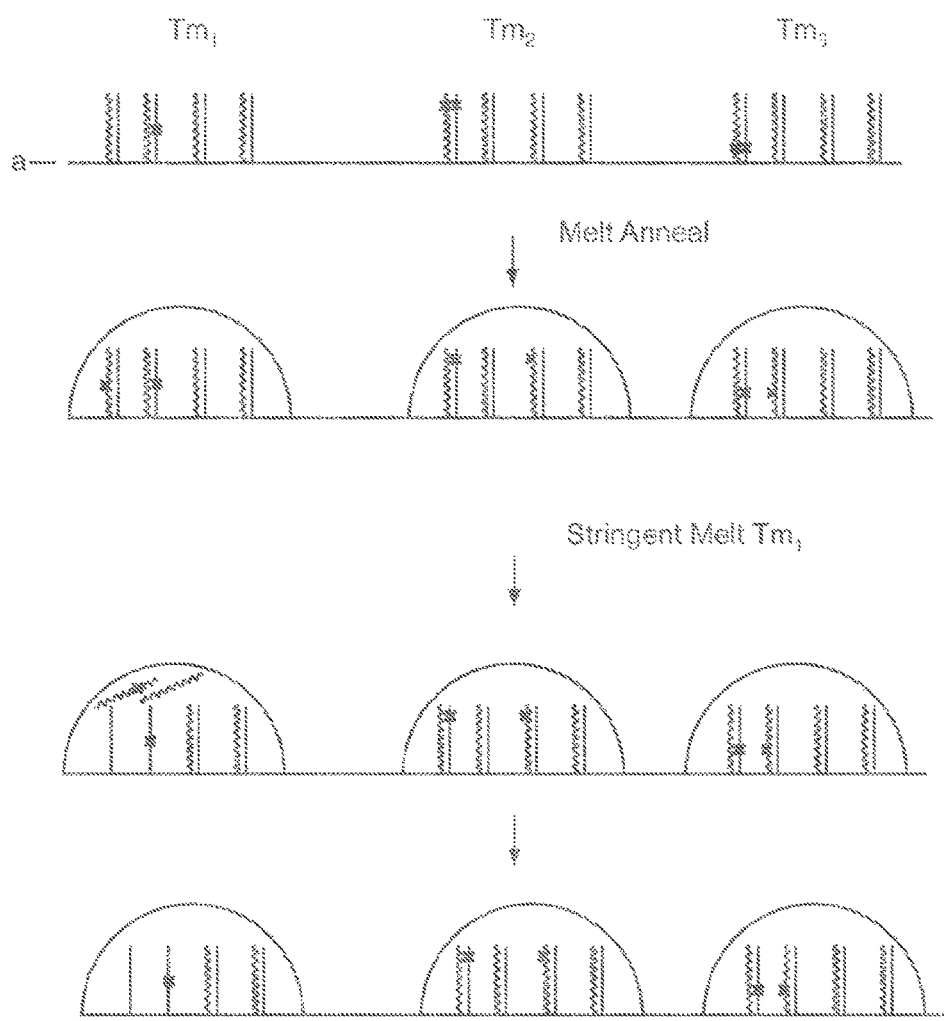
FIG. 10 illustrates a non-limiting example of selective error-removal of error-containing oligonucleotides.
Figure 10:
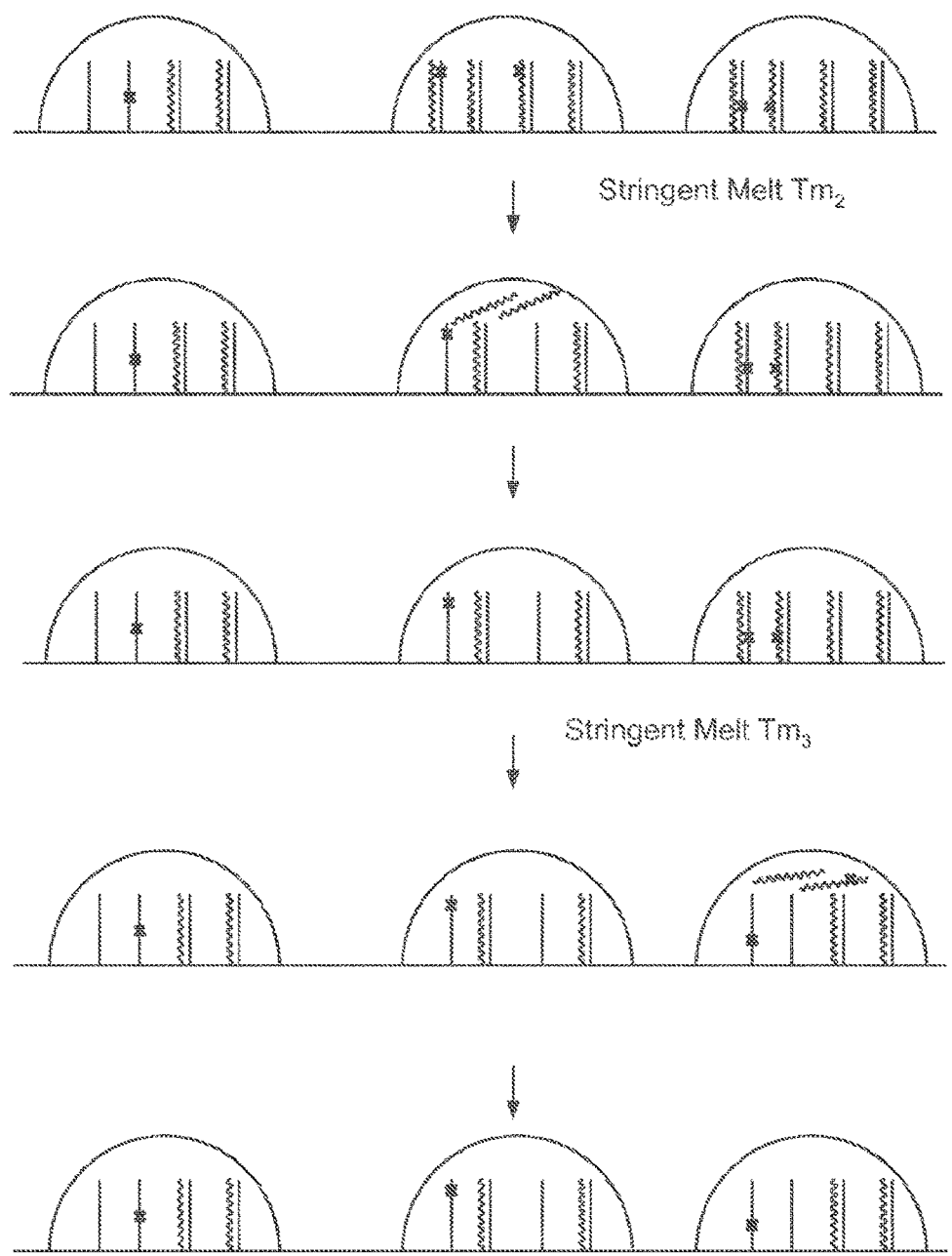

Accordingly, some aspects of the invention relate to the recognition and local removal of double-stranded oligonucleotides containing sequence mismatch errors at specific features. In one preferred embodiment of the invention, mismatch recognition can be used to control the errors generated during oligonucleotide synthesis, gene assembly, and the construction of longer polynucleotides. After amplification, the totality of the features or a set of the features comprising oligonucleotide duplexes are first subjected to round(s) of melting and annealing as described above (FIG. 10). Subsequently, a first set of discrete features comprising oligonucleotides having same theoretical Tm are hydrated and oligonucleotides are allowed to anneal under annealing conditions. Hydrated features are then subjected to a first stringent melt condition (condition 1). It would be appreciate that for sequential local error removal, it is preferable to first start with the stringent melt conditions corresponding to the lowest Tm (Tm(1)) and conclude with stringent melt conditions corresponding to the higher Tm (Tm(n)). In other embodiments, the totality of the features of the support may be hydrated and subjected to the lowest Tm temperature. Under the first specific stringent melt conditions Tm(1), only the oligonucleotides that are hybridized in an unstable duplex will de-hybridize (see FIG. 10A). De-hybridized oligonucleotides may be removed for example, using a vacuum or may be washed away. In a subsequent step, the support may be dried out and a second discrete features comprising oligonucleotides having a Tm higher than Tm(1) (for example (Tm(2)) are selectively rehydrated and allowed to anneal under annealing conditions. In other embodiments, the totality of the features of the support may be re-hydrated and subjected to the second Tm temperature Tm(2) wherein Tm(2) is higher than Tm(1) (FIG. 10B). These steps of selective hydration, annealing, stringent melt and removal of error-containing oligonucleotides can be repeated multiple times until all discrete features have been subjected to the appropriate stringent melt condition (theoretically 80-100° C.). Alternatively, a mismatch detecting endonuclease may be added to the droplet solution. In an exemplary embodiment, a Surveyor™ Nuclease (Transgenomic Inc.) may be added to the hydrated feature containing the oligonucleotide duplexes. Surveyor™ Nuclease is a mismatch specific endonuclease that cleaves all types of mismatches such as single nucleotide polymorphisms, small insertions or deletions. Addition of the endonuclease results in the cleavage of the double-stranded oligonucleotides at the site of the mismatch. The remaining portion of the oligonucleotide duplexes can then be melted at a lower and less stringent temperature (e.g. stringent melt) needed to distinguish a single base mismatch. One would appreciate that the error removal steps as well as the amplification steps may be repeated in a sequential fashion or in a highly parallel fashion by controlling the temperature of the entire support or of the independent features as described above.

Figure 11A:
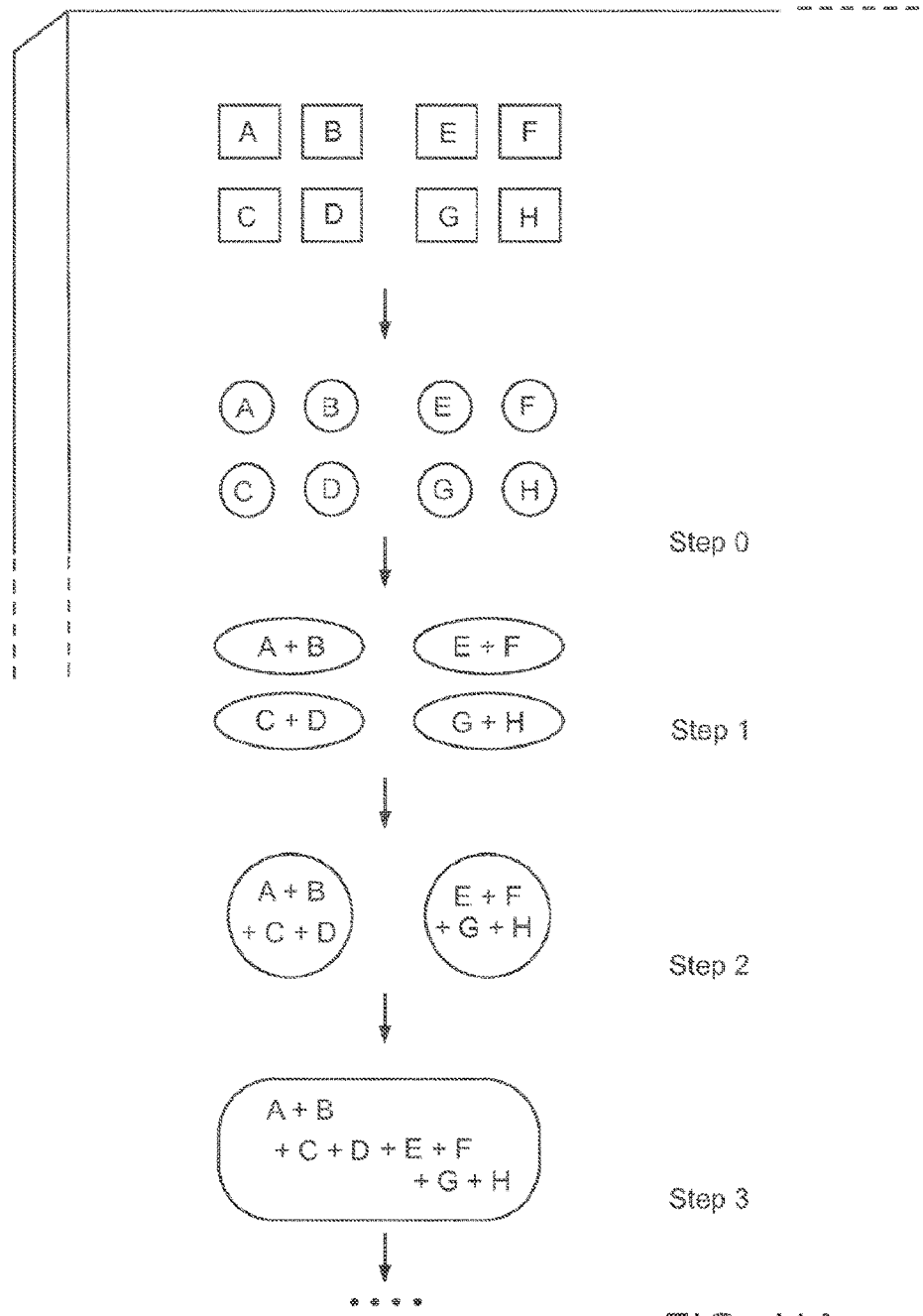
FIG. 11A illustrates an embodiment of a solid support comprising different molecules (A, B, C, etc.) and a non-limiting example of an assembly strategy.
Figure 12:
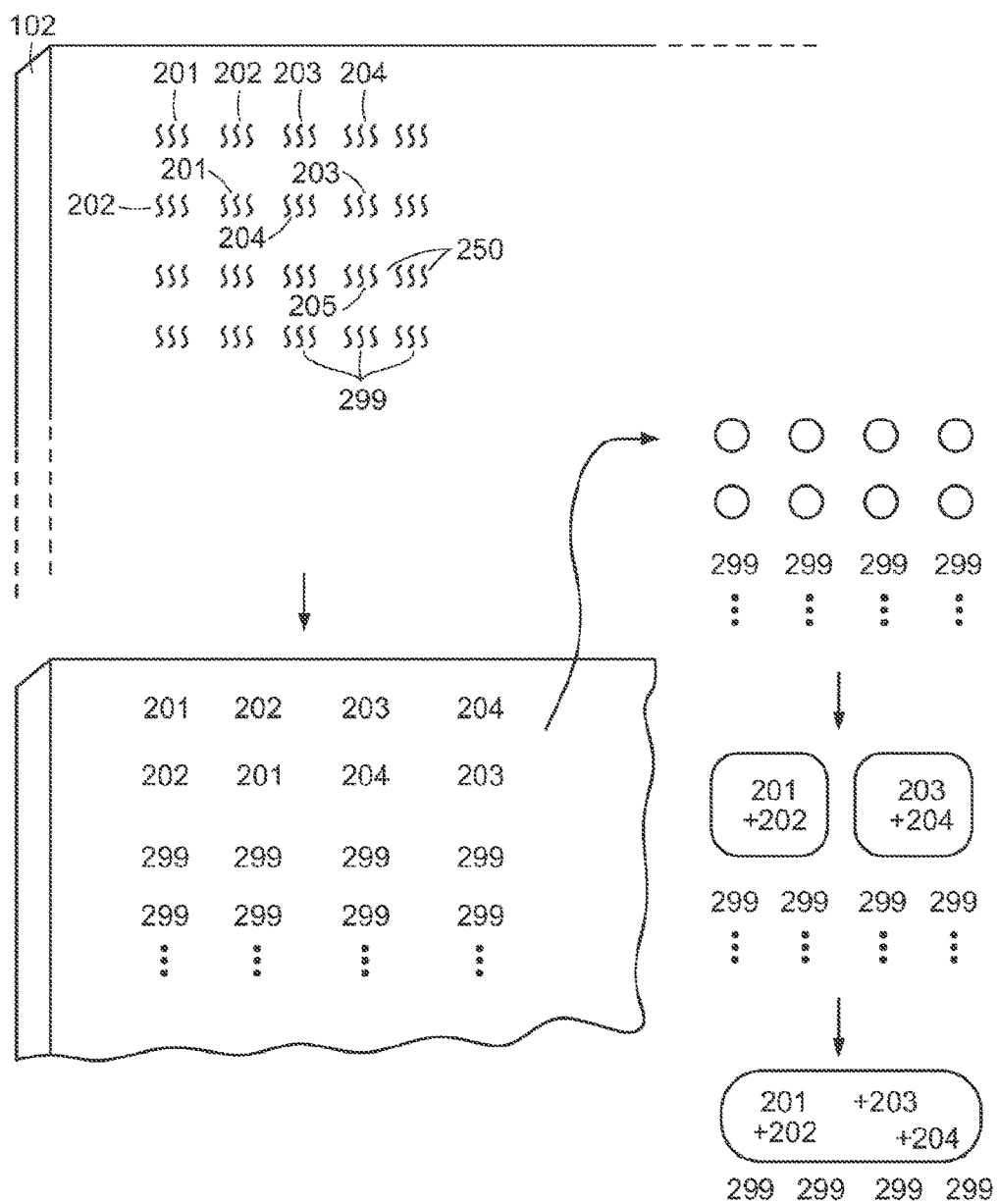
FIG. 12 illustrates an embodiment of a solid support comprising different and unique molecules (201, 202, 203, 204) supported or attached to the surface of 102, a unique molecule (250) supported or attached to the surface of 102 at multiple positions and other unique molecules (299) supported or attached to the surface of 102.

In a preferred aspect of the invention, oligonucleotides having predefined sequences are assembled after being amplified and error-filtered. In some embodiments, two adjacent droplets containing two multiple copies of different oligonucleotides or polynucleotides in solution are combined by merging the appropriate droplets on the solid support as illustrated in FIG. 11 and FIG. 12. In FIG. 12, the solid support comprises different and unique molecules (201, 202, 203, 204) supported or attached to the surface of 102, a unique molecule (250) supported or attached to the surface of 102 at multiple positions and other unique molecules (299) supported or attached to the surface of 102. On the solid support surface (102) an existing pattern of molecules can be found. For example, as illustrated in FIG. 12, different molecules or oligonucleotides can exist at different positions, as shown by the placement of 201, 202, 203, 204, 250, and 299. One should appreciate that the arrangement of these unique molecules (201, 202, 203, 204) can be designed to strategically allow the subsequent combining of the contents of these sites. For example, these unique molecules can be arranged in a checker board pattern. The first checker board pattern contains 201 and 202. After individual reactions within the microvolume of 201 and 202 are complete, the user can choose to combine the content of 201 and 202 by forming a droplet that encompasses both 201 and 202 sites. In another subsequent step, the content of 201+202 can be combined with the content of 203+204, to form a reaction that contains all four reaction products of the unique molecules (201, 202, 203, 204). FIG. 11A illustrates the same general concept with A, B, C, D. In step 0, all the unique molecules are reacted in separate volumes. In Step 1, the adjacent sites are combined, to give A+B, and C+D, etc. In Step 2, A+B can be combined with C+D, and etc. In Step 3, another level of aggregation is added. One should appreciate that there is no limit to the number of steps that can be implemented. In FIG. 11B, two possible arrangement strategies are outlined. In the first strategy, some adjacent sites comprise the same molecules or oligonucleotides (e.g. A and B) and the four sites may be combined to generate a circular droplet. In the second strategy, each site comprises a unique and different molecule or oligonucleotide and each site can be combined to an adjacent site.

For example, with reference to FIG. 12, solid supported oligonucleotide 201 and oligonucleotides 202 may be amplified in first stage droplet 1 and first stage droplet 2. After amplification, each first stage droplet contains one amplified double-stranded oligonucleotide sequence. In embodiments, multiple copies of oligonucleotides 201 and multiple copies of oligonucleotide 202 are eluted within the first stage droplet 1 and the first stage droplet 2, respectively. The two first stage droplets being in close proximity to each other are combined to form a second stage droplet. In some embodiments, two different or more oligonucleotides or polynucleotides may be immobilized or synthesized at the same location (or feature) on the solid support thereby facilitating their interaction after amplification within the same droplet. See e.g. US 2004/0101894. In some embodiments, droplets are merged to form bigger droplets by adding, or spotting additional "merger" droplets or volumes in between or around the appropriate original droplets. Two droplets, or isolated volumes can therefore merge if a "merger" droplet or volume is created and expanded until the merge takes place. The resultant merged volume will encompass the first stage droplets or first isolated volumes. The volume and location of the resulting merged volume can vary. The merged volumes (e.g. second stage droplet) can occupy a footprint that is the combination of all volumes (e.g. first stage droplets and merger droplet). Alternatively, the merged volumes can occupy at least part of the footprint of one of the isolated volume (e.g. first or second isolated volume).

Some aspects of the invention, relate to the destination selection and routing of the isolated volumes and therefore to the control of the location or footprint of merged volumes. One would appreciate that as individual regions of the support are addressable, individual isolated volumes such as droplets may be controlled individually. In some embodiments, it is preferable to place isolated volumes onto adjacent regions or features to allow merging of the volumes. Yet, in other embodiments, isolated volumes are directed or routed to a pre-selected destination.). In some case, the merged volumes occupy the footprint of one of the isolated volume and extend to one or more smaller contact angle regions (SCA). In some embodiments, the substrate of the support is substantially planar and droplets are routed using a two-dimensional path (e.g. x,y axis). Droplets may be moved to bring them to selected locations for further processing, to be merged with a second isolated volume into a second stage droplet at preselected locations and/or during the transport, to remove some reactants from the droplet (referred herein "wash-in-transport" process).

Figure 13A:
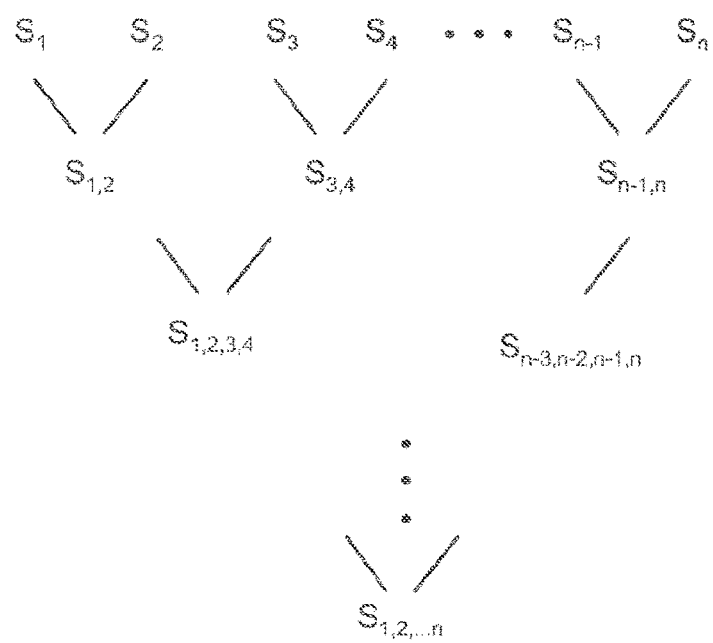
FIG. 13A illustrates a non limiting embodiment of hierarchical assembly of S1, S2, . . . Sn group members to form S1-n.
Figure 13B:
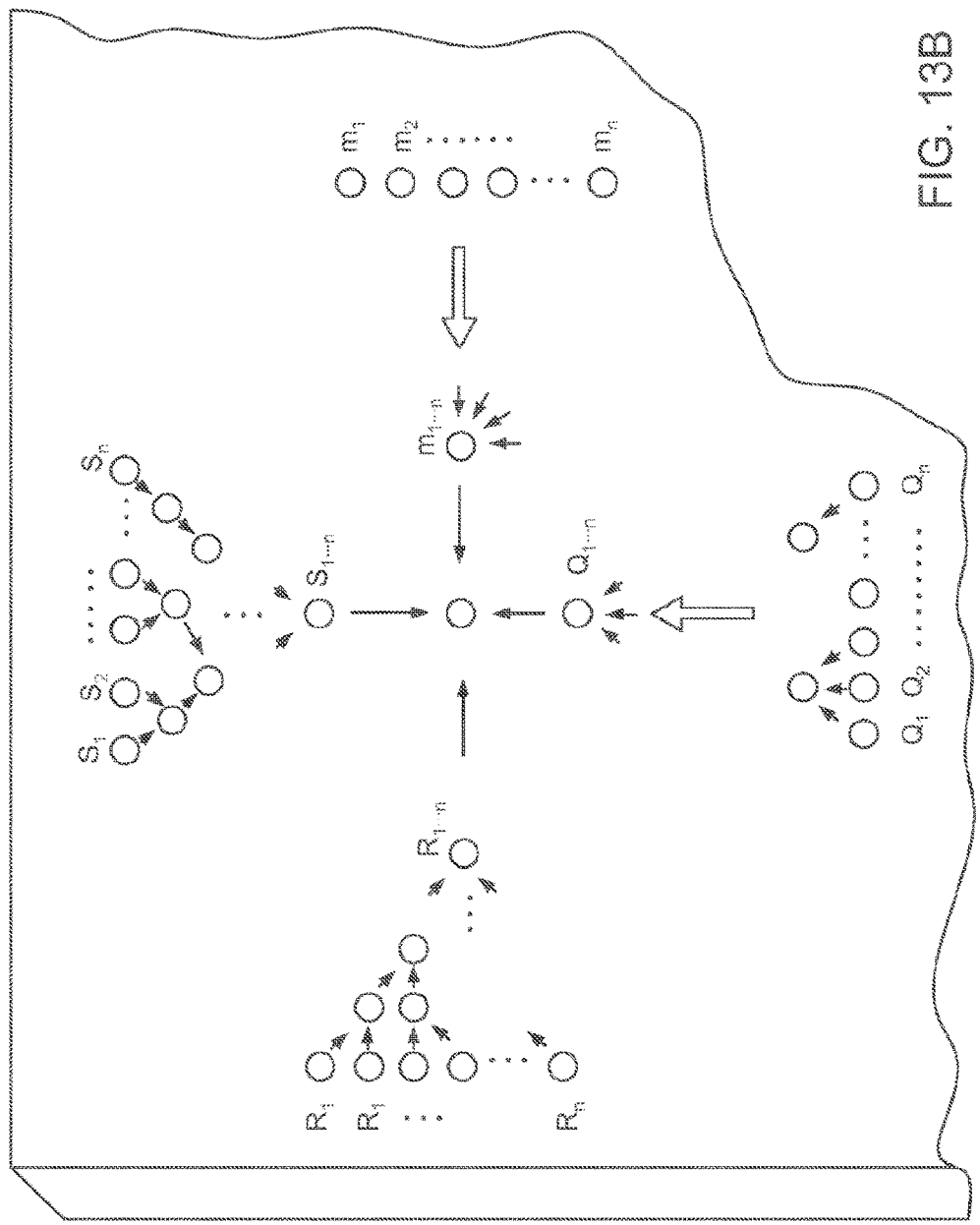
FIG. 13B illustrates a non-limiting embodiment of hierarchical assembly of four assembly sub-groups members M, Q, R, S.

In some embodiments, step-wise hierarchical and/or sequential assembly can be used to assemble oligonucleotides and longer polynucleotides. In a preferred embodiment, the methods use hierarchical assembly of two or more oligonucleotides or two or more nucleic acids subassemblies at a time. Neighboring droplets can be manipulated (move and/or merged, as described above) to merge following a hierarchical strategy thereby improving assembly efficiency. In some embodiments, each droplet contains oligonucleotides with predefined and different nucleic acid sequences. In some embodiments, two droplets are moved following a predefined path to an oligonucleotide-free position. In a preferred embodiment, the assembly molecules (e.g. oligonucleotides) are pre-arranged on the support surface at pre-determined discrete features. For example, with reference to FIG. 13A, the support comprises different unique molecules (e.g. oligonucleotides S1 to Sn). The arrangement of the molecules is designed to strategically allow the hierarchical assembly of S1 with S2, S2 with S4 etc. . . . by manipulating neighboring droplets S1 and S2, S3 and S4, and merge the droplets to form the S1-2, S3-4, S(n−1)-(n) first stage droplets. In some embodiments, 2, 3, 4, 5, 6, 7, 8, 9, 10 or more droplets may be combined at each step. In a preferred embodiment, droplets (S1, S2, . . . ) are moved and combined in an oligonucleotide-free position or feature to form first stage droplets (S1,-2, S3,-4, S(n−1),). In a second step, another level of aggregation is added. For example, referring to FIG. 13A, first stage droplet S1,2 can be combined to first stage droplet S3,4 to form a merged second stage droplet S1,2,3,4. The hierarchical assembly terminal merging step results in droplet S1,2,3, . . . , n containing the content of droplet S1+S2+ . . . Sn. Furthermore, different terminal merging location (two or more assembly groups) can be strategically positioned next to each other to allow for the combination of different assembly droplets and thereby for the assembly of a predetermined sequence (FIG. 13B). In some embodiments, 2, 3, 4, 5, 6, 7, 8, 9, or more assembly groups can be arranged to minimize droplet travel distance to form the predetermined sequence. In some embodiments, the assembly members within each group are arranged on the support surface in a pattern minimizing the droplet travel distance required for the formation of the M1,2,3 . . . n, Q1,2,3 . . . n, R1,2,3 . . . n, S1,2,3 . . . n products. In a further embodiments, the position of the M1,2,3 . . . n, Q1,2,3 . . . n, R1,2,3 . . . n, S1,2,3 . . . n are arranged on the support surface in a pattern minimizing the droplet travel distance required for the formation MQRS(1,2,3 . . . n).

One should appreciate that isolated volumes may be routed independently in a sequential or highly parallel fashion. Droplets may be routed using electrowetting-based techniques (see for example, U.S. Pat. No. 6,911,132 and U.S. Patent Application 2006/0054503). Electrowetting principle is based on manipulating droplets on a surface comprising an array of electrodes and using voltage to change the interfacial tension. By applying an electric field (e.g. alternating or direct), the contact angle between the fluid and surfaces can be modified. For example, by applying a voltage, the wetting properties of a hydrophobic surface can become increasingly hydrophilic and therefore wettable. In some embodiments, the array of electrode is not in direct contact with the fluid. In some embodiments, droplets are moved using a wettability gradient. It has been shown that droplets placed on wettability gradient surfaces typically move in the direction of increasing wettability (see Zielke and Szymczyk, Eur. Phys. J. Special Topics, 166, 155-158 (2009)). In other embodiments, droplets may be moved using a thermal gradient. When placed on a thermal gradient, droplets move from higher temperature locations towards lower temperature locations. Moving droplets using electrowetting, temperature gradients and wettability gradients depend on the liquid (e.g. aqueous, non-aqueous, solute concentration), the size of the droplets and/or the steepness of the gradient.

Figure 3:
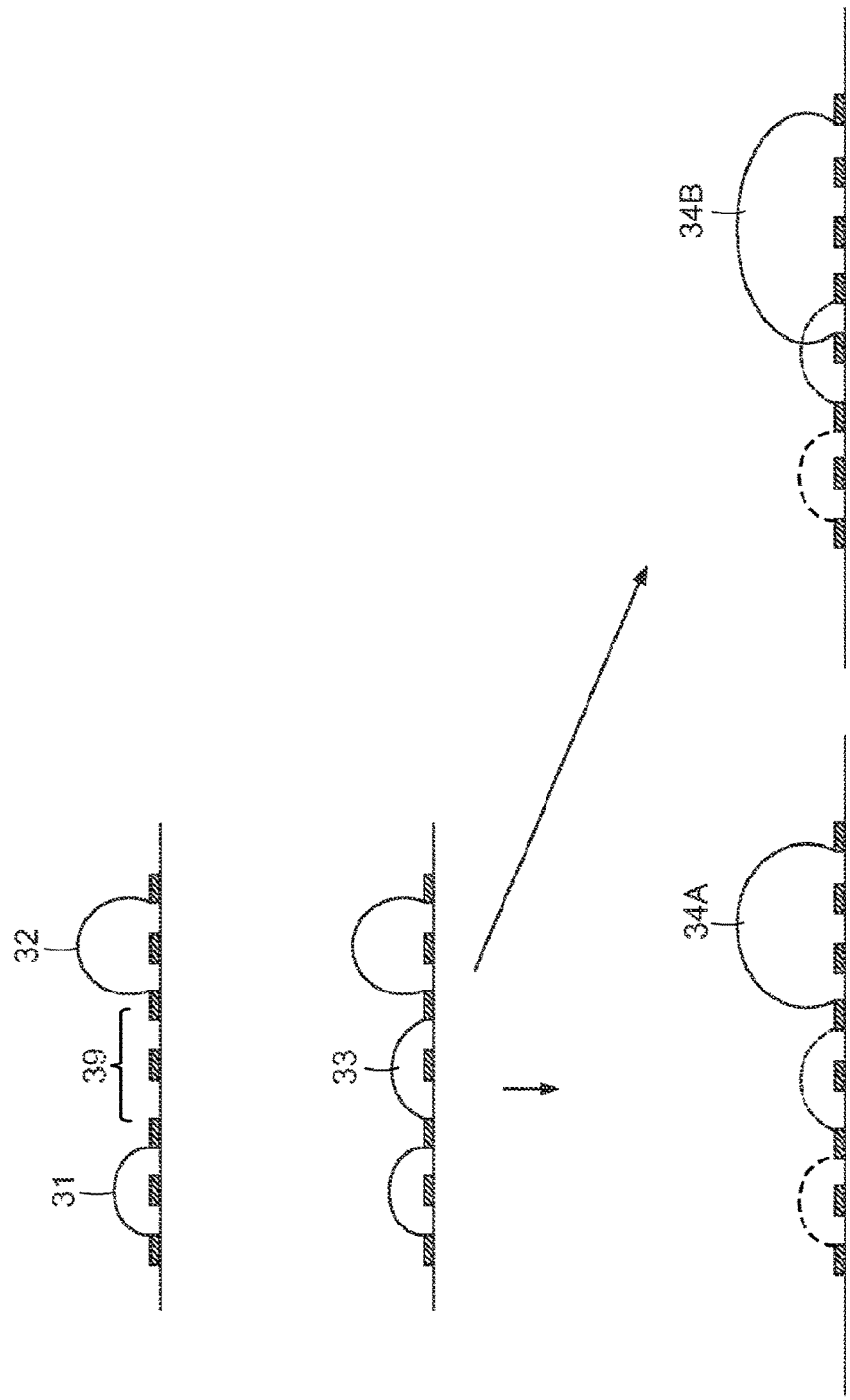
FIG. 3 illustrates a non-limiting embodiment of the merging and the move of droplet 31 with droplet 32 using a merger droplet 33 and the resultant merger droplet footprint 34A and 34B.

One skilled in the art will appreciate that most of the electrowetting merging and mixing strategies rely on the fact that droplets have identical volumes before merging. In some aspects of the invention, routing of the droplet and merging is controlled by the using different size droplets. In a preferred embodiment, the footprint of the merged volume is controlled by the size of the droplets before merging. In some embodiments, the method comprises moving the content of smaller volume droplets to the position of arger volume droplets. Referring to FIG. 3, two isolated volumes or droplets (31, 32) are created, the volume of droplet 31 being smaller than the volume of droplet 32. The droplets are separated from each other by a region 39. Region 39 may comprise at least one SCA, at least one HCA, or any combination of SCA and HCA. After a merger droplet 33 is created, it may contact droplet 31 or droplet 32 or both droplet 31 and droplet 32. The resultant volume occupies the footprint or a substantial part of the footprint of the larger of the two original isolated liquid volumes. For example, as illustrated in FIG. 3, the merged volume 34A can occupy the footprint of the larger droplet 32 or the merged volume 34B can occupy a substantial part of the footprint of the larger droplet.

Figure 5A:
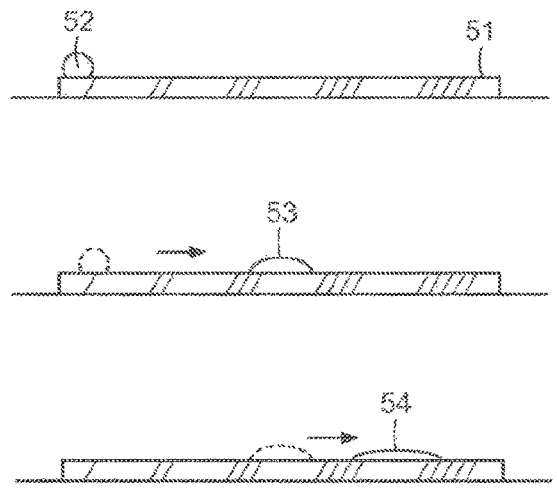
FIG. 5A illustrates a non-limiting embodiment of a droplet movement along a hydrophilic substrate 51 from a more hydrophobic location 52 to a more hydrophilic location 53 and then 54.
Figure 5B:
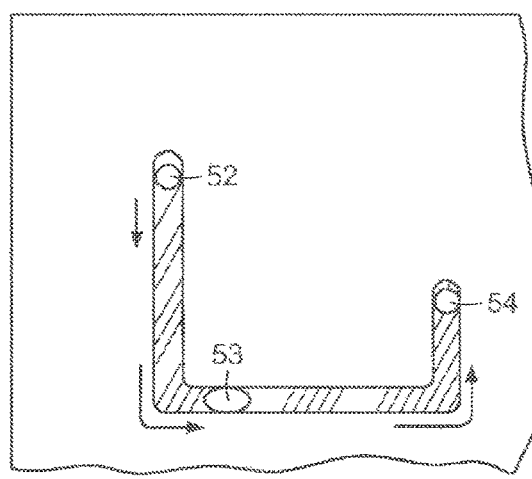
FIG. 5B illustrates a non-limiting embodiment of a droplet movement along a hydrophilic substrate 51 from a more hydrophobic location 52 to a more hydrophilic location 53 and then 54 on a support comprising bends.
Figure 5C:
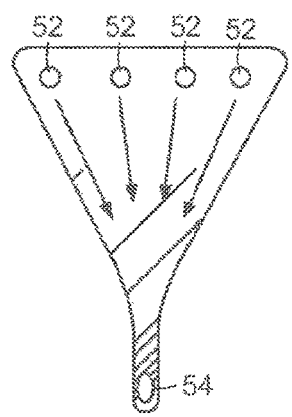
FIG. 5C illustrates a non-limiting embodiment of a droplet movement along a hydrophilic substrate 51 from a more hydrophobic location 52 to a more hydrophilic location 53 and then 54 on a support comprising varying widths.
Figure 6:
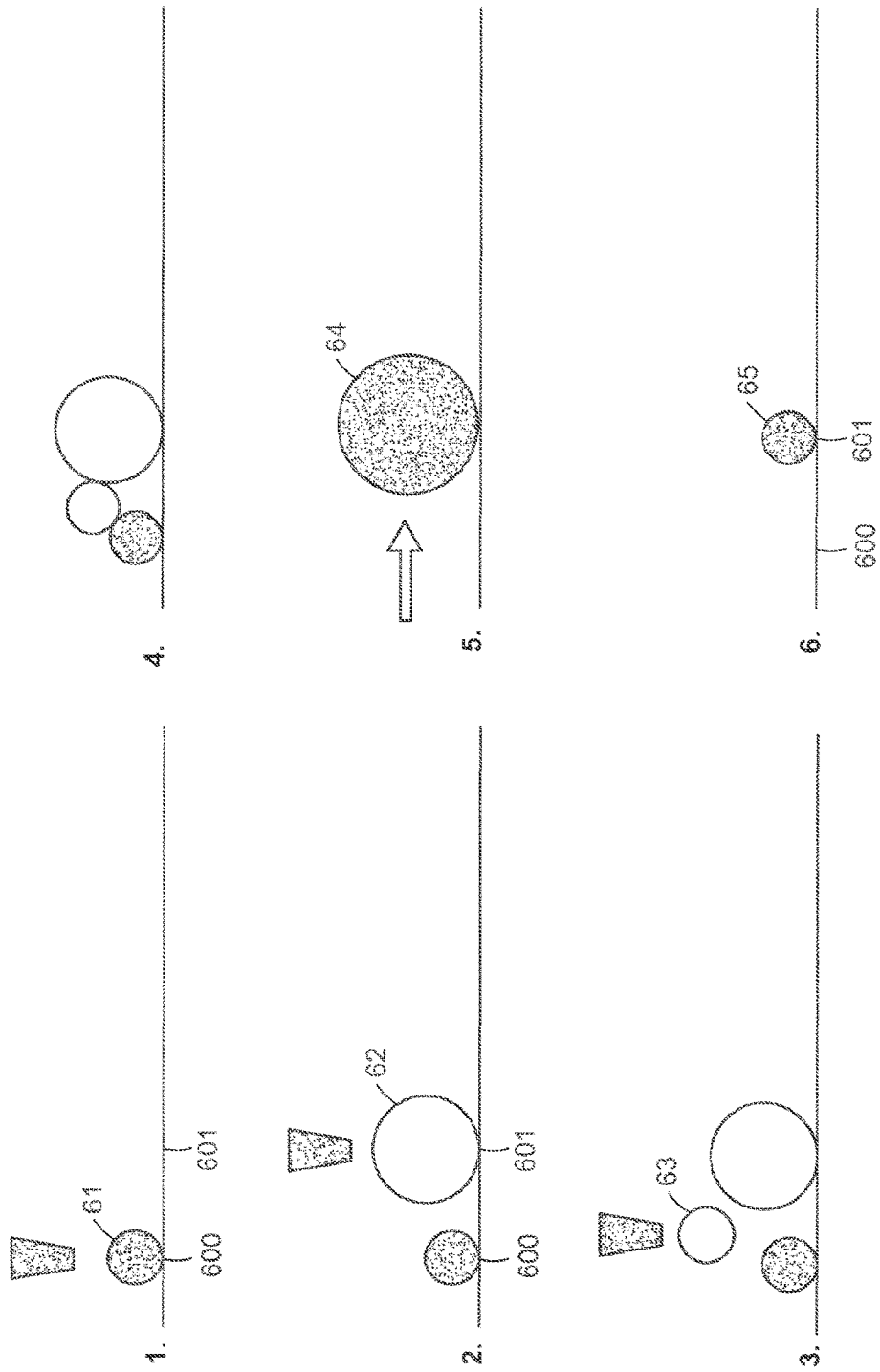
FIG. 6 illustrates a non-limiting example showing graphically with varying gray scale how the "solution" droplet is diluted by the "merge" droplet and the "anchor" droplet and is then re-concentrated by evaporation.

One skilled in the art will appreciate that the principle described herein can be applied to move liquid volumes such as droplets on the support along a predetermined path and to determine the exact location of the merged volume. In some embodiments, the content of the smaller volumes may repeatedly be moved to the position of larger volumes in order to move liquid volumes over a distance that is larger than a merger region. The principle is illustrated in FIG. 4 and FIG. 5. In an exemplary embodiment, a first isolated volume referred as "solution droplet" is created (e.g solution droplet 41, FIG. 4A; solution droplet 410, FIG. 4B, solution droplet 51, FIG. 5). The solution typically contains molecules of interest (e.g. oligonucleotides) or solute of interest. In some embodiments, a group of droplets (411, FIG. 4B) is added to a position close to the leading edge of the solution droplet in the direction of the intended droplet displacement or path. The wetting of the leading edge of the solution droplet 410, together with the dynamic forces caused by the deposition of the group of droplets 411 causes the solution droplet to move in the direction of the leading edge, thereby resulting in the displacement of the solution droplet 410 to form droplet 412 at a new position on the support. This process can be repeated to allow the displacement of the solution droplet to the desired location on the support. In some embodiments, the volume of the droplet 412 may be adjusted by evaporation, thereby allowing the droplet to return to its original volume (410), before repeating the procedure. In other embodiments, a solution droplet is created (41, FIG. 4A, 51, FIG. 5). Simultaneously or subsequently, a second isolated volume referred as an "anchor droplet" is created in the direction of the intended "solution droplet" path or route. A third volume referred as "merger droplet" (43, FIG. 4) is created between the first and second isolated volumes. Once merged, the resultant volume (44, FIG. 4) occupies the location of the anchor droplet (42, FIG. 4). In some embodiments, the solution droplet and the anchor droplets contain the solutes and/or molecules of interest. Yet in other embodiment, the solution droplet contains the solute and/or the molecules of interest. In some embodiments, the merger droplet contains water. Yet in other embodiments, the merger droplet contains solute and/or molecules of interest. Referring to FIG. 6, a solution droplet 61 containing the solute of interest is inkjetted on to the substrate at position or feature 600 (FIG. 6, step 1). Subsequently, an anchor droplet, for example water or buffer, is inkjetted onto the substrate at position or feature 601, wherein feature 601 is in the direction of the droplet path (FIG. 6, step 2). A merger droplet 63 is then injected between the solution and the anchor droplet (FIG. 6, step 3). The solution droplet, merger droplet and anchor droplet are merged and solutes are mixed by either passive diffusion or active mixing. The resultant volume 64, referred as the "merged droplet", occupies the footprint of the larger anchor droplet (FIG. 6, step 5). After evaporation, the merged droplet returns to the original size of the original solution droplet (FIG. 6, step 6). In some embodiments, the resultant volumes (merged droplets) are adjusted by allowing evaporation (to reduce its size) or by adding fluid (to increase its size) and can be moved by repeating steps 1 through 6. As illustrated in FIG. 4, after adjustment of the size of the merged droplet (44 to 44A), another isolated volume (45) is placed adjacent to (44) in the direction of the intended droplet move. Using the same merging process described above, a merger droplet 46 is added resulting a merged volume 47. These steps can be repeated until the payload solute originally in droplet 41 is moved to a desirable or pre-selected location. One or more of theses newly merged droplets may be manipulated according the same protocol which includes deposition of an anchor droplet, deposition of a merger droplet, merging and mixing, and evaporation. In some embodiments, as illustrated in FIG. 6, the "solution" droplet 61 is diluted by the "merge" droplet 63 and the "anchor" droplet 62 and is then re-concentrated by evaporation of the droplet 65. Merged droplets and reaction features act as virtual wells or chambers in which the reactions take place. Reactions, include, but are not limited to incubation, enzymatic reactions, dilution, mixing, error reduction and/or assembly. Although the figures show a linear, one dimensional, path, it should be appreciated that the droplet can be moved anywhere on the support surface. In some embodiments, the droplets are moved in a two dimensional direction. Any other operations derived form this protocol can be envisioned. For example, droplets can be deposited sequentially, simultaneously, or in a parallel fashion. Droplets may contain only water and may be used as dilution droplets. Other droplets may contain a solute. Droplet content may be mixed by passive diffusion or active mixing. In some embodiments, at least two droplets are moved independently following a similar path and are then moved towards a feature that is referred as a reaction feature wherein the droplets are merged. The first and second droplet paths across the substrate may follow the same direction or may follow opposite directions. For example, a first droplet may be moved toward a stationary second droplet or the first and the second droplet may be moved toward each others. Moreover, if two droplets have the same size, reduction of the size of one droplet will enable it to move in the direction and to the location of the larger volume. Reduction of the size of the droplet can be achieved by evaporation. Evaporation of liquid may be achieved using any technique known in the art. For example, the isolated liquid volume to be decreased may be heated to induce or accelerate evaporation. Alternatively, to merge a first droplet at the location of a second droplet, liquid may be added to the second droplet to increase its size comparatively to the first droplet.

Figure 14:
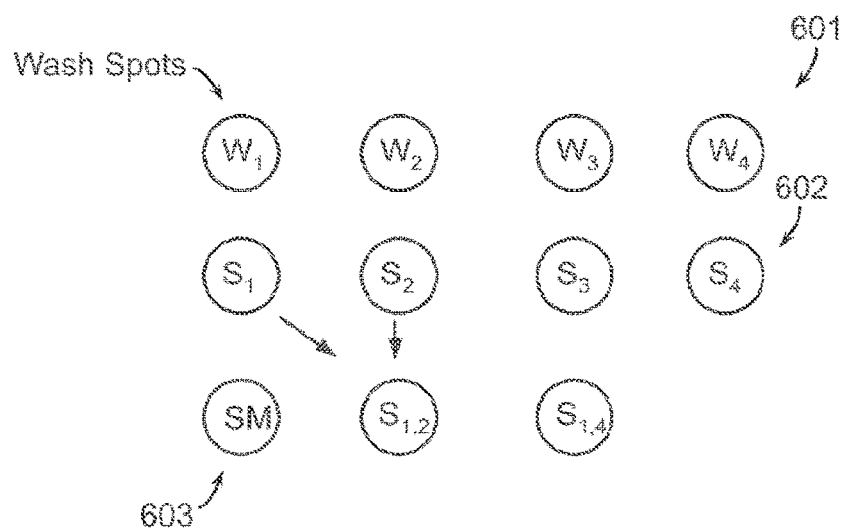
FIG. 14 illustrates a non-limiting embodiment of the wash in transportation process.

Another benefit of the droplet movement process described herein is the implementation of a "wash" operation (referred herein as wash-in-transportation). The movement of the liquid away from a surface feature allows the separation of the surface-bound molecules (e.g. oligonucleotides) from the molecules in solution. Hence, a wash operation is therefore implemented. For example, wash-in-transportation can be used to remove the template oligonucleotides form the complementary oligonucleotides after amplification. In some embodiments, "wash-in transportation" features or wash spots may be placed adjacent to features where oligonucleotide processing takes place. Referring to FIG. 14, S1, S2, S3, and S4 (602) represent features carrying oligonucleotides or nucleic acid assembly components. Wash spots W1, W2, W3, and W4 (601) are placed adjacent to the S1, S2, S3, and S4 features. Undesirable products released in the droplet solution on features S1, S2, S3, and/or S4 can be moved to the wash spots features W1, W2, W3, and W4, respectively. In some embodiments, the support provides one wash spot W for each assembly feature S or a common wash spot for two or more assembly features. Wash-in-transportation process can also be used to remove unwanted error-containing oligonucleotides from stable duplexes after annealing and stringent melt. For example, referring to FIG. 14, "stringent melt" features SM (603) can be placed along the path of nucleic acid assembly progression, allowing for stringent melt error correction as described above. Similarly, the support may comprise one SM spot for each assembly step or a common SM spot for two or more assembly features.

In some embodiments, the "merger" droplets or the "anchor" droplet may contain or not contain enzyme (e.g. polymerase, ligase, etc.), additional oligonucleotides and all reagents to allow assembly by PCR or by ligation (enzymatic or chemical) or by any combination of enzymatic reaction. For example, oligonucleotides in a given droplet may hybridize to each other and may assemble by PCR or ligation. The bigger droplets or second stage droplets contain polynucleotides subassemblies and can be subsequently merged to form larger droplets or third stage droplet containing larger fragments. As used herein the term subassembly refers to a nucleic acid molecule that has been assembled from a set of oligonucleotides. Preferably, a subassembly is at least 2-fold or more long than the oligonucleotides. For example, a subassembly may be about 100, 200, 300, 400, 500, 600, or ore bases long. One should appreciate that the use of droplets as isolated reaction volumes enables a highly parallel system. In some embodiments, at least 100, at least 1,000 reactions can take place in parallel. In some embodiments, the primers are immobilized on the support in close proximity to the spots containing the oligonucleotides to be assembled. In some embodiments, the primers are cleaved in situ. In some embodiments, the primers are supported on the solid support. The primers may then be cleaved in situ and eluted within a droplet that will subsequently merged with a droplet containing solid supported or eluted oligonucleotides.

Figure 15A:
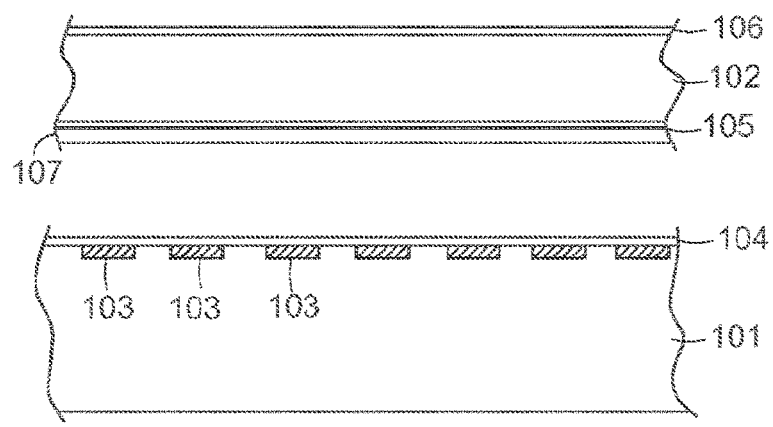
FIG. 15A illustrates a cross section of the electrowetting device with a top and a bottom side electrode.
Figure 15B:
FIG. 15 B illustrates a configuration of an electrowetting device with only a top side electrode.
FIG. 15C illustrates a configuration of the device with only a bottom side electrode
Figure 15C:
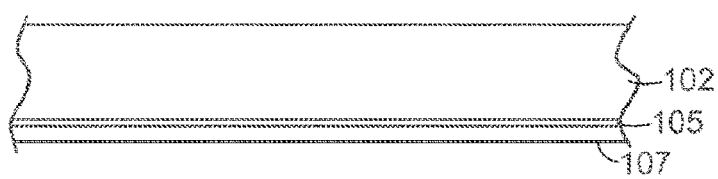

Some aspects of the invention relate to the droplet-based liquid handling and manipulation methods by implementing electrowetting-based techniques. In some embodiments, the microfluidics device comprises two primary supports or substrates (FIG. 15, elements (101) and (102)). Each substrate has features on one or both sides to implement the necessary electrodes (FIG. 15: 103: control electrodes, 105: bottom side electrode, 106: top side electrode) as well as insulation and surface modifications (FIG. 15: 104, 107). In an exemplary embodiment, the insulation and/or surface modification layer is a dielectric and has controlled surface quality such that it is hydrophobic or hydrophilic. In some embodiments, the substrate (102) has the top side electrode (106) and/or the bottom side electrode (105). In the case of a substrate having only the top side electrode, the substrate (102) is configured as shown in FIG. 15 B. In the case of a substrate having only a bottom electrode, the substrate (102) is configured as shown in FIG. 15C.

Figure 16:
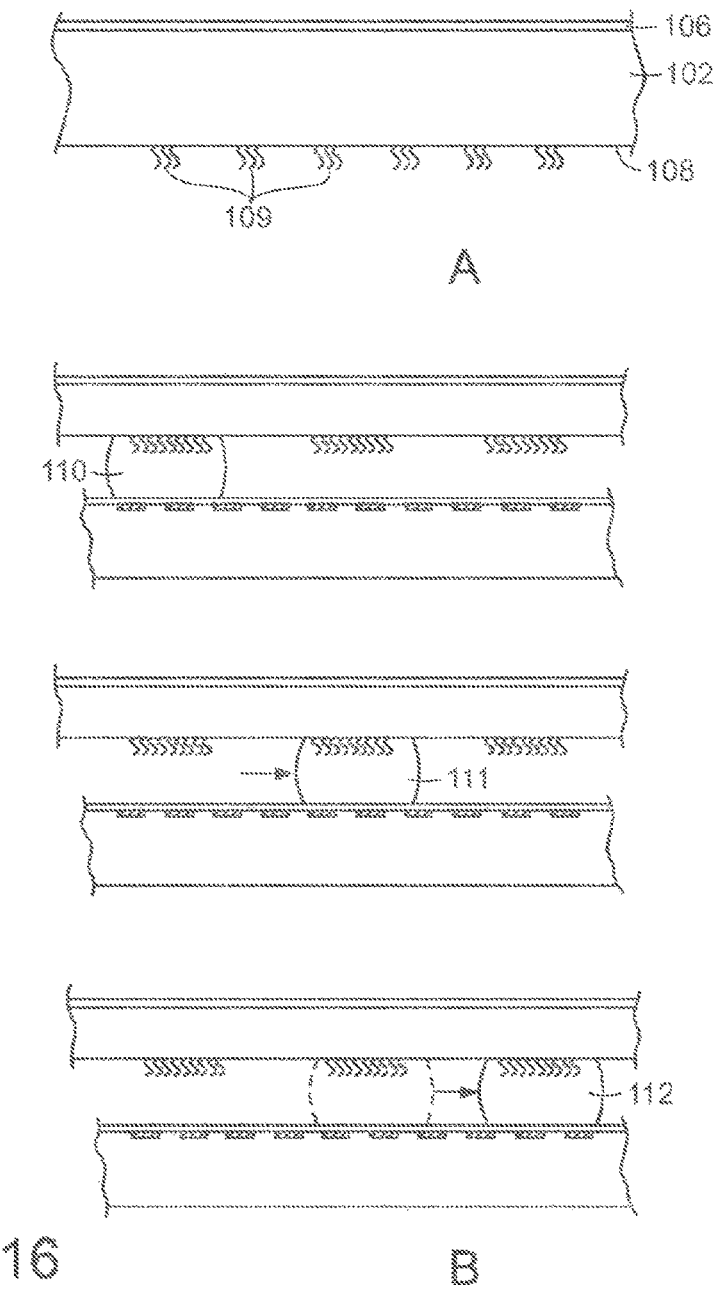
FIG. 16 illustrates a non limiting embodiment of the electrowetting device with a top side electrode.
Figure 21:
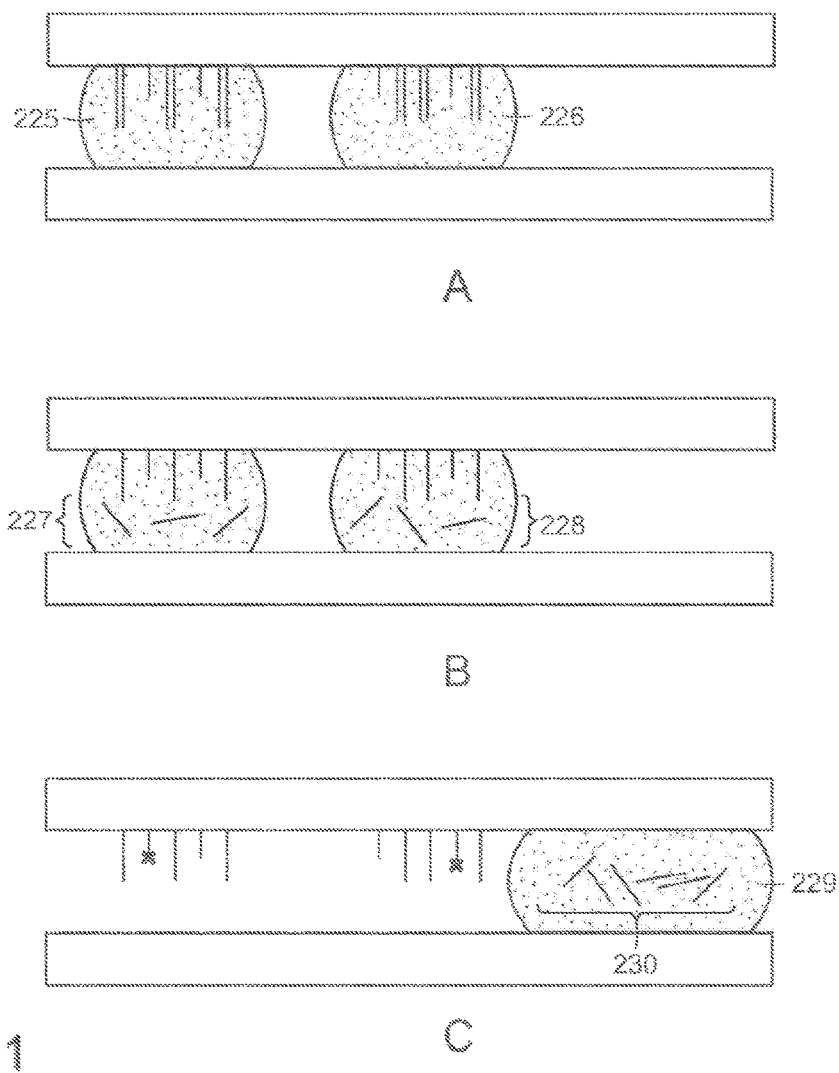
FIG. 21 illustrates a non limiting embodiment of polynucleotide assembly using an electrowetting device.

In a preferred embodiment, the substrate (102) is a solid support or surface (108). One should appreciate that a variety of molecules such as oligonucleotides, nucleic acids, peptides, proteins (e.g. antibodies), polysaccharides, etc. . . . may be attached to the support as disclosed herein (see FIG. 16A) Preferably, a library of molecules are attached a different location of the support. For example, members of this library (109) may be attached to the substrate via covalent bonding, Van der Waals forces, or any other attachment mechanisms. One should appreciate that it is possible to manipulate a droplet (110) from one position to another position (111) to another position (112) without limitation in direction (in both x and y direction, defining a plane) as shown in FIG. 16B. While FIG. 16 shows a substrate (102) with top side electrode, FIG. 17 shows a substrate (102) with bottom electrodes. In preferred embodiment, methods are provided for the assembly of a polymer such a s polynucleotides from shorter oligonucleotides molecules (see FIG. 18). In some embodiment, the nucleic acid molecule may be assembled and the assembly process may include one or more step describe herein. In an exemplary embodiment, the assembly steps include an extension step (FIG. 18 A-C), a shuffling (FIG. 18 D,E), a washing step (FIG. 19 A,B), an error Correction (FIG. 19 C-E), a length-dependent melt and wash step (FIG. 20), and a merging and assembly step(FIG. 21) or any combination thereof.

Figure 18:
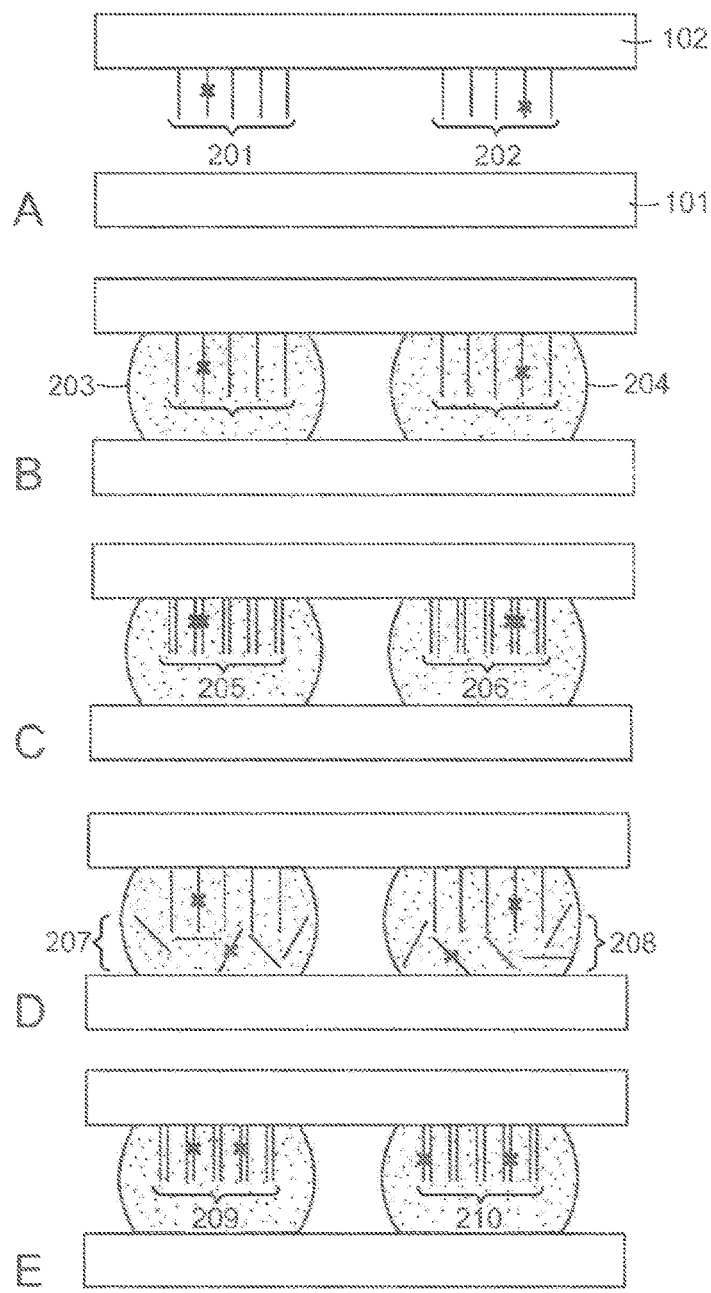
FIG. 18 illustrates a non limiting embodiment of polymer assembly.
Figure 19:
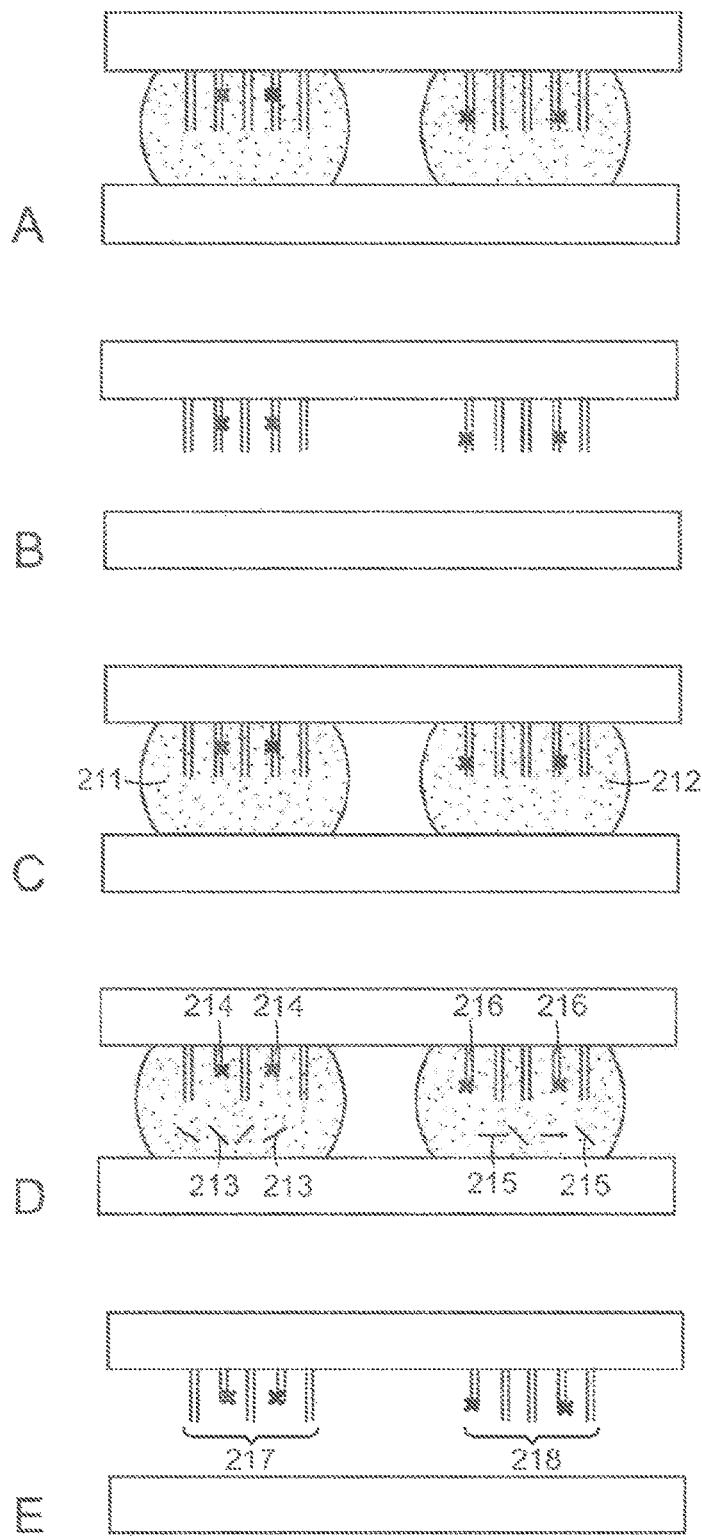
FIG. 19 illustrates a non limiting embodiment of selective error-removal of error-containing oligonucleotides.

As shown in FIG. 18, individual spots (201, 202) comprise members of a high density high diversity library. Individual droplets (203, 204) can be formed and placed at the locations corresponding to the individual spots (201, 202) via standard electrowetting techniques. As described above, the droplet solution may comprise specific enzymes catalyzing biochemical reactions such as nucleic acid (or polymer) extension resulting in the extended nucleic acid molecule or polymer (205, 206). In an exemplary embodiment, the members of the library are template oligonucleotides and the extended products (207, 208) are copies of the oligonucleotides, thereby forming double stranded oligonucleotides strands or duplexes. Oligonucleotide strands can dissociate from their template via thermal or chemical treatments. Oligonucleotides can also be detached from the substrate via thermal or chemical treatments. For example, nucleic acid copies can be melted off the template by increasing the temperature of the droplets to above the melting temperature of the duplex, as shown in FIG. 18D. Once the droplets are allowed to cool, the copies will re-anneal back to the surface-attached templates. However, since the re-annealing process is random, a natural shuffling takes place. As shown in FIG. 18C, the duplexes (205) has one template containing an error. The copy from the error containing template, after re-annealing, has a very high probability to hybridize with a template strand that is not the exact strand where the copy is made. This shuffling process creates hetero-duplexes (209, 210) that are not perfectly matching each other, allowing for subsequent recognition of mismatches in these hetero-duplexes (see copending U.S. Provisional application 61/264,643, filed on Nov. 25, 2009, which is incorporated by reference herein in its entirety). Prior to mismatch recognition, the hetero-duplexes can be washed to remove the previously active extension enzymes, or to simple change the buffer condition. In this operation, the droplets are forced out via a flow of fluid, either liquid or gas, to purge the contents between substrate (101) and (102), as shown in FIG. 19B. Subsequent to the wash step, a second buffer and enzyme system or enzymes mixture can be introduced in the same way as before (203, 204), for example via standard electrowetting techniques, resulting in droplets (211, 212). In an exemplary embodiment, the second buffer may comprise an endonuclease that recognizes mismatch or an endonuclease and a DNA ligase. For example, the endonuclease is the CEL1 enzyme which cleaves heteroduplex DNA at single base-pair mismatch (Surveyor™ Nuclease, Transgenomic Inc.). In some embodiments, DNA ligase can be added to heal non-specific cleavage by the endonucleases (e.g. CEL1). The enzyme (or enzyme mixture), cleaves at the mismatch sites created by the shuffling step described above, resulting in truncated template-copy stubs (214, 216) and cleaved products (213, 215). The cleaved products can be removed with a second wash step, as shown in FIG. 19E. An additional truncation removal step can be performed after the mismatch cleave. A third buffer is introduced and forms droplets (219, 220). Temperature of the droplets is increased to cause the shorter truncated products (221, 222) to melt, while keeping the long full-length duplexes attached to the surface. The temperature can be carefully selected to give very precise discrimination for length and even sequences. A wash step can be carried out to remove the truncated products (221, 222). After wash, the population of polymer still attached to the surface has enhanced purity and reduced error density (FIG. 20C). In a preferred embodiment, the purified and error-corrected oligonucleotides (or short polymers) are utilized in an assembly reaction to create longer polynucleotides (or longer polymers). For example, as shown in FIG. 20, droplets containing enzymes and suitable buffer can be formed as described before. The droplets (225, 226) each covers a spot that contain one or more members of the high density high diversity library. By raising the temperature of the droplets, copies can be release into the liquid phase or droplet (227, 228). Individual members of the library (or groups of the library) can be combined in a precise and controlled manner to create a reaction volume where desirable populations (230) of assembly polymers is gathered (229). In a preferred embodiment, the droplet comprises enzymes, such as ligase or polymerase, and the longer polynucleotide may be assembled by polymerase or ligase mediated assembly reaction. The enzyme(s) in the fluid can assemble the said population into a desirable longer chain polymer. The assembly steps described above can be repeated to create increasingly longer polymer chain or polynucleotide until the desirable product is reached. In some embodiments, droplets are covered with an immiscible solution (e.g. oil) forming a layer over the droplets to limit evaporation that may occur during the melt/anneal steps. Droplets may be manipulated using a standard electrowetting process such as digital microfluidics (Fair, Microfluid Nanofluid (2007) 3: 245-281), or a light-induced optoelectrowetting (Chiou et al. Sensors and Actuators, A104 (2003) 222-228). It should be appreciated that the electrowetting (or optoelectrowetting) substrate (101) can be used as a general fluidics manipulator that couples to many different library substrates (102). For example, an instrument with one substrate (101) can be used to process multiple DNA microarrays (102) in the same manner.

Some aspects of the invention relate to the transport of charged molecules such as nucleic acid (e.g. oligonucleotides or polynucleotides) to a selected destination or selected feature on a support within a fluid medium using a planar two dimensional path (x, y axis). Preferably the molecules are electrophoretically transported by polarization of the molecules of interest on application of a voltage, the charged molecule moving towards an electrode (anode or cathode). In some embodiments, the array comprises one or more preferably, a plurality of electrophoretic planar microfluidic units, each microfluidic unit comprising two electrodes. The electrodes system comprises at least one cathode and one anode. In some configurations, the cathode and anode are shared by a plurality of microfluidic units. In other configuration, the cathodes and anode are for a single microfluidic unit. The microfluidic units enable the displacement of charged molecules of interest according to an electrophoretic path. In some embodiments, each microfluidic unit comprises at least on channel. Preferably, each microfluidic unit is fluidly connected. For example, each microfluidic unit may be connected to another microfluidic unit, by a channel. In preferred embodiments, an aqueous buffer is utilized as the fluid in the device. In some embodiments, each microfluidic unit may comprise a capture site. In some embodiment, the capture site corresponds to an array feature. Yet in other embodiment, the capture site corresponds to an array interfeature. In some embodiments, the capture site comprises a material that capture charged molecules. In nucleic acids, the phosphate ion carries a negative charge. Accordingly, preferably the capture site comprises a material that capture negatively charged molecules. In some instances, the capture material may capture the charged molecules of interest by chemically interaction through covalent bonding, hydrogen bonding, ionic bonding, Vander Waals interactions, or other molecular interactions. Alternatively, the capture material does not interact with the molecules of interest but retards the molecule's electrophoretic transport. In some embodiments, at least a first feature and a second feature of the arrays are in fluid communication and the charged oligonucleotide or polynucleotide is moved between the first feature and a second feature by applying a voltage between the first and the second feature.

Figure 26:
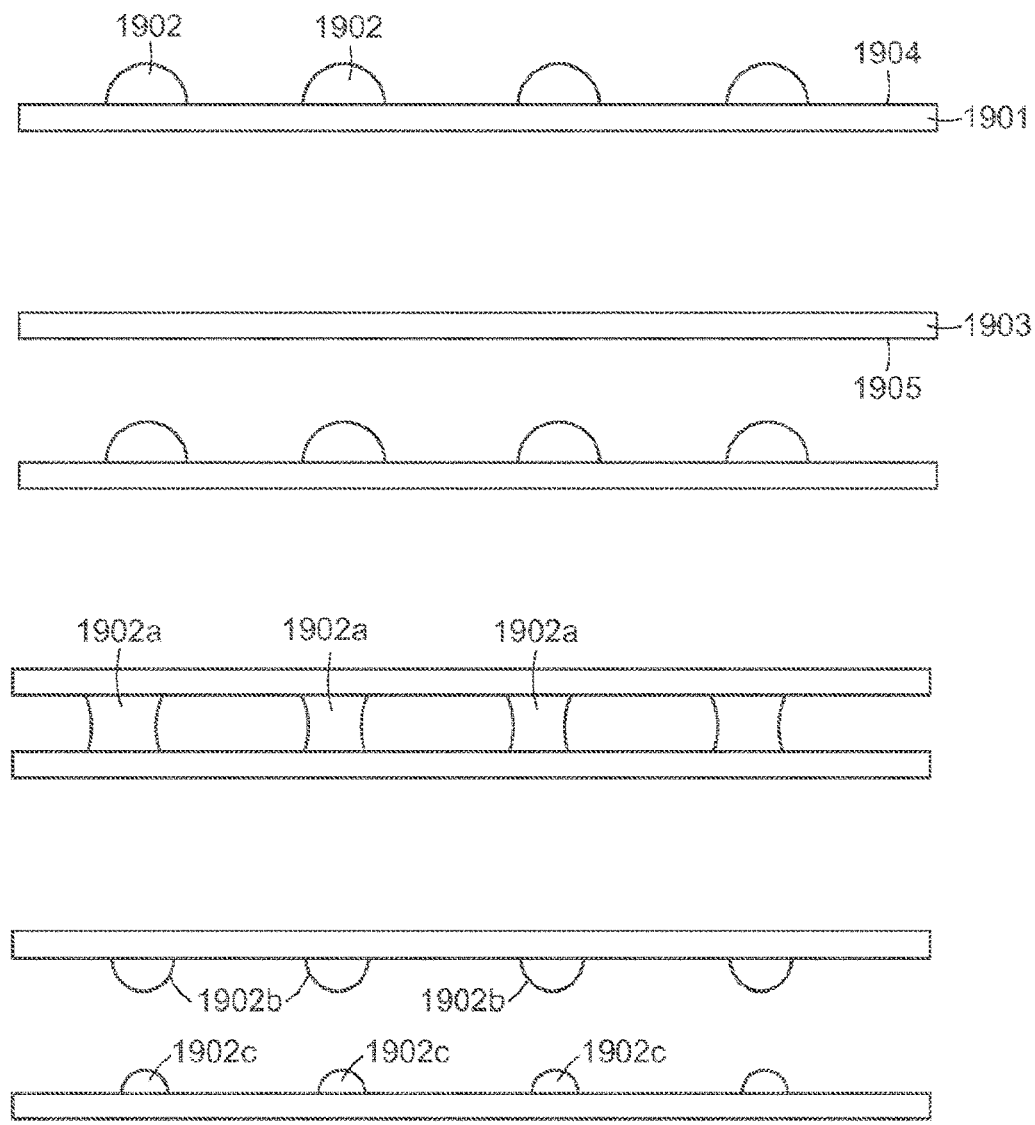
FIG. 26 illustrates a non-limiting embodiment of plate to plate transfers.
Figure 27:
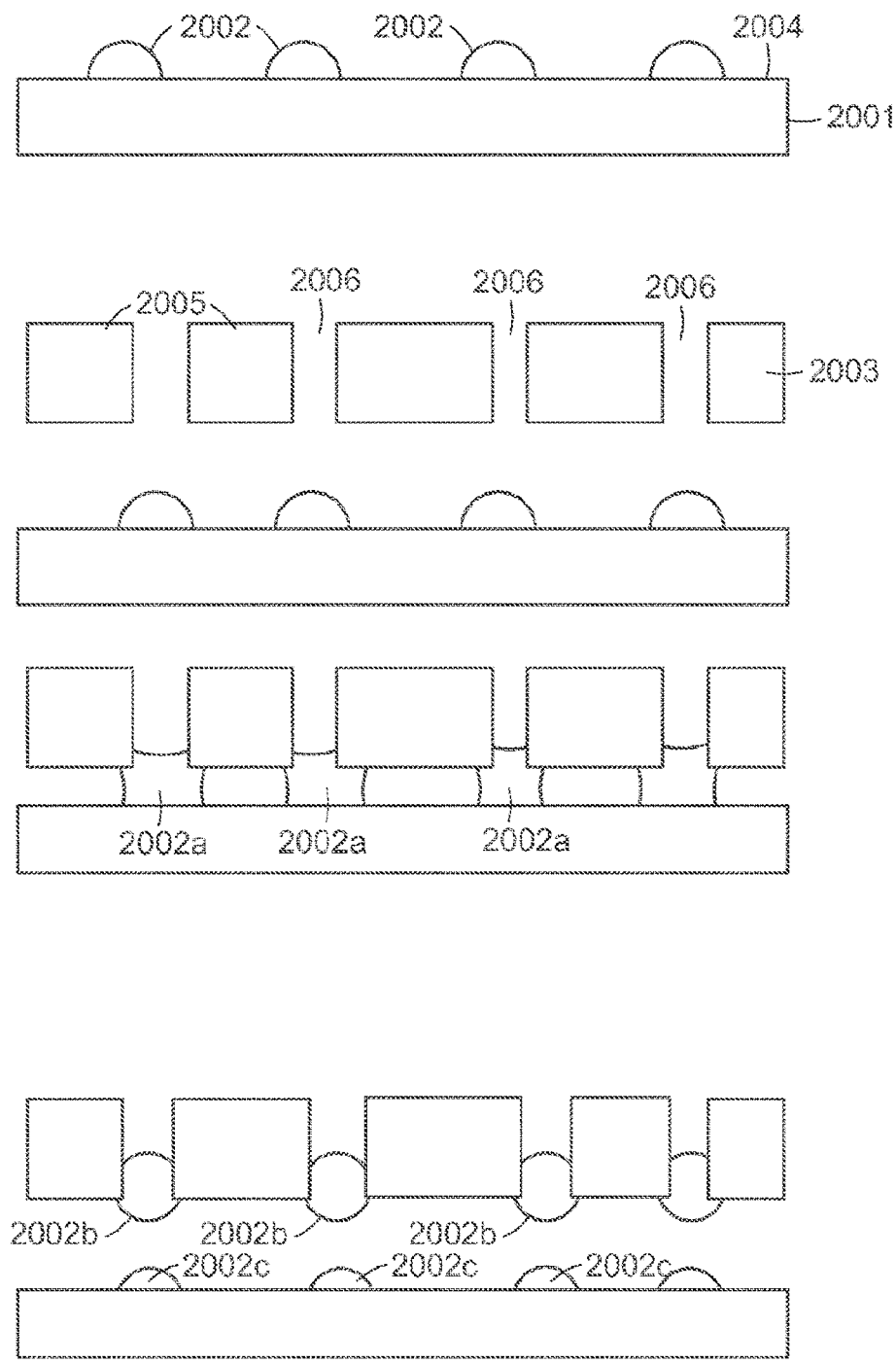
FIG. 27 illustrates a non-limiting embodiment of plate to plate transfers.

In some aspects of the invention, the reaction volumes or a portion of the reaction volumes may be routed from a first substrate to a second substrate, as illustrated in FIG. 26 and FIG. 27. In some embodiments, a substrate (1901) can support individualized reaction volumes (1902) on a surface (1904), which can have surface properties designed to achieve a particular contact angle between a reaction volume (1902) and the surface (1904) (see FIG. 26). A second substrate (1903) can have another surface (1905) with properties designed to achieve other contact angle(s). The two surfaces (1904 and 1905) can be brought into close proximity so that the reaction volume (1902*a*) bridges both surfaces. Furthermore, the two substrates can then be pulled apart, breaking such bridges (1902*a*), and form two sets of separate volumes, one set called source volumes (1902*c*) on the substrate surface (1904), and another set called destination volumes (1902*b*) on the transferred surface (1905). The ratio of the source volume to destination volume is controlled by the surface properties (e.g. contact angled) of the source surface (1904) and destination surface (1905). In another embodiment, the substrate (2001) can support individualized reaction volumes (2002), which can have surface properties designed to achieve a particular contact angle between a reaction volume (2002) and the surface (2004). A second substrate (2003), designed to have features manufactured into the substrate forming surfaces (2005) that defines channels (2006). The channel forming surfaces (2005) can be designed with properties to achieve another particular contact angle. The channels can be aligned to the reaction volumes (2002). The two substrates (2001 and 2003) can be brought into close proximity so that the reaction volume (2002*a*) bridges both substrates. The two substrates can then be pulled apart, breaking such bridges (2002*a*), and forming two sets of separate volumes, one set called source volumes (2002*c*) on the substrate surface (2004), and another set called destination volumes (2002*b*) on the transferred surface (2005). The ratio of the source volume to destination volume is controlled by the surface properties of the source surface (2004) and destination surface (2005).

In certain embodiments, the oligonucleotides are designed to provide the full sense (plus strand) and antisense (minus strand) strands of the polynucleotide construct. After hybridization of the plus and minus strand oligonucleotides, double-stranded oligonucleotides are subjected to ligation in order to form a first subassembly product. Subassembly products are then subjected to ligation to form a larger nucleic acid or the full nucleic acid sequence.

Ligase-based assembly techniques may involve one or more suitable ligase enzymes that can catalyze the covalent linking of adjacent 3' and 5' nucleic acid termini (e.g., a 5' phosphate and a 3' hydroxyl of nucleic acid(s) annealed on a complementary template nucleic acid such that the 3' terminus is immediately adjacent to the 5' terminus). Accordingly, a ligase may catalyze a ligation reaction between the 5' phosphate of a first nucleic acid to the 3' hydroxyl of a second nucleic acid if the first and second nucleic acids are annealed next to each other on a template nucleic acid). A ligase may be obtained from recombinant or natural sources. A ligase may be a heat-stable ligase. In some embodiments, a thermostable ligase from a thermophilic organism may be used. Examples of thermostable DNA ligases include, but are not limited to: Tth DNA ligase (from *Thermus thermophilus*, available from, for example, Eurogentec and GeneCraft); Pfu DNA ligase (a hyperthermophilic ligase from *Pyrococcus furiosus*); Taq ligase (from *Thermus aquaticus*), any other suitable heat-stable ligase, or any combination thereof. In some embodiments, one or more lower temperature ligases may be used (e.g., T4 DNA ligase). A lower temperature ligase may be useful for shorter overhangs (e.g., about 3, about 4, about 5, or about 6 base overhangs) that may not be stable at higher temperatures.

Non-enzymatic techniques can be used to ligate nucleic acids. For example, a 5'-end (e.g., the 5' phosphate group) and a 3'-end (e.g., the 3' hydroxyl) of one or more nucleic acids may be covalently linked together without using enzymes (e.g., without using a ligase). In some embodiments, non-enzymatic techniques may offer certain advantages over enzyme-based ligations. For example, non-enzymatic techniques may have a high tolerance of non-natural nucleotide analogues in nucleic acid substrates, may be used to ligate short nucleic acid substrates, may be used to ligate RNA substrates, and/or may be cheaper and/or more suited to certain automated (e.g., high throughput) applications.

Non-enzymatic ligation may involve a chemical ligation. In some embodiments, nucleic acid termini of two or more different nucleic acids may be chemically ligated. In some embodiments, nucleic acid termini of a single nucleic acid may be chemically ligated (e.g., to circularize the nucleic acid). It should be appreciated that both strands at a first double-stranded nucleic acid terminus may be chemically ligated to both strands at a second double-stranded nucleic acid terminus. However, in some embodiments only one strand of a first nucleic acid terminus may be chemically ligated to a single strand of a second nucleic acid terminus. For example, the 5' end of one strand of a first nucleic acid terminus may be ligated to the 3' end of one strand of a second nucleic acid terminus without the ends of the complementary strands being chemically ligated.

Accordingly, a chemical ligation may be used to form a covalent linkage between a 5' terminus of a first nucleic acid end and a 3' terminus of a second nucleic acid end, wherein the first and second nucleic acid ends may be ends of a single nucleic acid or ends of separate nucleic acids. In one aspect, chemical ligation may involve at least one nucleic acid substrate having a modified end (e.g., a modified 5' and/or 3' terminus) including one or more chemically reactive moieties that facilitate or promote linkage formation. In some embodiments, chemical ligation occurs when one or more nucleic acid termini are brought together in close proximity (e.g., when the termini are brought together due to annealing between complementary nucleic acid sequences). Accordingly, annealing between complementary 3' or 5' overhangs (e.g., overhangs generated by restriction enzyme cleavage of a double-stranded nucleic acid) or between any combination of complementary nucleic acids that results in a 3' terminus being brought into close proximity with a 5' terminus (e.g., the 3' and 5' termini are adjacent to each other when the nucleic acids are annealed to a complementary template nucleic acid) may promote a template-directed chemical ligation. Examples of chemical reactions may include, but are not limited to, condensation, reduction, and/or photochemical ligation reactions. It should be appreciated that in some embodiments chemical ligation can be used to produce naturally occurring phosphodiester internucleotide linkages, non-naturally-occurring phosphamide pyrophosphate internucleotide linkages, and/or other non-naturally-occurring internucleotide linkages.

In some embodiments, the process of chemical ligation may involve one or more coupling agents to catalyze the ligation reaction. A coupling agent may promote a ligation reaction between reactive groups in adjacent nucleic acids (e.g., between a 5'-reactive moiety and a 3'-reactive moiety at adjacent sites along a complementary template). In some embodiments, a coupling agent may be a reducing reagent (e.g., ferricyanide), a condensing reagent such (e.g., cyanoimidazole, cyanogen bromide, carbodiimide, etc.), or irradiation (e.g., UV irradiation for photo-ligation).

In some embodiments, a chemical ligation may be an autoligation reaction that does not involve a separate coupling agent. In autoligation, the presence of a reactive group on one or more nucleic acids may be sufficient to catalyze a chemical ligation between nucleic acid termini without the addition of a coupling agent (see, for example, Xu et al., (1997) Tetrahedron Lett. 38:5595-8). Non-limiting examples of these reagent-free ligation reactions may involve nucleophilic displacements of sulfur on bromoacetyl, tosyl, or iodo-nucleoside groups (see, for example, Xu et al., (2001) Nat. Biotech. 19:148-52). Nucleic acids containing reactive groups suitable for autoligation can be prepared directly on automated synthesizers (see, for example, Xu et al., (1999) Nuc. Acids Res. 27:875-81). In some embodiments, a phosphorothioate at a 3' terminus may react with a leaving group (such as tosylate or iodide) on a thymidine at an adjacent 5' terminus. In some embodiments, two nucleic acid strands bound at adjacent sites on a complementary target strand may undergo auto-ligation by displacement of a 5'-end iodide moiety (or tosylate) with a 3'-end sulfur moiety. Accordingly, in some embodiments the product of an autoligation may include a non-naturally-occurring internucleotide linkage (e.g., a single oxygen atom may be replaced with a sulfur atom in the ligated product).

In some embodiments, a synthetic nucleic acid duplex can be assembled via chemical ligation in a one step reaction involving simultaneous chemical ligation of nucleic acids on both strands of the duplex. For example, a mixture of 5'-phosphorylated oligonucleotides corresponding to both strands of a target nucleic acid may be chemically ligated by a) exposure to heat (e.g., to 97° C.) and slow cooling to form a complex of annealed oligonucleotides, and b) exposure to cyanogen bromide or any other suitable coupling agent under conditions sufficient to chemically ligate adjacent 3' and 5' ends in the nucleic acid complex.

In some embodiments, a synthetic nucleic acid duplex can be assembled via chemical ligation in a two step reaction involving separate chemical ligations for the complementary strands of the duplex. For example, each strand of a target nucleic acid may be ligated in a separate reaction containing phosphorylated oligonucleotides corresponding to the strand that is to be ligated and non-phosphorylated oligonucleotides corresponding to the complementary strand. The non-phosphorylated oligonucleotides may serve as a template for the phosphorylated oligonucleotides during a chemical ligation (e.g., using cyanogen bromide). The resulting single-stranded ligated nucleic acid may be purified and annealed to a complementary ligated single-stranded nucleic acid to form the target duplex nucleic acid (see, for example, Shabarova et al., (1991) Nucl. Acids Res. 19:4247-51).

In one aspect, a nucleic acid fragment may be assembled in a polymerase mediated assembly reaction from a plurality of oligonucleotides that are combined and extended in one or more rounds of polymerase-mediated extensions. In some embodiments, the oligonucleotides are overlapping oligonucleotides covering the full sequence but leaving single-stranded gaps that may be filed in by chain extension. The plurality of different oligonucleotides may provide either positive sequences (plus strand), negative sequences (minus strand), or a combination of both positive and negative sequences corresponding to the entire sequence of the nucleic acid fragment to be assembled. In some embodiments, one or more different oligonucleotides may have overlapping sequence regions (e.g., overlapping 5' regions or overlapping 3' regions). Overlapping sequence regions may be identical (i.e., corresponding to the same strand of the nucleic acid fragment) or complementary (i.e., corresponding to complementary strands of the nucleic acid fragment). The plurality of oligonucleotides may include one or more oligonucleotide pairs with overlapping identical sequence regions, one or more oligonucleotide pairs with overlapping complementary sequence regions, or a combination thereof. Overlapping sequences may be of any suitable length. For example, overlapping sequences may encompass the entire length of one or more nucleic acids used in an assembly reaction. Overlapping sequences may be between about 5 and about 500 oligonucleotides long (e.g., between about 10 and 100, between about 10 and 75, between about 10 and 50, about 20, about 25, about 30, about 35, about 45, about 50, etc.). However, shorter, longer, or intermediate overlapping lengths may be used. It should be appreciated that overlaps between different input nucleic acids used in an assembly reaction may have different lengths.

Polymerase-based assembly techniques may involve one or more suitable polymerase enzymes that can catalyze a template-based extension of a nucleic acid in a 5' to 3' direction in the presence of suitable nucleotides and an annealed template. A polymerase may be thermostable. A polymerase may be obtained from recombinant or natural sources. In some embodiments, a thermostable polymerase from a thermophilic organism may be used. In some embodiments, a polymerase may include a 3'→5' exonuclease/proofreading activity. In some embodiments, a polymerase may have no, or little, proofreading activity (e.g., a polymerase may be a recombinant variant of a natural polymerase that has been modified to reduce its proofreading activity). Examples of thermostable DNA polymerases include, but are not limited to: Taq (a heat-stable DNA polymerase from the bacterium *Thermus aquaticus*); Pfu (a thermophilic DNA polymerase with a 3'→5' exonuclease/proofreading activity from *Pyrococcus furiosus*, available from for example Promega); VentR® DNA Polymerase and VentRO (exo-) DNA Polymerase (thermophilic DNA polymerases with or without a 3'→5' exonuclease/proofreading activity from *Thermococcus litoralis*; also known as Th polymerase); Deep VentR® DNA Polymerase and Deep VentR® (exo-) DNA Polymerase (thermophilic DNA polymerases with or without a 3'→5' exonuclease/proofreading activity from *Pyrococcus* species GB-D; available from New England Biolabs); KOD HiFi (a recombinant *Thermococcus kodakaraensis* KOD1 DNA polymerase with a 3'→5' exonuclease/proofreading activity, available from Novagen,); BIO-X-ACT (a mix of polymerases that possesses 5'-3' DNA polymerase activity and 3'→5' proofreading activity); Klenow Fragment (an N-terminal truncation of *E. coli* DNA Polymerase I which retains polymerase activity, but has lost the 5'→3' exonuclease activity, available from, for example, Promega and NEB); Sequenase™ (T7 DNA polymerase deficient in T-5' exonuclease activity); Phi29 (bacteriophage 29 DNA polymerase, may be used for rolling circle amplification, for example, in a TempliPhi™ DNA Sequencing Template Amplification Kit, available from Amersham Biosciences); TopoTaq (a hybrid polymerase that combines hyperstable DNA binding domains and the DNA unlinking activity of Methanopyrus topoisomerase, with no exonuclease activity, available from Fidelity Systems); TopoTaq HiFi which incorporates a proofreading domain with exonuclease activity; Phusion™ (a *Pyrococcus*-like enzyme with a processivity-enhancing domain, available from New England Biolabs); any other suitable DNA polymerase, or any combination of two or more thereof.

In some embodiments, the polymerase can be a SDP (strand-displacing polymerase; e.g, an SDPe—which is an SDP with no exonuclease activity). This allows isothermal PCR (isothermal extension, isothermal amplification) at a uniform temperature. As the polymerase (for example, Phi29, Bst) travels along a template it displaces the complementary strand (e.g., created in previous extension reactions). As the displaced DNAs are single-stranded, primers can bind at a consistent temperature, removing the need for any thermocycling during amplification, thereby avoiding or decreasing evaporation of the reaction mixture.

It should be appreciated that the description of the assembly reactions in the context of the oligonucleotides is not intended to be limiting. For example, other polynucleotides (e.g. single-stranded, double-stranded polynucleotides, restriction fragments, amplification products, naturally occurring polynucleotides, etc.) may be included in an assembly reaction, along with one or more oligonucleotides, in order to generate a polynucleotide of interest.

Aspects of the methods and devices provided herein may include automating one or more acts described herein. In some embodiments, one or more steps of an amplification and/or assembly reaction may be automated using one or more automated sample handling devices (e.g., one or more automated liquid or fluid handling devices). Automated devices and procedures may be used to deliver reaction reagents, including one or more of the following: starting nucleic acids, buffers, enzymes (e.g., one or more ligases and/or polymerases), nucleotides, salts, and any other suitable agents such as stabilizing agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides. Similarly, subsequent analysis of assembled polynucleotide products may be automated. For example, sequencing may be automated using a sequencing device and automated sequencing protocols. Additional steps (e.g., amplification, cloning, etc.) also may be automated using one or more appropriate devices and related protocols. It should be appreciated that one or more of the device or device components described herein may be combined in a system (e.g., a robotic system) or in a micro-environment (e.g., a micro-fluidic reaction chamber). Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc.). The system and any components thereof may be controlled by a control system.

Accordingly, method steps and/or aspects of the devices provided herein may be automated using, for example, a computer system (e.g., a computer controlled system). A computer system on which aspects of the technology provided herein can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer. One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the technology provided herein are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

Each of the different aspects, embodiments, or acts of the technology provided herein can be independently automated and implemented in any of numerous ways. For example, each aspect, embodiment, or act can be independently implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the technology provided herein comprises at least one computer-readable medium (e.g., a computer memory, a floppy disk, a compact disk, a tape, etc.) encoded with a computer program (i.e., a plurality of instructions), which, when executed on a processor, performs one or more of the above-discussed functions of the technology provided herein. The computer-readable medium can be transportable such that the program stored thereon can be loaded onto any computer system resource to implement one or more functions of the technology provided herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology provided herein.

It should be appreciated that in accordance with several embodiments of the technology provided herein wherein processes are stored in a computer readable medium, the computer implemented processes may, during the course of their execution, receive input manually (e.g., from a user).

Accordingly, overall system-level control of the assembly devices or components described herein may be performed by a system controller which may provide control signals to the associated nucleic acid synthesizers, liquid handling devices, thermal cyclers, sequencing devices, associated robotic components, as well as other suitable systems for performing the desired input/output or other control functions. Thus, the system controller along with any device controllers together form a controller that controls the operation of a nucleic acid assembly system. The controller may include a general purpose data processing system, which can be a general purpose computer, or network of general purpose computers, and other associated devices, including communications devices, modems, and/or other circuitry or components to perform the desired input/output or other functions. The controller can also be implemented, at least in part, as a single special purpose integrated circuit (e.g., ASIC) or an array of ASICs, each having a main or central processor section for overall, system-level control, and separate sections dedicated to performing various different specific computations, functions and other processes under the control of the central processor section. The controller can also be implemented using a plurality of separate dedicated programmable integrated or other electronic circuits or devices, e.g., hard wired electronic or logic circuits such as discrete element circuits or programmable logic devices. The controller can also include any other components or devices, such as user input/output devices (monitors, displays, printers, a keyboard, a user pointing device, touch screen, or other user interface, etc.), data storage devices, drive motors, linkages, valve controllers, robotic devices, vacuum and other pumps, pressure sensors, detectors, power supplies, pulse sources, communication devices or other electronic circuitry or components, and so on. The controller also may control operation of other portions of a system, such as automated client order processing, quality control, packaging, shipping, billing, etc., to perform other suitable functions known in the art but not described in detail herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EQUIVALENTS

The present invention provides among other things novel methods and devices for high-fidelity gene assembly. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

Reference is made to PCT application PCT/US09/55267, to U.S. provisional application 61/257,591 filed Nov. 3, 2009, to U.S. Provisional application 61/264,643, filed on Nov. 25, 2009, U.S. Provisional Application 61/264,632, filed on Nov. 25, 2009, U.S. Provisional Application 61/264, 641 filed Nov. 25, 2009, U.S. Provisional Application 61/293,192, filed Jan. 7, 2010, U.S. provisional application 61/310,100, filed on Mar. 3, 2010 and U.S. provisional application 61/310,100 filed Mar. 3, 2010. All publications, patents and patent applications and sequence database entries mentioned herein are hereby incorporated by reference in their entirety as if each individual publication, patent or patent application was specifically and individually indicated to be incorporated by reference.

What is claimed is:

1. A composition for nucleic acid synthesis, the composition comprising:
water-in-oil emulsion sub-microvolume droplets for synthesis of a target nucleic acid comprising an aqueous phase, an immiscible oil phase, and a surfactant and/or other stabilizing molecules to maintain the integrity of the droplets,
wherein the synthesis of target nucleic acid occurs within the aqueous phase of the water-in-oil emulsion sub-microvolume droplet,
wherein the aqueous phase of each water-in-oil emulsion sub-microvolume droplet comprises a plurality of single-stranded support-bound oligonucleotides each having a predefined sequence, a plurality of single-stranded oligonucleotides in solution having complementary sequences to a terminal region of the plurality of single stranded support-bound oligonucleotides, a thermostable polymerase, a thermostable ligase and a glycerol, wherein glycerol increases the boiling point of the aqueous phase of the water-in-oil emulsion sub-microvolume droplets;
wherein each water-in-oil emulsion sub-microvolume droplet has an aqueous volume of 0.5 picoliters to 100 nanoliters, and
wherein the plurality of single-stranded oligonucleotides in solution together comprise the target polynucleotide.

2. The composition of claim 1 wherein the plurality of single-stranded support-bound oligonucleotides are bound to a solid support selected from the group consisting of a pin, a strip, a plate, a disk, an array, a rod, a particle and a nanoparticle.

3. The composition of claim 1 wherein the plurality of single-stranded support-bound oligonucleotides are bound to one or more beads.

4. The composition of claim 1 wherein the plurality of single-stranded support-bound oligonucleotides have different predefined sequences.

5. The composition of claim 1 wherein the aqueous phase of water-in-oil emulsion sub-microvolume droplet further comprises one or more of deoxyadenosine 5'-triphosphate, deoxythymidine 5'-triphosphate, deoxycytidine 5'-triphosphate, and deoxyguanosine 5'-triphosphate.

6. The composition of claim 1 wherein the aqueous phase of water-in-oil emulsion sub-microvolume droplet further comprises at least one primer.

7. A composition for synthesis of a target polynucleotide comprising:
one or more water-in-oil emulsion sub-microvolume droplets comprising an aqueous phase, an immiscible oil phase, and a surfactant and/or other stabilizing molecules to maintain the integrity of the droplets, wherein the synthesis of the target polynucleotide occurs within the aqueous phase of the one or more water-in-oil emulsion sub-mircovolume droplets;
a plurality of support-bound oligonucleotides contained in the aqueous phase of one or more water-in-oil emulsion sub-microvolume droplets, each support-bound oligonucleotide having a predefined sequence and having a terminal region comprising a sequence identical to a terminal region of another oligonucleotide, the plurality of oligonucleotides together comprise the target polynucleotide;
wherein the aqueous phase of each of the one or more water-in-oil emulsion sub-microvolume droplets further comprises a thermostable polymerase, a primer, deoxyribonucleoside triphosphates, a thermostable ligase and glycerol, wherein glycerol increases the boiling point of the water-in-oil emulsion sub-microvolume droplets and
wherein each water-in-oil emulsion sub-microvolume droplet has an aqueous volume of 0.5 picoliters to 100 nanoliters.

8. The composition of claim 7 wherein the plurality of single-stranded support-bound oligonucleotides are bound to a solid support selected from the group consisting of a pin, a strip, a plate, a disk, an array, a rod, a particle and a nanoparticle.

9. The composition of claim 7 wherein the plurality of support-bound oligonucleotides are single-stranded oligonucleotides having different predefined sequences.

10. The composition of claim 7 wherein the primer is a unique primer or a universal primer.

11. A composition for synthesis of a target polynucleotide comprising:
one or more water-in-oil emulsion sub-microvolume droplets comprising an aqueous phase, an immiscible oil phase, and a surfactant and/or other stabilizing molecules to maintain the integrity of the droplets, wherein the synthesis of the target polynucleotide occurs within the aqueous phase of the one or more water-in-oil emulsion sub-microvolume droplets;
one or more pluralities of single-stranded support-bound oligonucleotides and one or more pluralities of single-stranded oligonucleotides in solution in the aqueous phase of the one or more water-in-oil emulsion sub-microvolume droplets, each plurality of single-stranded oligonucleotides having a different predefined sequence;

wherein the aqueous phase of the one or more water-in-oil emulsion sub-microvolume droplets further comprises a thermostable polymerase, a primer, deoxyribonucleosides triphosphates, a thermostable ligase, and glycerol, wherein glycerol increases the boiling point of the aqueous phase of the water-in-oil emulsion sub-microvolume droplets, wherein each of the one or more water-in-oil emulsion sub-microvolume droplets has an aqueous volume of 0.5 picoliters to 100 nanoliters, and wherein a first single-stranded oligonucleotide in solution has a terminal region comprising a sequence complementary to a sequence of a terminal region of the support-bound oligonucleotide, and wherein the first single-stranded oligonucleotide in solution has a terminal region comprising a sequence complementary to a sequence of a terminal region of a second single-stranded oligonucleotide in solution, the plurality of single-stranded oligonucleotides in solution together comprising the target polynucleotide.

12. The composition of claim 11 wherein each of the one or more plurality of single-stranded support-bound oligonucleotides are bound to a solid support selected from the group consisting of a pin, a strip, a plate, a disk, an array, a rod, a particle and a nanoparticle.

* * * * *